(12) United States Patent  
Hoerr et al.

(10) Patent No.: US 9,108,217 B2
(45) Date of Patent: Aug. 18, 2015

(54) NANOPARTICLE COATING OF SURFACES

(75) Inventors: Robert A. Hoerr, Shoreview, MN (US); John V. Carlson, St. Michael, MN (US)

(73) Assignee: Nanocopoeia, Inc., St. Paul, MN (US)

(*) Notice: Subject to any disclaimer, the term of this patent is extended or adjusted under 35 U.S.C. 154(b) by 1618 days.

(21) Appl. No.: 12/023,747

(22) Filed: Jan. 31, 2008

(65) Prior Publication Data

US 2015/0158051 A1 Jun. 11, 2015

Related U.S. Application Data

(63) Continuation-in-part of application No. 11/669,937, filed on Jan. 31, 2007.

(60) Provisional application No. 60/838,708, filed on Aug. 18, 2006, provisional application No. 60/764,229, filed on Jan. 31, 2006, provisional application No. 60/887,597, filed on Jan. 31, 2007.

(51) Int. Cl.
*A61K 47/00* (2006.01)
*B05D 1/06* (2006.01)
*B05D 1/34* (2006.01)
*B05D 1/36* (2006.01)

(52) U.S. Cl.
CPC .. *B05D 1/06* (2013.01); *B05D 1/34* (2013.01); *B05D 1/36* (2013.01)

(58) Field of Classification Search
USPC .............................. 424/489; 239/135; 427/2.1
See application file for complete search history.

(56) References Cited

U.S. PATENT DOCUMENTS

| | | | |
|---|---|---|---|
| 3,521,125 A | 7/1970 | Nelson |
| 3,608,823 A | 9/1971 | Buschor |
| 3,654,534 A | 4/1972 | Fischer |
| 3,905,330 A | 9/1975 | Coffee |
| 4,002,777 A | 1/1977 | Juvinall et al. |
| 4,039,145 A | 8/1977 | Felici et al. |
| 4,265,641 A | 5/1981 | Natarajan |
| 4,328,940 A | 5/1982 | Malcolm |
| 4,414,603 A | 11/1983 | Masuda |
| 4,476,515 A | 10/1984 | Coffee |
| 4,578,290 A | 3/1986 | Komon et al. |

(Continued)

FOREIGN PATENT DOCUMENTS

| | | |
|---|---|---|
| CA | 2435721 A1 | 8/2002 |
| CA | 2436524 A1 | 8/2002 |

(Continued)

OTHER PUBLICATIONS

Leitner et al., Composite Supercapacitor Electrodes, Dec. 2003, Journal of Solid State Electrochemistry, vol. 8, Issue 1, pp. 15 and 16.*

(Continued)

*Primary Examiner* — Dah-Wei D Yuan
*Assistant Examiner* — Andrew Bowman
(74) *Attorney, Agent, or Firm* — Schwegman Lundberg & Woessner, P.A.

(57) ABSTRACT

A nanoparticle coated hydrogel may be formed by a method of electrospraying nanoparticles on to a surface includes providing a drug and polymer combination in solvent to an inner capillary of a coaxial dual capillary spray nozzle. A coating with a drug that releases over time may be provided. Open and closed matrixes may be selectively formed to help modify time release periods.

20 Claims, 38 Drawing Sheets

(56) References Cited

U.S. PATENT DOCUMENTS

| | | |
|---|---|---|
| 4,634,057 A | 1/1987 | Coffee et al. |
| 4,659,012 A | 4/1987 | Coffee |
| 4,748,043 A | 5/1988 | Seaver et al. |
| 4,749,125 A | 6/1988 | Escallon et al. |
| 4,795,330 A | 1/1989 | Noakes et al. |
| 4,846,407 A | 7/1989 | Coffee et al. |
| 4,945,050 A | 7/1990 | Sanford et al. |
| 4,946,899 A | 8/1990 | Kennedy et al. |
| 5,036,006 A | 7/1991 | Sanford et al. |
| 5,044,564 A | 9/1991 | Sickles |
| 5,066,587 A | 11/1991 | Jones et al. |
| 5,091,205 A | 2/1992 | Fan |
| 5,100,792 A | 3/1992 | Sanford et al. |
| 5,120,657 A | 6/1992 | McCabe et al. |
| 5,141,131 A | 8/1992 | Miller, Jr. et al. |
| 5,149,655 A | 9/1992 | McCabe et al. |
| 5,179,022 A | 1/1993 | Sanford et al. |
| 5,204,253 A | 4/1993 | Sanford et al. |
| 5,219,746 A | 6/1993 | Brinegar et al. |
| 5,222,663 A | 6/1993 | Noakes et al. |
| 5,240,842 A | 8/1993 | Mets |
| 5,247,842 A | 9/1993 | Kaufman et al. |
| 5,354,556 A | 10/1994 | Sparks et al. |
| 5,371,015 A | 12/1994 | Sanford et al. |
| 5,433,865 A | 7/1995 | Laurent |
| 5,457,041 A | 10/1995 | Ginaven et al. |
| 5,475,228 A | 12/1995 | Palathingal |
| 5,478,744 A | 12/1995 | Sanford et al. |
| 5,506,125 A | 4/1996 | McCabe et al. |
| 5,516,670 A | 5/1996 | Kuehnle et al. |
| 5,525,510 A | 6/1996 | McCabe et al. |
| 5,584,807 A | 12/1996 | McCabe |
| 5,621,605 A | 4/1997 | Inaba et al. |
| 5,655,517 A | 8/1997 | Coffee |
| 5,683,556 A | 11/1997 | Nomura et al. |
| 5,685,482 A | 11/1997 | Sickles |
| 5,702,754 A | 12/1997 | Zhong |
| 5,807,436 A | 9/1998 | Stachelhaus et al. |
| 5,813,614 A | 9/1998 | Coffee |
| 5,837,313 A | 11/1998 | Ding et al. |
| 5,846,595 A | 12/1998 | Sun et al. |
| 5,866,400 A | 2/1999 | Palsson et al. |
| 5,873,523 A | 2/1999 | Gomez et al. |
| 5,897,911 A | 4/1999 | Loeffler |
| 5,915,377 A | 6/1999 | Coffee |
| 5,973,904 A | 10/1999 | Pui et al. |
| 5,980,972 A | 11/1999 | Ding |
| 5,992,244 A | 11/1999 | Pui |
| 6,068,199 A | 5/2000 | Coffee |
| 6,074,688 A | 6/2000 | Pletcher et al. |
| 6,093,557 A | 7/2000 | Pui et al. |
| 6,096,070 A | 8/2000 | Ragheb et al. |
| 6,105,571 A | 8/2000 | Coffee |
| 6,105,877 A | 8/2000 | Coffee |
| 6,120,847 A | 9/2000 | Yang et al. |
| 6,126,086 A | 10/2000 | Browner et al. |
| 6,143,037 A | 11/2000 | Goldstein et al. |
| 6,143,370 A | 11/2000 | Panagiotou et al. |
| 6,145,391 A | 11/2000 | Pui et al. |
| 6,207,195 B1 | 3/2001 | Walsh et al. |
| 6,242,369 B1 | 6/2001 | Vogt et al. |
| 6,251,136 B1 | 6/2001 | Guruwaiya et al. |
| 6,252,129 B1 | 6/2001 | Coffee |
| 6,277,448 B2 | 8/2001 | Strutt et al. |
| 6,318,640 B1 | 11/2001 | Coffee |
| 6,364,903 B2 | 4/2002 | Tseng et al. |
| 6,368,658 B1 | 4/2002 | Schwarz et al. |
| 6,399,362 B1 | 6/2002 | Pui et al. |
| 6,419,692 B1 | 7/2002 | Yang et al. |
| 6,419,745 B1 | 7/2002 | Burkett et al. |
| 6,457,470 B1 | 10/2002 | Coffee |
| 6,517,888 B1 | 2/2003 | Weber |
| 6,579,573 B2 | 6/2003 | Strutt et al. |
| 6,595,208 B1 | 7/2003 | Coffee et al. |
| 6,632,671 B2 | 10/2003 | Unger |
| 6,645,569 B2 | 11/2003 | Cramer et al. |
| 6,669,980 B2 | 12/2003 | Hansen |
| 6,670,607 B2 | 12/2003 | Wood et al. |
| 6,684,879 B1 | 2/2004 | Coffee et al. |
| 6,737,463 B2 | 5/2004 | Yadav et al. |
| 6,743,463 B2 | 6/2004 | Weber et al. |
| 6,746,869 B2 | 6/2004 | Pui et al. |
| 6,764,720 B2 | 7/2004 | Pui et al. |
| 6,861,088 B2 | 3/2005 | Weber et al. |
| 6,880,554 B1 | 4/2005 | Coffee |
| 6,894,160 B2 | 5/2005 | Capan et al. |
| 6,933,331 B2 | 8/2005 | Yadav et al. |
| 6,989,169 B2 | 1/2006 | Ripoll et al. |
| 7,193,124 B2 | 3/2007 | Coffee |
| 2002/0007869 A1 | 1/2002 | Pui et al. |
| 2002/0065553 A1 | 5/2002 | Weber |
| 2002/0151004 A1 | 10/2002 | Craig |
| 2003/0143315 A1 | 7/2003 | Pui et al. |
| 2003/0161937 A1 | 8/2003 | Leiby et al. |
| 2003/0232087 A1 | 12/2003 | Lawin et al. |
| 2003/0236514 A1 | 12/2003 | Schwarz |
| 2004/0069632 A1 | 4/2004 | Ripoll et al. |
| 2004/0081745 A1 | 4/2004 | Hansen |
| 2004/0161498 A1 | 8/2004 | Ripoll et al. |
| 2004/0177807 A1 | 9/2004 | Pui et al. |
| 2004/0200729 A1 | 10/2004 | Boulais et al. |
| 2004/0234748 A1 | 11/2004 | Stenzel |
| 2005/0015046 A1 | 1/2005 | Weber et al. |
| 2005/0023368 A1 | 2/2005 | Valpey et al. |
| 2005/0042455 A1 | 2/2005 | Gedig et al. |
| 2005/0055078 A1 | 3/2005 | Campbell |
| 2005/0064008 A1 | 3/2005 | Bucay-Couto et al. |
| 2005/0074478 A1 | 4/2005 | Ofstead et al. |
| 2005/0075714 A1 | 4/2005 | Cheng et al. |
| 2005/0101020 A1 | 5/2005 | Salem et al. |
| 2005/0116070 A1 | 6/2005 | Ganan Calvo et al. |
| 2005/0149177 A1 | 7/2005 | Weber et al. |
| 2005/0158372 A1 | 7/2005 | O'Leary et al. |
| 2005/0175772 A1 | 8/2005 | Worsham et al. |
| 2005/0222485 A1 | 10/2005 | Shaw et al. |
| 2005/0273161 A1 | 12/2005 | Malik et al. |
| 2005/0277577 A1 | 12/2005 | Hunter et al. |
| 2005/0288774 A1 | 12/2005 | Case et al. |
| 2006/0002973 A1 | 1/2006 | Barry et al. |
| 2006/0024810 A1 | 2/2006 | Khadkikar et al. |
| 2006/0038027 A1 | 2/2006 | O'Connor |
| 2006/0057259 A1 | 3/2006 | Ripoll et al. |
| 2006/0062820 A1 | 3/2006 | Gertner et al. |
| 2006/0067968 A1 | 3/2006 | Chudzik et al. |
| 2006/0078922 A1 | 4/2006 | Edwards et al. |
| 2006/0088566 A1 | 4/2006 | Parsonage et al. |
| 2006/0099235 A1 | 5/2006 | Blakstvedt et al. |
| 2006/0100568 A1 | 5/2006 | Tan |
| 2007/0106361 A1 | 5/2007 | Epstein |
| 2007/0154554 A1 | 7/2007 | Burgermeister et al. |
| 2007/0278103 A1 | 12/2007 | Hoerr et al. |
| 2009/0104269 A1* | 4/2009 | Graham et al. ............... 424/489 |

FOREIGN PATENT DOCUMENTS

| | | |
|---|---|---|
| CA | 2520702 A1 | 10/2004 |
| CH | 0550022 A | 6/1974 |
| CN | 1052695 A | 7/1991 |
| CN | 1651604 A | 8/2005 |
| DE | 19846656 A1 | 4/1999 |
| DE | 19909333 A1 | 11/1999 |
| EP | 0234841 A2 | 9/1987 |
| EP | 0258016 A1 | 3/1988 |
| EP | 0270356 A2 | 6/1988 |
| EP | 0258016 B1 | 9/1990 |
| EP | 0405884 A1 | 1/1991 |
| EP | 0429234 A2 | 5/1991 |
| EP | 0434616 A1 | 6/1991 |
| EP | 0429234 A3 | 12/1991 |
| EP | 0434616 B1 | 11/1995 |
| EP | 0429234 B1 | 10/1998 |
| EP | 9842446 A1 | 10/1998 |
| EP | 1355537 A1 | 10/2003 |
| EP | 1364718 A1 | 11/2003 |

(56) References Cited

FOREIGN PATENT DOCUMENTS

| ES | 2180405 A | 2/2003 |
|---|---|---|
| JP | 06242273 A2 | 9/1994 |
| JP | 2004531365 T2 | 10/2004 |
| MX | 3006862 A | 10/2004 |
| WO | WO-9100915 A1 | 1/1991 |
| WO | WO-9107487 A1 | 5/1991 |
| WO | WO-9307465 A1 | 4/1993 |
| WO | WO-94012285 A1 | 6/1994 |
| WO | WO-9713503 A1 | 4/1997 |
| WO | WO-97049484 A1 | 12/1997 |
| WO | WO-9803267 A1 | 1/1998 |
| WO | WO-98042446 A1 | 10/1998 |
| WO | WO-9856894 A1 | 12/1998 |
| WO | WO-9903517 A1 | 1/1999 |
| WO | WO-9930812 A1 | 6/1999 |
| WO | WO-9930835 A1 | 6/1999 |
| WO | WO-9931019 A1 | 6/1999 |
| WO | WO-0187491 A1 | 11/2001 |
| WO | WO-02060275 A1 | 8/2002 |
| WO | WO-02060591 A1 | 8/2002 |
| WO | WO-03028622 A2 | 4/2003 |
| WO | WO-03082363 A1 | 10/2003 |
| WO | WO-04047882 A2 | 6/2004 |
| WO | WO-2005074913 A2 | 8/2005 |
| WO | WO-06003504 A1 | 1/2006 |
| WO | WO-2006086654 A2 | 8/2006 |
| WO | WO-2007089883 A2 | 8/2007 |
| WO | WO-2007089883 A3 | 8/2007 |
| WO | WO-2008094700 A2 | 8/2008 |
| WO | WO-2008094700 A3 | 8/2008 |

OTHER PUBLICATIONS

Crititech, [Online]. Retrieved from the Internet: <URL: www.crititech.com/technology>, (Jun. 5, 2002), 5 pages.
Binks Electrostatic spray painting equipment, Product Literature, 7 pages.
"U.S. Appl. No. 11/669,937 , Response filed Jul. 29, 2011 to Non Final Office Action mailed Mar. 2, 2011", 23 pgs.
"U.S. Appl. No. 11/669,937, Final Office Action mailed Dec. 22, 2011", 10 pgs.
"U.S. Appl. No. 11/669,937, Non Final Office Action mailed Nov. 13, 2012", 15 pgs.
"U.S. Appl. No. 11/669,937, Non Final Office Action mailed Mar. 2, 2011", 7 pgs.
"U.S. Appl. No. 11/669,937, Response filed Apr. 16, 2013 to Non Final Office Action mailed Nov. 13, 2012", 9 pgs.
"U.S. Appl. No. 11/669,937, Response filed May 22, 2012 to Final Office Action mailed Dec. 22, 2011", 9 pgs.
"U.S. Appl. No. 11/669,937, Response filed Dec. 23, 2010 to Restriction Requirement mailed Sep. 22, 2010", 6 pgs.
"U.S. Appl. No. 11/669,937, Restriction Requirement mailed Sep. 22, 2010", 6 pgs.
"U.S. Appl. No. 11/701,200, Non-Final Office Action mailed May 11, 2010", 22 p.
"European Application Serial No. 08725099.9 , Response filed Sep. 27, 2011 to Examination Report mailed Nov. 23, 2010", 3 pgs.
"European Patent Application No. 08725099.9, Office Action mailed Nov. 23, 2010", 5 pgs.
"Final Program—Minnesota Nanotechnology Summit", Minnesota Nanotechnology Summit: Opportunities and Challenges, http://www.particlesociety.org/Spring2000.html Minneapolis, MN, (Mar. 17, 2000), 4 pgs.
"International Application Serial No. PCT/US2008/001410, International Preliminary Report on Patentability mailed Aug. 13, 2009", 8 pgs.
"International Application Serial No. PCT/US2008/001410, Search Report mailed Nov. 7, 2008", 4 pgs.
"International Application Serial No. PCT/US2008/001410, Written Opinion mailed Nov. 7, 2008", 7 pgs.
"PCT Application No. PCT/US2007/00270, International Search Report mailed Aug. 24, 2007", 4 pgs.
"PCT Application No. PCT/US2007/00270, International Search Written Opinion mailed Aug. 24, 2007", 7 pgs.
et al., "State of the art overview and forecasts based on existing information of nanotechnology in the field of nanomaterials", Work Documents on Nanomaterials, (2004), 75 pages.
et al., "Work Document on Nanomaterials: State of the Art Overview and Forecasts Based on Existing Information of Nanotechnology in the Field of Nanomaterials", [online] Willems & van den Wildenberg, Oct. 2004 [retrieved on Dec. 23, 2010]. Retrieved from the Internet: <URL: http://www.nanoroadmap.it/sectoral%20reports/sect%20report%20materials.pdf>, 75 p.
Adachi, M., et al., "High-efficiency unipolar aerosol charger using a radioactive alpha source", Aerosols : Science, Industry, Health, and Environment : Proceedings of the Third International Aerosol Conference,, Sep. 24-27, 1990, Kyoto International Conference Hall, Kyoto, Japan / editors, Senichi Masuda, Kanji Takahashi ; Pergamon Press, NY, (1990), 439-441.
Adachi, M., et al., "Unipolar and Bipolar Diffusion Charging of Ultrafine Aerosol Particles", J. Aerosol Sci., 16(2), (1985), 109-123.
Alexis, Frank, et al., "In vitro study of release mechanisms of paclitaxel and rapamycin from drug-incorporated biodegradable stent matrices.", Journal of Controlled Release, 98(1), (2004), 67-74.
Buscher, P., et al., "Performance of a unipolar square wave diffusion charger with variable nt-product", J. Aerosol Sci., 25(4), (1998), 651-663.
Chen, D., et al., "Design and Evaluation of a Nanometer Aerosol Differential Mobility Analyzer (Nano-DMA)", J. Aerosol Sci.,29(5/6), (1998), 497-509.
Chen, Da-Ren, et al., "Electrospraying of Conducting Liquids for Monodisperse Aerosol Generation in the 4nm to 1.8nm Diameter Range", J.Aerosol Sci., 26(6), (1995), 963-977.
Chen, Da-Ren, et al., "Experimental Investigation of Scaling Laws of Electrospraying: Dielectric Constant Effect", Aerosol Science and Technology; 27(3), (1997), 367-380.
Fuchs, N. A, "On the Stationary Charge Distribution on Aerosol Particles in a Bipolar Ionic Atmosphere", Geodis: Pura. Appl.; vol. 56, (1963), 185-193.
Ganan-Calvo, Alfonso, "Generation of Steady Liquid Microthreads and Micron-Sized Monodisperse Sprays in Gas Streams.", Phys. Rev. Lett., 80(2), (1998), 285-288.
Ganan-Calvo, Alfonso M, "New microfluidic technologies to generate respirable aerosols for medical applications", J. of Aerosol Sci., 30(Suppl. 1), (1993), S541-S542.
Hoppel, W. A, et al., "The Nonequililbrium Character of the Aerosol Charge Distribution Produced by Neutralizers", Aerosol Sci. & Technol., 12, (1990), 471-496.
Jouyban, A, et al., "A simple relationship between dielectric constant of mixed solvents with solvent composition and temperature", Int J Pharm., 269(2), (2004), 353-60.
Lui, Benjamin, et al., "On unipolar dissision charging of aerosol particles in the continuum regime", J. Colloid Interface Sci., 58, (1977), 142-149.
Pui, D., et al., "Unipolar Diffusion Charging Ultrafine Aerosols", Aerosol Sci. Techn., 8, (1988), 173-187.
Pui, David, et al., "Nanometer Particles: A New Frontier for Multidisciplinary Research", J. Aerosol Sci., 28(4), (1997), 539-544.
Puskas, Judit E, et al., "Polyisobutylene-based biomaterials", Journal of Polymer Science Part A: Polymer Chemistry, 42(13), (2004), 3091-3109.
Ranade, S. V, et al., "Physical characterization of controlled release of paclitaxel from the TAXUS Express2 drug-eluting stent", J Biomed Mater Res A., 71(4), (2004), 625-34.
Re, Maria-Ines, "Formulating Drug Delivery Systems by Spray Drying", Drying Technology, 24(4), (2006), 443-446.
Romay, Francisco J., et al., "Free electron charging of ultrafine aerosol particles", J. Aerosol Sci, 23(7), (1992), 679-692.
Romay, Francisco J, et al., "On the Combination coefficient of positive ions with ultrafine neutral particles in the transition and free—molecule regimes", Aerosol Sci. Techn., 17, (1992), 134-147.

(56) References Cited

OTHER PUBLICATIONS

Romay, Francisco J, et al., "Unipolar Diffucion Charginmg of Aerosol Particles at Low Pressure", Aerosol Sci. Techn, 15, (1991), 60-68.
Rulison, A. J, et al., "Scale-up of electrospray atomization using lienar arrays of Taylor cones", Review of Scientific Instruments, 64(3), (1993), 683-686.
Salata, Oleg V, et al., "Tools of Nanotechnology: Electrospray", Current Nanoscience, 1(1), (2005), 25-33.
Shi, Y., et al., "Current advances in sustained-release systems for parenteral drug delivery", Expert opinion on Drug Delivery, 2(6), (2005), 1039-58.
Songstad, D. D, et al., "Advances in alternative DNA delivery techniques", Plant Cell, Tissue and Organ Culture, 40, (1995), 1-15.
Szycher, M., et al., "Drug-eluting stents to prevent coronary restenosis", http://www.implantsciences.com/pdf/IMXpaperv2-rev2.pdf, (2002), 1-10.
Verhoeven, M., et al., "DSIMS characterization of adrug-containing polymer-coated cardiovascular stent", J.Controlled Release, 96, (2004), 113-121.
Wiedensohler, A., et al., "A novel unipolar charger for ultrafine aerosol particles with minimal particle losses", J. Aerosol Sci., 25(4), (1994), 639-650.
Yokoyama, T., et al., "Nanoparticle Technology for the Production of Functional Materilas", Hosokawa Powder Technology Research Institute, KONA No. 23, (2005), 7-17.
Young, Timothy J, et al., "Phospholipid-Stabilized Nanoparticles of Cyclosporine A by Rapid Expansion from Supercritical to Aqueous Solution", AAPS Pharm.SciTech.5(1) Article 11, (2003), 1-16.
"U.S. Appl. No. 11/669,937 , Response filed Oct. 7, 2013 to Final Office Action mailed Aug. 7, 2013", 12 pgs.
"U.S. Appl. No. 11/669,937, Final Office Action mailed Aug. 7, 2013", 12 pgs.
"U.S. Appl. No. 11/669,937, Notice of Non-Compliant Amendment mailed Aug. 11, 2011", 1 pg.
"U.S. Appl. No. 11/669,937, Response filed Sep. 9, 2011 to Notice of Non-Compliant Amendment mailed Aug. 11, 2011", 5 pgs.
"Canadian Application Serial No. 2,677,081, Office Action mailed Jan. 31, 2014", 3 pgs.
"Canadian Application Serial No. 2,677,081, Response filed Jul. 29, 2014 to Office Action mailed Jan. 31, 2014", 101 pgs.
"European Application Serial No. 08725099.9. Office Action mailed Oct. 30, 2014", 4 pgs.
U.S. Appl. No. 11/669,937, Non Final Office Action mailed Mar. 27, 2014, 10 pgs.

* cited by examiner

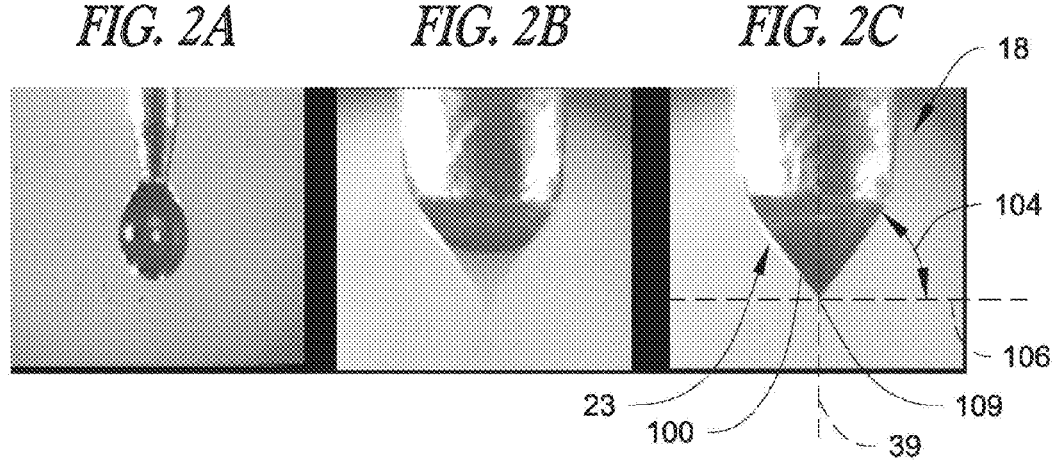
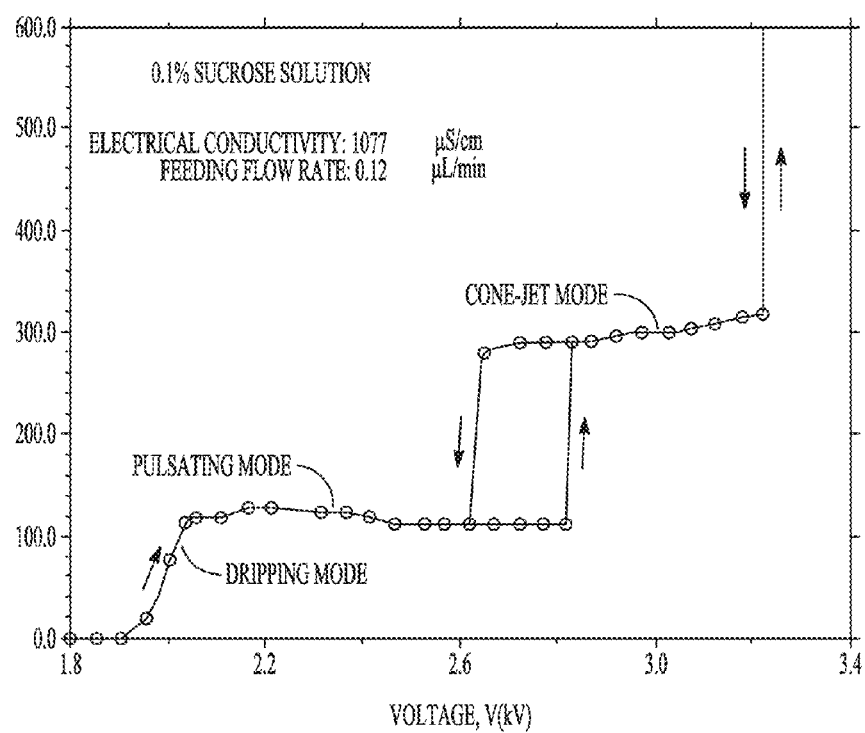

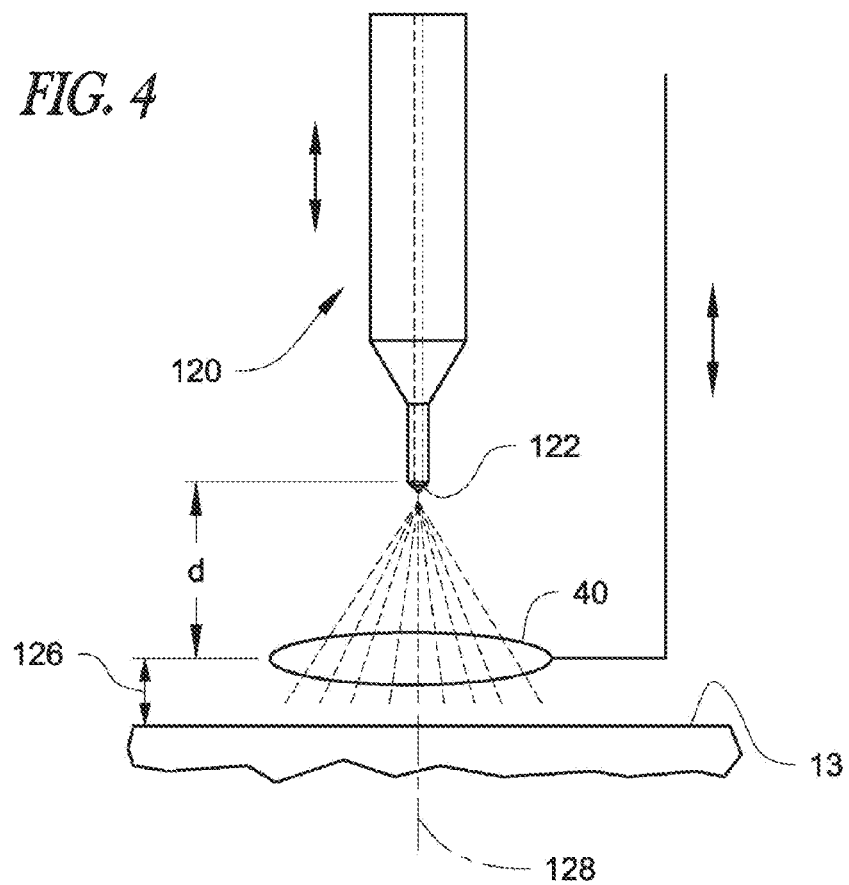
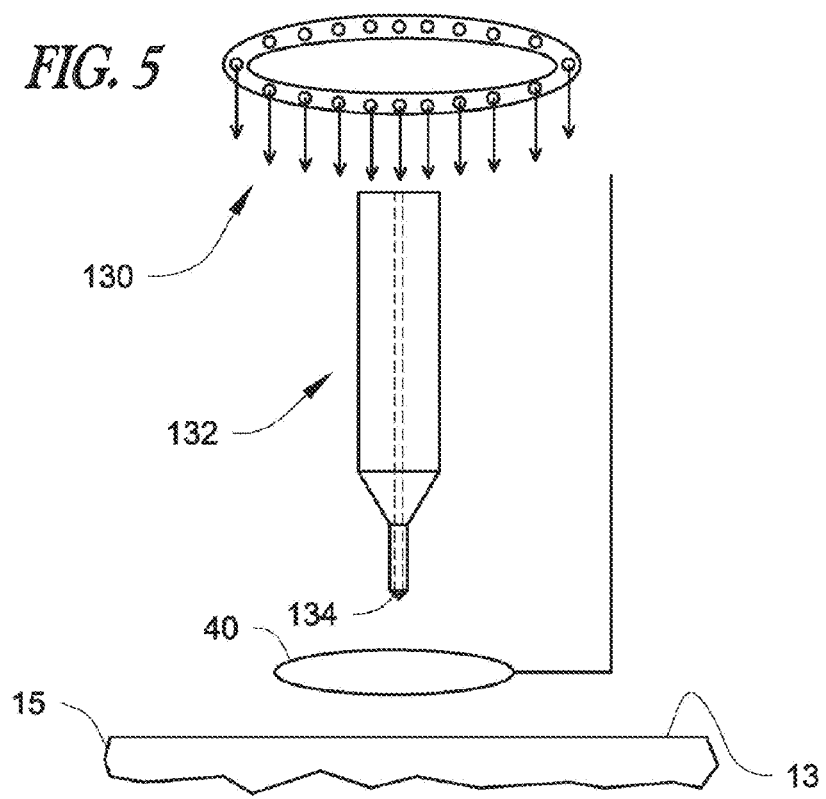

FIG. 9

| Control Factors | | | | | | Outcomes | | |
|---|---|---|---|---|---|---|---|---|
| Concentration of PLCL and dexamethasone (DEX) in spray fluid | | Diluent solution | Additive, conductivity (μS $cm^{-1}$) | | Ratio spray fluid/ diluent | Spray distance | Spray Voltage (kV) | Coating Weight | Plate |
| PLCL% | DEX% | | | | | | | | |
| 5 | | Acetone | | 0.3 | 1:5 | 7 | 4.031 | 90 | a |
| 5 | | Acetone | | 0.3 | 2:5 | 16 | 4.600 | 130 | b |
| 5 | | Acetone | $HNO_3^-$ | 6.8 | 1:5 | 16 | 5.362 | 50 | c |
| 5 | | Acetone | $HNO_3^-$ | 6.8 | 2:5 | 7 | 4.898 | 160 | d |
| 5 | 0.5 | Acetone | | 0.3 | 1:5 | 7 | 4.002 | 40 | e |
| 5 | 0.5 | Acetone | | 0.3 | 2:5 | 16 | 4.720 | 280 | f |
| 5 | 0.5 | Acetone | $HNO_3^-$ | 6.8 | 1:5 | 16 | 5.345 | 70 | g |
| 5 | 0.5 | Acetone | $HNO_3^-$ | 6.8 | 2:5 | 7 | 4.639 | 170 | h |

FIG. 10

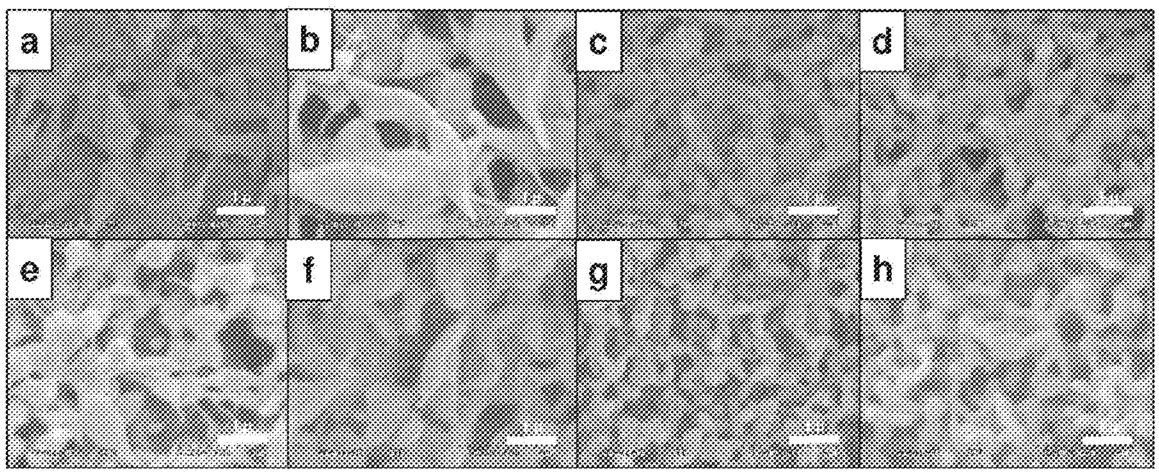

| Measured Outcomes | Process Parameter | | | | |
|---|---|---|---|---|---|
| | Polymer concentration | Presence of drug | Conductivity of diluent solution | Polymer-to-diluent ratio | Spray distance |
| Coating weight | ↕ | ↕ | ↕ | ← | ↕ |
| Spray voltage | ↕ | ↕ | ← | ↕ | ← |
| Roundness of coating particles | ↕ | ↕ | ← | ↕ | ↕ |

*FIG. 11*

| Coating polymer | Coating surface | No. stents per lot | Stent starting weight (μg) Mean ± SD | Coating net weight (μg) mean ± SD | Lot coating coefficient of variation |
|---|---|---|---|---|---|
| PLCL | Open matrix | 11 | 1256 ± 19 | 513.6 ± 12.9 μg | 2.5% |
| PLCL | Smooth | 12 | 1277 ± 53 | 461.7 ± 16.4 μg | 3.6% |
| Chronoflex AR | Smooth | 12 | 1266 ± 20 | 555.0 ± 15.7 μg | 2.8% |

| Coating polymer | Coating surface | Solvent(s) | Transfer efficiency |
|---|---|---|---|
| PLCL | Open matrix | Acetone | 30.5 ± 0.8% |
| PLCL | Smooth | Acetone, chloroform | 41.1 ± 1.6% |
| Chromaflex AR | Smooth | Tetrahydrofuran, methanol | 56.2 ± 1.5% |

| Column | a | b | c | d | e | f |
|---|---|---|---|---|---|---|
| Stent | Crimped | Expanded | Crimped | Expanded | Crimped | Expanded |
| Coating | PLCL, open matrix | | PLCL, smooth | | Chronoflex AR, smooth | |
| View, type of image and magnification | Overall view, light microscope 10X | | | | | |
| | Survey view, SEM 100X | | | | | |
| | Outer strut surface, SEM 5000X | | | | | |
| | Outer strut surface, SEM 20,000X | | | | | |
| | Inner strut surface, SEM 20,000X | | | | | |

*FIG. 21*

| SAMPLE # | COATING PROPERTIES | STENT | SOLIDS % | SOLVENT | IF(μl/min) | OUTER | OF(μl/min) | D(NOZZLE TO STENT)(mm) | # OF PASSES | WEIGHT (μg) |
|---|---|---|---|---|---|---|---|---|---|---|
| 241 | OPEN | BSC | 0.9%SIBS+0.1%PTx | 85%THF14%MEOH | 1.5 | 14%MEOH86%THF: MG1: 50/50 | 4 | 16 | 2 | 330 |
| 256 | CLOSED | BSC | 0.81%SIBS+0.09%PTx | 90%MG1: 10% TOLUENE | 3.5 | 10%MEOH90%THF | 5 | 8 | 1 | 330 |
| 382 | WITH DEX | BSC | 0.9%SIBS+0.1%PTx+0.1%DEX | 85%THF14%MEOH | 2.5 | | | 16 | 1 | 390 |
| 219 | DRUG-EBED | BSC | 0.9%SIBS+0.1%PTx | 85%THF14%MEOH | 2.5 | 10%MEOH90%THF | 1 | 12 | 1 | 300 |

FIG. 24A

| Sample # | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 279 | Open | BSC | 0.9%SIBS+0.1%PTx | 99%THF | 3 | 15%MEOH85%THF | 4 | 16 | 1 | 320 |
| 318 | Closed | BSC | 0.9%SIBS+0.1%PTx | 99%THF | 1 | 15%MEOH85%THF | 8 | 16 | 1 | 120 |

| Sample# | Coating properties | Stent | Solids% | Solvent | IF(ul/min) | Outer | OF(ul/min) | Dt(Nozzle to stent)(mm) | # of Passes | Weight (ug) |
|---|---|---|---|---|---|---|---|---|---|---|
| 326 | Closed | BSC | 2.25%SIBS+0.25%PTx | 97.5%THF | 1 | 15

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 308 | Open | BSC | 4.5%SIBS+0.5%PTx | 95%THF | 0.85 | 15%MEOH:85%THF | 5 | 16 | 1 | 410 |
| 373 | Closed | BSC | 0.9%SIBS+0.1%PTx | 20%MG:80%Toluene | 1 | 15%MEOH:85%THF | 3 | 20 | 1 | 110 |

(308)

(373)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 593 | Open | Pulse | 5 PLCL+.5DEX | Acetone | 1.5 | Acetone + HNO3 | 5 | 12 | 1 | 530 |
| 614 | Close | Pulse | 5 PLCL+.5DEX | Acetone | 0.75 | 40 Acetone/60 CHCL3 | 10 | 10 | 1 | 490 |

(593)

(614)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 69 | Close | spring | 5 PLCL | Acetone | 0.75 | Acetone/chloroform 50/50 | 10 | 8 | 1 | 590 |
| 76 | Open | BSC | 5 PLCL | Acetone | 1 | Acetone | 5 | 8 | 1 | 820 |

(69)

(76)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 635 | Close | Pulse | 2 CFR/2 DEX | THF/MEOH 5/1 | 2 | THF/MEOH 5/1 | 8 | 8 | 1 | 550 |

(635)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 275 | Open | BSC | 0.9%SIBS+0.1%aPTx | 69.7%THF/29.3%MEK | 1 | 10%MeOH/90%THF | 2 | 12 | 1 | 190 |

(275)

| Sample# | Coating properties | Stent | Solids% | Solvent | IF(ul/min) | Outer | OF(ul/min) | D(Nozzle to stent)(mm) | # of Passes | Weight (ug) |
|---|---|---|---|---|---|---|---|---|---|---|
| 130 | 3rd-nozzle | BSC | 2 Dexa | 2/3 blend of ETOH/Acetone | 0.75 | 5% PLCL in acetone | 1.5 | 8 | 1 | 1020 |

(130)

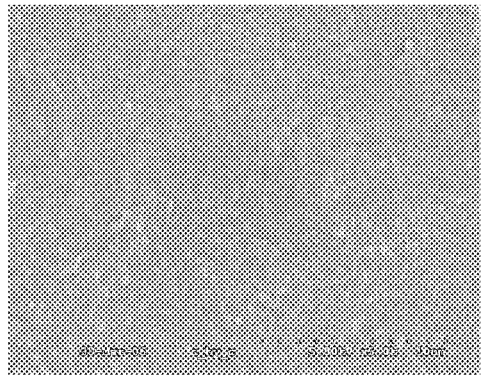 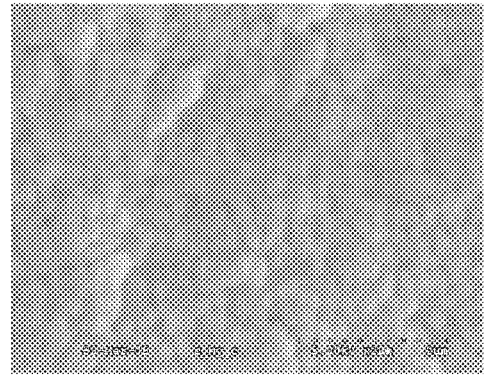
FIG. 39A    FIG. 39B
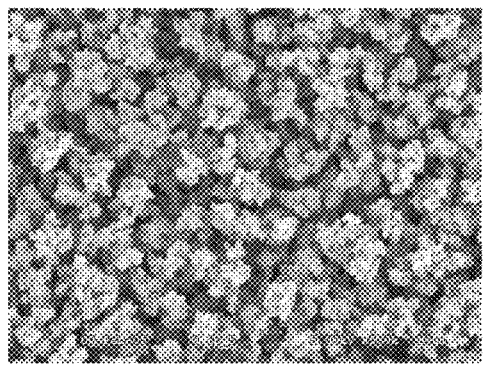 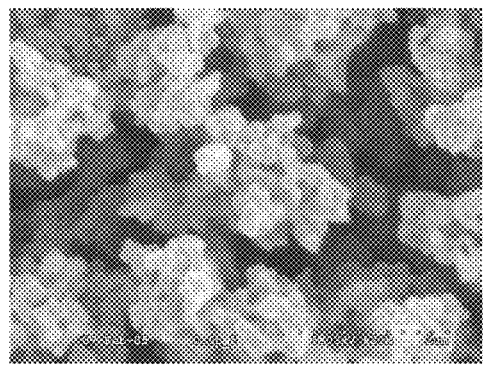
FIG. 40A    FIG. 40B

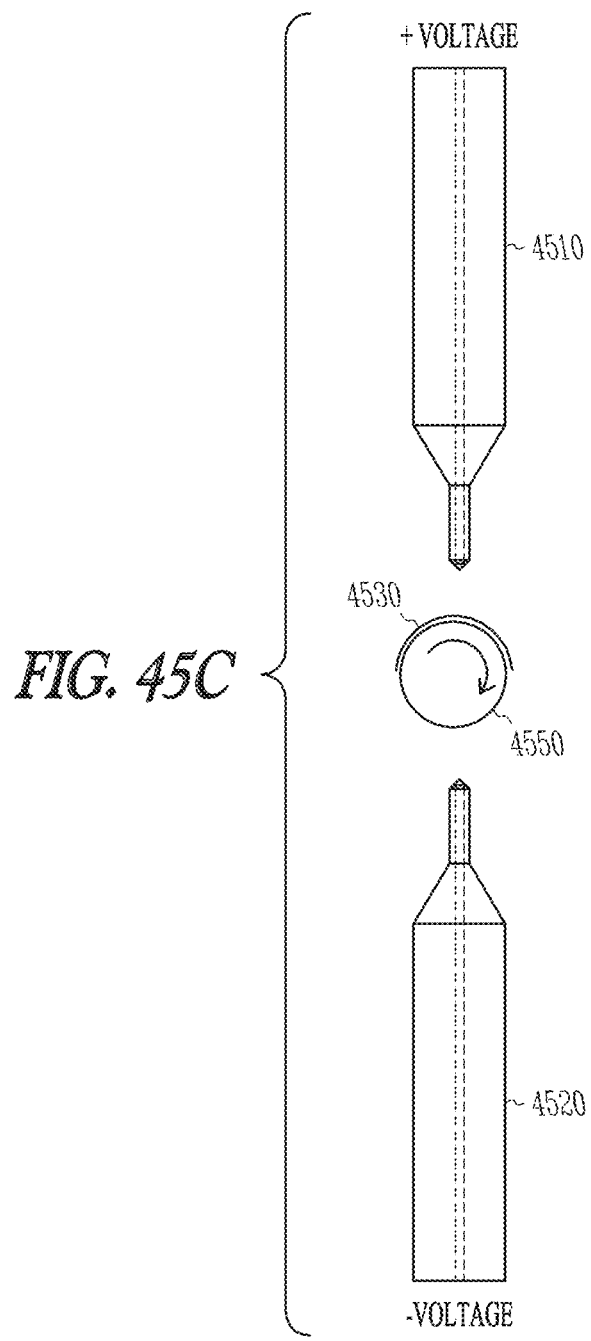

NANOPARTICLE COATING OF SURFACES

RELATED APPLICATIONS

This application claims priority to U.S. application Ser. No. 11/669,937 (entitled NANOPARTICLE COATING OF SURFACES, filed Jan. 31, 2007) which is incorporated herein by reference, which application claims priority to U.S. Provisional Application Ser. No. 60/838,708 (titled NANOPARTICLE COATING OF A HYRODROGEL, filed Aug. 18, 2006) and also claims priority to U.S. Provisional Application Ser. No. 60/764,229 (titled ELECTROSPRAYING APPARATUS AND METHOD FOR COATING OBJECTS, filed Jan. 31, 2006), and claims priority to U.S. Provisional Application Ser. No. 60/887,597 (entitled NANOPARTICLE COATING OF SURFACES, filed Jan. 31, 2007) which is incorporated herein by reference.

GOVERNMENT FUNDING

This invention was made with Government support under Grant Number 1 R43 HL 079690-01-A1 awarded by NIH and Grant Number IIP-051-2496 awarded by NSF. The United States Government has certain rights in the invention.

BACKGROUND

The present invention relates to coating objects, and more particularly, the present invention relates to coating objects (e.g., medical devices) using electrospray technology.

It is often beneficial to coat objects (e.g., medical devices) so that the surfaces of such devices have desired properties or provide desired effects. For example, it is useful to coat medical devices to provide for the localized delivery of therapeutic agents to target locations within the body, such as to treat localized disease (e.g., heart disease) or occluded body lumens. Local drug delivery may be achieved, for example, by coating balloon catheters, stents, and the like with therapeutic agent to be locally delivered. The coating of medical devices may provide for controlled release, which includes long-term or sustained release, of a bioactive material.

Aside from facilitating localized drug delivery, medical devices are coated with materials to provide beneficial surface properties. For example, medical devices are often coated with radiopaque materials to allow for fluoroscopic visualization during placement in the body. It is also useful to coat certain devices to achieve enhanced biocompatibility and to improve surface properties such as lubriciousness.

Further, for example, it is often beneficial to coat stents, e.g., for the controlled release of pharmacological agents, surface property control and effects, etc. Stents are implanted within vessels in an effort to maintain the patency thereof by preventing collapse and/or impeding restenosis. For example, implantation of a stent may be accomplished by mounting the stent on the expandable portion of a balloon catheter, maneuvering the catheter through the vasculature so as to position the stent at the treatment site within the body lumen, and inflating the balloon to expand the stent so as to engage the lumen wall. The stent deforms in the expanded configuration allowing the balloon to be deflated and the catheter removed to complete the implantation procedure. Further, for example, the use of self-expanding stents obviates the need for a balloon delivery device. Instead, a constraining sheath that is initially fitted above the stent is simply retracted once the stent is in position adjacent the treatment site. Stents and stent delivery catheters are well known in the art and the various configurations thereof makes it impossible to describe each and every stent structure or related materials.

The success of a stent placement can be assessed by evaluating a number of factors, such as thrombosis, neointimal hyperplasia, smooth muscle cell migration, and proliferation following implantation of the stent, injury to the artery wall, overall loss of lumenal patency, stent diameter in vivo, thickness of the stent, and leukocyte adhesion to the lumenal lining of stented arteries. The chief areas of concern are early subacute thrombosis and eventual restenosis of the blood vessel due to intimal hyperplasia.

Therapeutic pharmacological agents have been developed to address some of the concerns associated with the placement of the stent. It is often desirable to provide localized pharmacological treatment of the vessel at the site being supported by the stent. As it would be convenient to utilize the implanted stent for such purpose, the stent may serve both as a support for a lumenal wall as well as a delivery vehicle for the pharmacological agent.

Conventionally, coatings have been applied to objects such as medical devices, including stents, by processes such as dipping, spraying, vapor deposition, plasma polymerization, as wells as electroplating and electrostatic deposition. Although many of these processes have been used to produce satisfactory coatings, there are numerous potential drawbacks associated therewith.

For example, it is often difficult to achieve coatings of uniform thicknesses, both on the individual parts and on batches of parts. Also, many coating materials are otherwise difficult to use, such as those that are incompatible, insoluble, unsuspendable, or that are unstable coating solutions.

Further, for example, many coating processes result in coatings that do not provide a uniform drug dose per medical device. Further, such conventional methods have generally failed to provide a quick, easy, and inexpensive way of providing drugs onto a stent. For example, deficiencies of such conventional methods are, at least in part, related to the control of the coating process (e.g., the ability to control the coating uniformity and thickness, the ability to control the size of particles used to coat the device, the control of the coating so as to control the rate of the release of the drug upon implantation of the stent, etc.). Likewise, in many processes, the coating materials are fairly costly, and in many coating processes such coating materials are wasted due to the type of coating methods being used.

Therefore, the need for an effective method and system of coating objects such as medical devices exists.

There is a further need for an effective method of coating non-conductive materials and surfaces, such as plastic.

BRIEF DESCRIPTION OF THE DRAWINGS

FIGS. 2A, 2B and 2C are images of a capillary electrospray dispensing end (e.g., spray head) progressing from the start of spray (FIG. 2A) to the "pulsating" mode (FIG. 2B) to the "cone-jet" mode (FIG. 2C) according to the present invention.

FIG. 2D is a graph showing a current versus voltage curve for electrospray of a particular solution.

FIG. 4 shows a general diagrammatical illustration of one embodiment of an electrospray dispensing device including a ring electrode for controlling particle spread as well as for illustrating control of nozzle to target surface distance for applying one or more of the types of coatings such as generally shown in FIGS. 3A-3C.

FIG. 5 shows a general diagrammatical illustration of one embodiment of an electrospray dispensing device including a ring electrode for controlling particle spread as well as a gas flow for use in controlling the application of one or more of the types of coatings such as generally shown in FIGS. 3A-3C.

FIG. 9 shows a table of experimental conditions and outcome measures to assess impact of process parameters on achieving desired coatings according to one or more examples provided herein.

FIGS. 10a, 10b, 10c, 10d, 10e, 10f, 10g and 10h show experiment image results for the parameter sets outlined in FIG. 9 according to one or more examples provided herein.

FIG. 11 shows a table of the relationship of process parameters to experimental outcome variables according to one or more examples provided herein.

FIG. 21 shows a table for use in describing the images of FIGS. 20a-f according to one or more examples provided herein.

FIG. 24A shows a table of solutions and parameters used in the application of one or more coatings according to one or more examples provided herein.

FIG. 26A shows a table of a solution and parameters used in the application of one or more coatings according to one or more examples provided herein, and FIG. 26B shows respective images (higher magnification and lesser magnification) of the resulting coating corresponding to the Sample # shown in the table.

FIGS. 39A and 39B are SEM images of a freeze-dried hydrogel with griseofulvin coating according to an example embodiment.

FIGS. 40A and 40B are SEM images of a metal plate coated with griseofulvin according to an example embodiment.

FIGS. 45A, 45B and 45C are block line diagrams illustrating multiple spray head electrospray devices for coating surfaces such as non-conductive surfaces.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Systems and methods for coating objects (e.g., coated stent structures), such as medical devices and also systems and methods for coating objects (e.g., coating of medical devices, depositing a film on any object such as for texturing the surface thereof, providing a protective layer on an object, providing a textured surface to improve cellular adherence and/or biocompatibility, constructing an active or passive layer of an integrated circuit, etc.) are described. Selected types of coatings having uniform properties may be accomplished. Further, the system and methods provide for the efficient and cost effective use of coating materials. Multiple embodiments are also described for obtaining timed release of drugs, and for coating both conductive and non-conductive materials using electronanospray devices.

Figure 1:
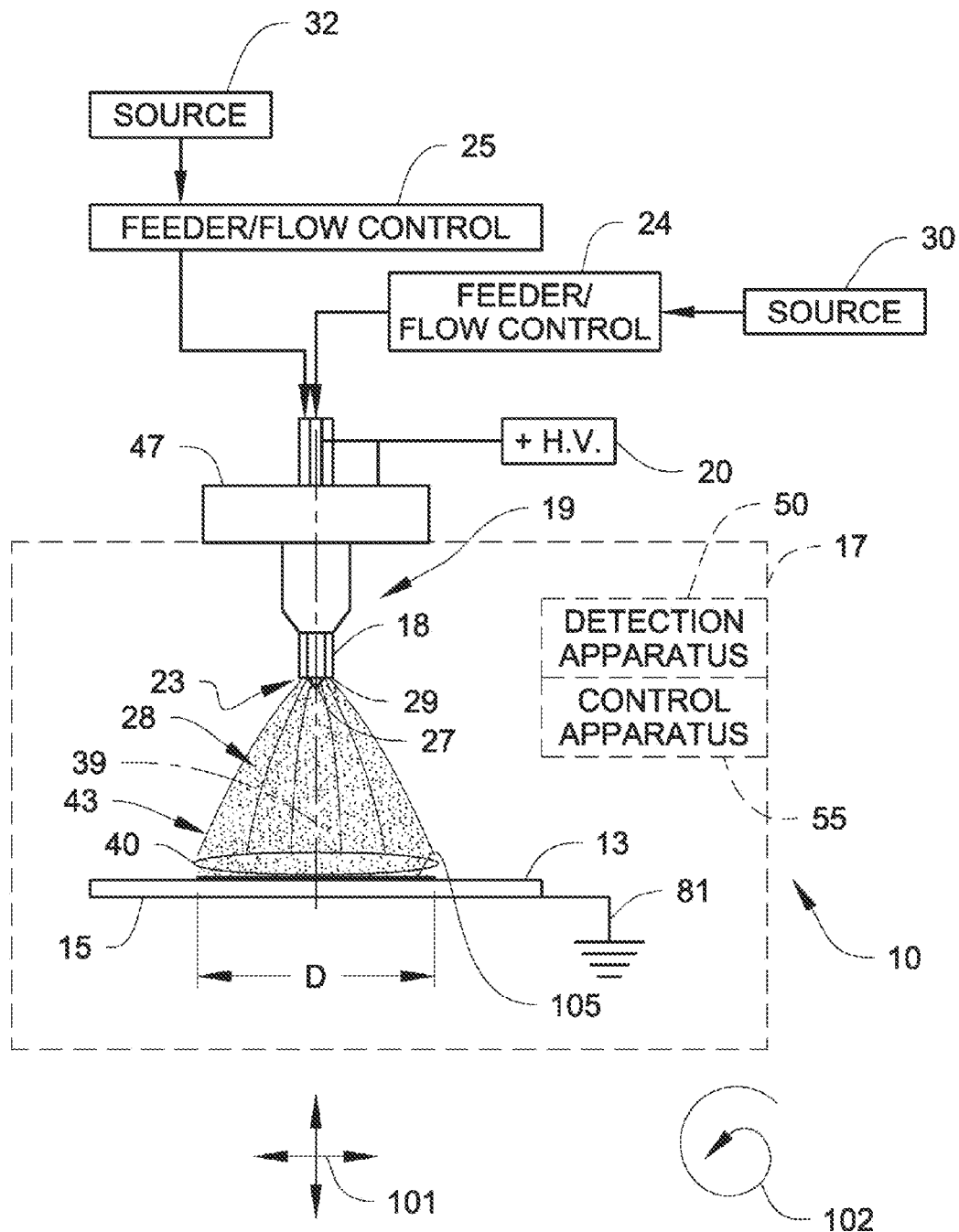
FIG. 1 is a general diagram illustrative of one embodiment of an object coating system, e.g., a nanoparticle generator system using electrospray techniques for coating surfaces that includes a dual opening nozzle in accordance with the present invention.

An electrospray coating system, such as electrospray coating system 10 illustratively shown in FIG. 1, can be controlled so as to provide for one or more selected types of coatings according to the present invention. For example, the electrospray coating system 10 may be controlled to provide an open matrix coating on one or more surface portions of an object, a closed film coating on one or more surface portions of an object, or an intermediate matrix coating on one or more surface portions of an object.

Figure 3A:
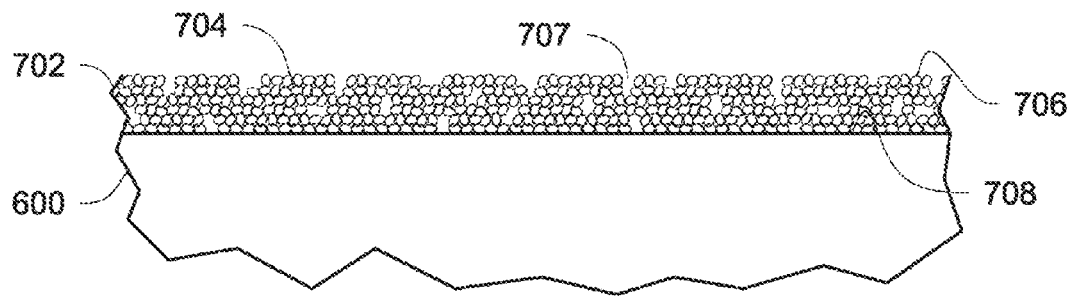
FIGS. 3A, 3B and 3C illustratively show three types of coatings that may be selected and/or applied according to the present invention including an open matrix coating in FIG. 3A, a closed film coating in FIG. 3B, and an intermediate matrix coating in FIG. 3C.
Figure 3B:
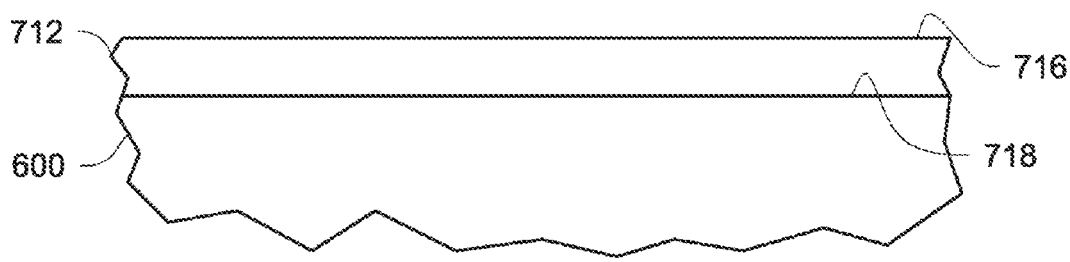
Figure 3C:
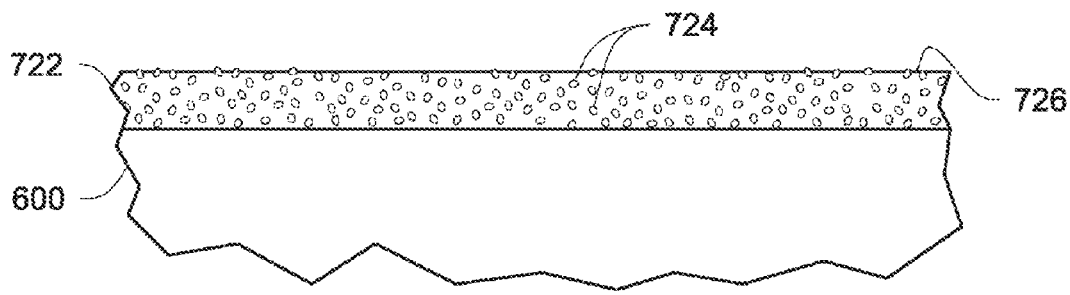

FIGS. 3A-3C illustratively show three types of coatings that may be selected and/or applied according to the present invention including an open matrix coating in FIG. 3A, a closed film coating in FIG. 3B, and an intermediate matrix coating in FIG. 3C. Such coatings can be selected for application on one or more surface portions of an object 600. Such selection may be performed manually or automatically. Generally, the selection of the type of coating to be applied may include a user determining that it is desirable to use one or more of the types of coatings to obtain one or more types of functionality provided by the coating. Selection may involve a user operating a system and setting various parameters or selecting various compositions to be used in the spraying process so as to apply a particular selected coating, or may include user selection of a coating type on a system such that the system automatically selects one or more parameters or various compositions to be used in the spraying process so as to apply a particular selected coating, or a combination of both.

Generally as described herein, the selected coating type may be applied using two or more different types of liquid compositions (e.g., a liquid spray composition and a liquid diluent composition provided at two or more concentric openings at a dispensing end of a nozzle structure) and/or under one or more conditions or controlled parameters according to the present invention. For example, as described herein, an open matrix coating may be applied to a surface of an object by controlling the type of liquid diluent composition and/or the conductivity of a composition provided at an outer opening of a dual opening nozzle structure, or by controlling the ratio of a liquid diluent composition provided at an outer opening of a dual opening nozzle structure to the liquid spray composition provided at an inner opening of a dual opening nozzle structure.

As used herein, an open matrix coating refers to a coating wherein a supermajority (i.e., greater than two-thirds) of the particles used to create the coating are visibly discrete but attached creating a relatively irregular coating compared to a closed film coating. In other words, when an open matrix coating is viewed using microscopy, the particles used to form the coating can be visually separated by the viewer into discrete particles even though such particles are attached, or otherwise coupled, to one or more other particles of the coating.

An open matrix coating 702 is illustratively shown in FIG. 3A applied to surface 708. The open matrix coating 702 includes discrete particles 704 attached, or otherwise coupled, to one or more other particles 704 of the coating 702.

The open matrix coating has visibly distinct open regions 707 appearing darker than the surface 706 of the coating 702 when viewed using scanning electron microscopy (SEM). Such opening regions 707 extend at least one or more nominal diameters of the particles 704 deeper into the surface 706 (e.g., from the upper most surface of the outer most particles at the surface 706 of the coating 702). At least in one embodiment, such opening regions 707 exist throughout the thickness of the coating 702 as shown in FIG. 3A. Further, particles with distinct boundaries and shape similar to those seen on the surface 706 of the coating are visible using SEM in one or more planes beneath the surface 706 of the coating.

At least in one embodiment of the open matrix coating, the particles are substantially round particles. As used herein, substantially round particles refers to particles that are not elongated fiber particles; elongated fiber particles as used herein are fiber particles that have a body length that is at least ten (10) times the diameter of a maximum cross-section taken at any point along the length of the particle. In other words, a substantially round particle does not have an elongated body but is more spherically shaped, although such particles will not necessarily be spherical.

Generally, the surface area at the upper surface 706 of the coating 702 is a rough surface that can be characterized in one or more different manners. One manner of characterizing a rough surface of the open matrix coating is based on the cross-section particle size of the particles of the coating being deposited. At least in one embodiment, the nominal cross-section particle size is represented by the nominal diameter through the center of the particles. In one embodiment, the nominal diameter for particles of a rough open matrix coating according to the present invention is in the range of about 1 nm to about 2000 nm. In another embodiment, the cross-section nominal diameter through the center of the particles is greater than about 10 nm, in another embodiment less than about 1000 nm, in another embodiment less than about 500 nanometers, and in another embodiment less than about 200 nm.

Alternatively, or in addition to other manners of characterizing the rough surface of the coating 702, a rough surface may be characterized based on a comparison of the surface area of the rough surface relative to the surface area of a completely smooth surface (i.e., a surface with no structure, e.g., valleys, peaks, etc.) having a substantially identical shape as the rough surface, e.g., the shape of the structure upon which a rough portion is formed. In one embodiment of the present invention, a rough surface is a generally homogenous surface (i.e., a surface structure without any substantial irregularities from one part of the surface to another part of the surface such as, for example, deep depressions, large spikes, unusually large particles compared to the other particles of the layer, etc.) that has a surface area greater than about 1.2 times the surface area of a completely smooth surface having a substantially identical shape (i.e., substantially identical shapes having the same base dimensional characteristics, e.g., in the case of a planar surface the occupancy area of both the completely smooth and rough surface are equivalent). However, the surface shape may be of a planar shape, a curved shape, or any other shape. In yet another embodiment, the roughness of the surface has a surface area that is greater than about 1.5 times the surface area of a completely smooth surface having a substantially identical shape.

For example, as shown in FIG. 3A, the rough surface 706 of coating 702 has a generally planar shape. The surface area of the rough surface 706 can be compared to a surface area (XY) (only the x axis is shown with the y axis extending into the page) of a completely smooth surface 708 having a planar shape, i.e., a shape identical to the shape of the rough surface 706. Therefore, at least in one embodiment, the surface area of rough surface 706 of the coating 702 is greater than about 1.2(XY). Yet further, in another embodiment, the surface area of rough surface 706 of the coating 702 is greater than about 2.0(XY).

As used herein, a closed film coating refers to a coating wherein a supermajority (i.e., greater than two-thirds) of the particles used to create the coating are not visibly discrete, but rather have flowed together to form a relatively smooth coating as compared to an open matrix coating. In other words, when a closed film coating is viewed using microscopy, the particles used to form the coating are not visually separable into discrete particles by the viewer but rather the coating is seen as a generally smooth coating with no or little irregularity.

A closed film coating 712 is illustratively shown in FIG. 3B. The closed film coating 712 includes substantially no discrete particles, but rather the coating 712 has an upper surface 716 that is smooth and flowing. In other words, the surface area of the smooth surface 716 is substantially equal to a surface area (XY) (only the x axis is shown with the y axis extending into the page) of a completely smooth surface 718 having an identical shape, or at least is less than about 1.1 (XY).

As used herein, an intermediate matrix coating refers to a coating wherein less than a supermajority (i.e., less than two-thirds) of the particles used to create the coating are visibly discrete, however, more than superminority (i.e., more than one third) of the particles are visibly discrete (e.g., in such a coating, many particles are visibly discrete with flowing material generally existing therebetween). In other words, when an intermediate matrix coating is viewed using microscopy, between one third to two thirds of the particles used to form the coating are visually separable into discrete particles by the viewer, with the remainder of the coating being a flowing material connecting such particles forming a coating that is slightly irregular compared to a closed film coating but less irregular than an open matrix coating.

An intermediate matrix coating 722 is illustratively shown in FIG. 3C. The intermediate matrix coating 722 includes some visibly discrete particles 724, and has an upper surface 726 that is slightly rough. In other words, the surface area of the slightly rough surface 726 is less rough than an open matrix coating but rougher than a closed film coating.

As used herein, when reference is made to a uniform coating, the uniformity extends through the entire thickness of a selected coating unless otherwise stated. For example, the structure of a uniform open matrix coating (i.e., wherein the particles are visibly discrete but connected to one or more other particles) is substantially the same throughout the entire thickness of the coating (e.g., the particles are visibly discrete at the surface of an object being coated as well as throughout the coating including the upper rough surface of the open matrix coating).

One will recognize that two or more selected types of coatings may be applied to create a combined coating of two or more selected coatings (e.g., a closed film coating overlaid with an open matrix coating). In such a case, uniformity of such selected layers would apply to the respective layers.

At least in one embodiment, an open matrix coating may be sprayed by electrospray from a cone-jet provided with one or more flows of liquid compositions (e.g., such as using a dual opening nozzle structure such as described herein, a single opening nozzle structure, etc). The one or more flows include at least two active ingredients. The at least two active ingredients in the one or more flows exist in a predetermined ratio. The coating includes a plurality of particles adherent to one another but discrete such as described above with reference to an open matrix coating. The plurality of particles have a nominal diameter of less than 500 nanometers, and may even have a nominal diameter of less than 200 nanometers. Each particle of the coating includes the at least two active ingredients in substantially the same predetermined ratio as the at least two active ingredients exist in the one or more flows. As used in this context, the term substantially refers to a deviation of +/−20%.

In one or more further embodiments of such a coating, the at least two active ingredients include a polymer and biologically active material (e.g., the biologically active ingredient may be encapsulated by the polymer or they may exist in more of a matrix form. Further, the at least two active ingredients are uniformly distributed through the thickness of the coating and open regions like those described with reference to the open matrix coating are present throughout the thickness of the coating.

One embodiment of an electrospray coating system 10 according to the present invention is shown in FIG. 1. The electrospray coating system 10 employs the generation of particles, such as, for example, nanoparticles, for use in coating objects, such as medical devices (e.g., coating such devices with polymers and/or drugs, with one selected coating or more than one selected coating).

As further described herein, the systems and methods according to the present invention may use one or more electrospray apparatus having dual opening nozzle structures, or one or more nozzle structures that have more than two openings at the dispensing ends thereof, such as that previously described in U.S. Pat. No. 6,093,557 to Pui, et al., entitled "Electrospraying Apparatus and Method for Introducing Material into Cells," issued 25 Jul. 2000 (e.g., dual capillary configurations), and also described in the papers entitled, "Electrospraying of Conducting Liquids for Dispersed Aerosol Generation in the 4 nm to 1.8 μM Diameter Range" by Chen, et al., *J. Aerosol Sci.*, Vol. 26, No. 6, pp. 963-977 (1995), and entitled "Experimental Investigation of Scaling Laws for Electrospraying: Dielectric Constant Effect" by Chen, et al., *Aerosol Science and Technology,* 27:367-380 (1997), or may use a single or multiple nozzle structure electrospray apparatus such as described in U.S. Patent Application US-2002-0007869-A1, entitled "High Mass Throughput Particle Generation Using Multiple Nozzle Spraying," published on 24 Jan. 2002, or may use one or more nozzle structures described in US 2003/0143315 A1, entitled "Coating Medical Devices," published 31 Jul. 2003, which are all hereby incorporated in their entirety by reference thereto.

As shown in FIG. 1, the illustrative electrospray coating system 10 employs a dispensing apparatus 19 to establish a spray of coating particles 28 (e.g., spray of microdroplets which evaporate to form a spray of coating particles). The dispensing apparatus 19 includes at least one nozzle structure 18 that includes at least two concentric openings 27, 29 (e.g., concentric about axis 39) that terminate at the dispensing end 23 thereof. Openings that terminate at the dispensing end 23 do not need to terminate in a single plane (e.g., a plane orthogonal to axis 39 along which the nozzle structure 18 extends. Rather, the termination of one of the openings may be closer to the object 15 being coated than the other (e.g., the inner opening may terminate closer to the object 15). The openings receive source material to establish the spray of coating particles 28 forward of the dispensing end 23, e.g., in the direction of the object 15 to be coated. The coating particles 28 are moved toward at least one surface 13 of the object 15 (e.g., medical device) to form a coating 105 thereon.

The object 15 is located in a defined volume (shown generally by the dashed line 17) where the coating particles 28 are provided. The defined volume 17 may, for example, be a reactor chamber, a chamber of a coating system, a vacuum chamber, a pressurized and/or heated chamber, a volume of open air space, a chamber including a particular gas environment, etc.

The system 10 includes a source holding apparatus 30 for providing a first liquid spray composition to an inner opening 27 of the two concentric openings terminating at the dispensing end 23 of the nozzle structure 18 such as under control of control mechanism 55, e.g., hardware and/or software control, via feeder/flow control 24. The system 10 further includes a source holding apparatus 32 for providing a second liquid diluent composition to an outer opening 29 of the two concentric openings terminating at the dispensing end 23 of the nozzle structure 18 under control of control mechanism 55, e.g., hardware and/or software control, via feeder/flow control 25. An electrospray nozzle structure 18 can deliver a controlled feed rate of source material in the establishment of a spray of coating particles within the envelope of the nozzle structure. The nozzle structure 18 is configured to operate in a cone-jet mode as further described herein to provide a spray of coating particles 28 to the defined volume 17 where the object 15 is located using the source material (e.g., the first flow of liquid spray composition and the second flow of liquid diluent composition).

With further reference to FIG. 1, the nozzle structure 18 of the dispensing device 19 may include a nozzle structure having any one of various configurations and employing any number of different components, e.g., dual capillary electrodes, micro-machined tapered openings alone or in combination with capillary electrodes, etc. For example, as previously indicated, the nozzle structure may include one or more nozzle structures as described in U.S. Pat. No. 6,093,557 or U.S. Patent Application US-2002-0007869-A1. Various types of nozzle structures, and dispensing devices with which they may be used, are shown and described herein. However, nozzle structures described in documents incorporated herein may provide further nozzle structures that may be used according to the present invention and/or may provide additional description regarding the nozzle structures that have also been described generally herein.

The nozzle structure 18 of the electrospray dispensing device 19 provides a charged spray with a high concentration of charged particles. Generally, the concentration of charged particles in the spray is in the range of about $10^5$ particles per cubic centimeter (particles/cc) to about $10^{12}$ particles/cc. Due to the space charge effect, i.e., the effect created by the charge repulsion of charged particles, a spray of substantially dispersed particles having the same polarity charge is provided with the particles distributed substantially uniformly across a spray area.

As used herein, the term substantially dispersed particles refers to uniformly and/or nonuniformly sized particles separated by an applied repulsive electrostatic force. Thus, the electrospray process is a consistent and reproducible transfer process. Further, because the charged particles of the spray repel one another, agglomeration of the particles is avoided. This results in a more uniform particle size. "Substantially dispersed" particles are not to be confused with monodisperse particles which involves the general degree of uniformity of the particles sprayed, e.g., the standard deviation of the particles from a nominal size.

Generally, according to the configuration as shown at FIG. 1, the charge is applied by concentration of charge on the spray of coating particles through evaporation (at least partially) in an established electrical field 43 prior to the coating particles forming a selected coating 105 on the object 15. In other words, as further described herein the liquid sprayed generally evaporates to concentrate a charge of a liquid portion thereof on the coating particles, e.g., on the active ingredient of the particles. This results in the spray of charged coating particles 28 as described further herein.

FIG. 1 generally shows a diagrammatical illustration of the operation of the electrospray coating system 10 for establishing a charged spray 28 from the nozzle structure 18. The nozzle structure 18 receives a first flow of the liquid spray composition from the material source holding apparatus 30 and a second flow of the liquid diluent composition from the material source holding apparatus 32. For example, the material source holding apparatus 30 may include a liquid spray composition including drug active ingredients and a polymer at least partially dissolved in a solvent suitable to dissolve such a polymer therein. Further, for example, the material source holding apparatus 32 may include a liquid diluent composition including the same or a different solvent as the solvent in the liquid spray composition.

Generally, a conductive material 47, e.g., a conductive plate, positions the nozzle structure 18 in a particular configuration. For example, the conductive material 47 may be adapted to be connected to a high voltage source 20. The nozzle structure 18 includes a conductive structure, e.g., a capillary tube structure such as illustratively shown in FIGS. 7A and 7B, which defines orifices, e.g., openings 27 and 29, that terminate at the dispensing end 23 of the nozzle structure 18 for providing the flows of the liquid compositions.

Although various configurations for the source material holding apparatus 30 and 32 may be used according to the present invention, in one embodiment a single holding apparatus for each liquid composition is used to feed the respective liquid composition to the nozzle structure 18. One will recognize that any number of different and separate holding apparatus may be used or hold various different compositions and provide different compositions to one or more different nozzle structures (e.g., such as when multiple nozzle structures are used).

In one or more embodiments, the liquid spray composition and or liquid diluent composition may be pushed or pulled through the openings at the dispensing end 23 of the nozzle structure 18, e.g., pushed by a pump. In one embodiment, a compressed gas source, e.g., an inert source that is non-reactive with the composition, is provided to compress the composition and force fluid to flow through openings 27 and 29 of the nozzle structure 18. Although, in one embodiment, a compressed gas source may be used to provide such composition flow, other methods of providing such flow may also be used. For example, syringe pumps for each liquid composition may be used to establish the flow of material or the flow may also be controlled with use of a liquid pump (e.g., a syringe pump, a gravity feed pump, a pressure regulated liquid reservoir, etc.), a mass flow controller, or any other flow control devices suitable for feeding source material to the nozzle structure 18 as would be known to one skilled in the art.

The nozzle structure 18 positioned by and electrically coupled to the conductive structure 47 functions as a first electrode of the electrospray dispensing apparatus 19 with the dispensing end 23 of the nozzle structure 18 being positioned for dispensing charged microdroplets toward the object 15, or a surface 13 thereof. In the exemplary embodiment of FIG. 1, to set up the electric field 43, the object 15 may function as a second electrode structure, e.g., a grounded object 15 as shown by ground 81. An electrical potential difference is applied between the first electrode conductive structure 47 and the second electrode or grounded object 15 that is electrically isolated from the first electrode. One skilled in the art will recognize that the electrodes may be formed using one or more conductive elements, and such electrodes may take one of various different configurations. Further, the second electrode may also have a suitable opposite charge applied thereto (i.e., opposite to the first electrode).

Generally, in operation, a first flow of the liquid spray composition from the material source holding apparatus 30 and a second flow of the liquid diluent composition from the material source holding apparatus 32 is provided through the openings 27 and 29 of the nozzle structure 18, respectively. At least in one embodiment, a meniscus is formed at the dispensing end 23 where the inner opening 27 has an inner diameter in the range of about 6 microns to about 2 millimeters and an outer diameter in the range of about 8 microns to about 2.5 millimeters, and the outer opening 29 has an inner diameter in the range of about 15 microns to about 5 millimeters and an outer diameter in the range of about 30 microns to about 7 millimeters. Such dimensions are based on estimated clearances for different sizes of stainless steel capillaries and their wall thicknesses.

An electrical potential difference is applied to establish the nonuniform field 43 between the first electrode at the dispensing end 23 of the nozzle structure 18 and the second electrode (e.g., the grounded object 15). For example, a high positive voltage may be applied to the first electrode conductive structure 47 with the second electrode object 15 being grounded (e.g., the second electrode may also have a suitable opposite charge applied thereto; opposite to the first electrode. For example, a voltage difference that provides an electric field intensity greater than 4 kV/cm is used in order to provide cone-jet operation of the dispensing apparatus 19.

As used herein, nonuniform electric field refers to an electric field created by an electrical potential difference between two electrodes. The nonuniform electric field includes at least some electric field lines that are more locally concentrated at one electrode relative to the other electrode, e.g., more concentrated at the dispensing end 23 relative to the second electrode or a grounded object 15. In other words, for example, at least some of the field lines are off axis relative to the longitudinal axis 39 that extends through the center of the openings 27 and 29. For example, the grounded object 15 is positioned forward of dispensing end 23 and is of a size and/or includes at least a portion that is located at a position away from the longitudinal axis 39.

In various embodiments, the second electrode may also, or in the alternative, include one or more loop electrodes, plate electrodes, grounded surfaces, etc. The object 15 may still be coated even if a different electrode structure is used to produce the charged particles.

For example, a loop electrode 40 as shown in FIG. 1 may be positioned forward of the dispensing end 23 to create the electric field for providing highly charged particles in the defined volume 17 in which the object 15 is positioned. With the particles provided in the defined volume, the highly charged particles are moved toward a grounded object 15 as the loop electrode 40, at least in one embodiment is position in proximity to the surface of the object 15 to be coated. As such, it will be recognized that coating the object 15 using the electrospray coating system 10 shown generally in FIG. 1 may involve providing particles in a defined volume in which the object is provided, and thereafter, moving the particles toward the object forming a coating thereon. In addition, alternatively, the particles may be formed and moved toward the object for coating thereon simultaneously with their formation. For example, the object 15 may be grounded to set up the nonuniform electric field for producing the charged particles in the defined volume in which the object 15 is provided with the same field also providing for the movement of such charged particles towards the object 15 so as to form a coating thereon.

In one example embodiment, where the liquid spray composition includes an active ingredient, the liquid spray composition is flowed through the inner opening 27 of the nozzle structure 18 and the liquid diluent composition is flowed through the outer opening 29 of the nozzle structure 18. Generally, the resulting blended flow of the liquid compositions at the dispensing end 23 has an electrical conductivity associated therewith. In other words, as the liquid compositions progress through the openings, the potential difference between the first and second electrodes, which creates the electric field there between, strips the liquid of one polarity of charge, i.e., the negative charge is stripped when a high positive voltage is applied to the first electrode, leaving a positively charged microdroplet to be dispensed from the dispensing end 23. For example, the meniscus at the dispensing end 23 may form a cone-jet for dispensing a spray of microdroplets including the active ingredients when forces of a nonuniform field balance the surface tension of the meniscus. The spray of microdroplets further becomes more positive in the nonuniform electric field.

As the microdroplets evaporate, the charge of the microdroplets concentrates on the active ingredients resulting in a spray of charged coating particles. The amount of charge on the microdroplet, and thus the amount of charge on a particle after evaporation, is based at least upon the conductivity of the fluid composition used to spray the microdroplet, the surface tension of the fluid composition, the dielectric constant of the fluid composition, and the feed flow rate thereof.

At least in one embodiment, the electric charge concentrated on a particular particle is greater than about 30% of a maximum charge that can be held by the microdroplets, without the microdroplet being shattered or torn apart, i.e., greater than about 30% of the Rayleigh charge limit. At least in one another embodiment, the charge is greater than 50% of the Rayleigh charge limit. At 100%, the surface tension of the microdroplet is overcome by the electric forces causing droplet disintegration. The nonuniform electric field also provides for containment of particles and/or direction for the particles which would otherwise proceed in random directions due to the space charge effect.

One skilled in the art will recognize that the voltages applied may be reversed. For example, the first electrode may be grounded with a high positive voltage applied to the second electrode. In such a case, the particles would have a negative charge concentrated thereon. Further, any other applied voltage configuration providing a nonuniform electric field to establish the charged spray of coating particles may be used.

The nonuniform electric field can be provided by various configurations. For example, the second electrode may be any conductive material grounded (or having a suitable opposite charge applied thereto (i.e., opposite to the first electrode)) and positioned to establish the formation of a spray of coating particles 28 from the dispensing end 23 of the nozzle structure 18, e.g., the second electrode may be a grounded ring electrode, a grounded elongated element positioned in the interior volume of a stent structure, etc. The second electrode may also be located at various positions, such as just forward of the nozzle structure 18, or located farther away from the nozzle structure 18 and closer to object 15.

The strength of the field may be adjusted by adjustment of the distance between the first and second electrodes. Different field strengths may result in relatively different areas D upon which particle spray is provided, at least in part due to the space charge effect of the spray of particles 28. One skilled in the art will recognize that one or more components of the dispensing apparatus 19 may be moved relative to the others, e.g., the object 15 relative to the nozzle structure 18 or vice versa, to facilitate adjustment of field strength, and control one or more parameters according to the present invention to form a selected type of coating.

Further, the object 15 and/or the dispensing apparatus 19 (or any component thereof) may be moved in any one or more different directions as represented generally by the horizontal/vertical movement arrows 101 and radial movement arrow 102 prior to, during, or after the coating process for any particular reason. Such movement of the object 15 or any elements of the coating system 10 may be performed using any apparatus configured for the desired motion. The present invention is not limited to any particular structure for providing such movement. Further, the present invention is not limited to movement of any elements of the coating system 10 or the object 15 during the coating process. In other words, for example, the object 15, such as a medical device, may remain in a fixed position within the defined volume 17 as the coating process is performed.

The electrospray nozzle structure 18 used for particle generation as described herein is operable in a cone jet mode when an appropriate voltage is applied for creation of the nonuniform electric field. For example, FIGS. 2A-2C are images of a capillary electrospray dispensing end (e.g., nozzle spray head) progressing from the start of spray (FIG. 2A) to a "pulsating" mode (FIG. 2B) to a "cone-jet" mode (FIG. 2C) according to the present invention.

FIG. 2B shows a magnified view of the dispensing end (e.g., capillary tip) operating in pulsating mode and the meniscus of fluid is clearly visible. In FIG. 2C, the dispensing end is operating in the cone-jet mode where the electric field forces the composition being sprayed into a sharp point from which a nanofibril can be seen emerging therefrom. This fibril is unstable and breaks up into charged particles according to the present invention (e.g., a solvent carrier and solute). The solvent evaporates due to the extremely high surface area. FIG. 2D shows a graph indicating the current versus voltage curve for electrospray of a particular solution. Note that a particular voltage is needed for the nozzle to operate in cone jet mode and that such a voltage may need adjustment to maintain a stable cone-jet mode. A stable cone-jet mode of operation is of importance when applying a uniform selected type of coating to an object such as described herein.

As used herein, a stable cone-jet refers to a cone-jet that does not flutter between a cone-jet mode and a non-cone-jet mode (e.g., pulsating mode). Further, such a stable cone-jet may exhibit a dark tip appearance with no corona discharge being present.

As shown in FIG. 2C, a cone-jet 100 is formed at the dispensing end 23 of the nozzle structure 18. The cone-jet 100 extends from the dispensing end 23 to a point or tip 109, that, at least in one embodiment, lies on axis 39. An angle 104 is formed between the cone-jet 100 and a plane 106 lying orthogonal to axis 39 at the tip 109. When the angle 104 decreases such that it looks more like the meniscus of FIG. 2B, the cone-jet is more likely to move into a pulsating mode of operation. As such, by controlling the process to maintain a desired angle 104 of the cone-jet, a stable cone jet can be achieved according to the present invention as further described herein.

As used herein, coating refers to forming a layer or structure on a surface. The coated layer or structure formed on the surface may be a coating that adheres to an underlying layer or the surface 13, or a coating that does not adhere to the surface or an underlying layer. Any level of adherence to the surface 13 or an underlying layer is contemplated according to the present invention. For example, a coating formed on surface 13 of the object 15 may be formed as a sheath about a structure (e.g., a stent structure) without necessarily having adhesion between the layer and the structure.

Likewise, an adhesion layer may be deposited on an object 15 prior to forming a coating on the object 15 such that greater adhesion is accomplished. The adhesion layer may also be coated on the surface 13 of the object 15 employing methods and/or systems according to the present invention.

Various embodiments of the coating methods and systems described are suitable to allow one or more objects to be coated as a batch. However, the present invention is not limited to only coating objects such as medical devices in batches, i.e., coating a group of one or more devices in one batch process followed by coating a second group of one or more devices in a second batch process. The methods and systems of the present invention can be utilized to continuously run objects through the systems such that the process does not have to be started and stopped for coating the objects in batches. In other words, a plurality of objects such as medical devices can be coated through a continuous process.

In one or more of the embodiments of the present invention, single or multiple coatings can be applied to objects, separately or simultaneously. For example, a coating sprayed may include multiple materials, different nozzle structures may be provided with different source materials for controlling and spraying different coating materials, different nozzle structures may be controlled for use during different time periods so as to provide different layers of coating materials on at least a portion of the object, multiple layers may be sprayed using the same or different source materials (e.g., forming a somewhat laminated coating), the entire object or just a portion of the object may be coated (e.g., a charge could be applied to a portion of the surface to attract all of or a majority of the sprayed particles to the charged portion), different portions of the object may be sprayed with a thicker coating than the remainder of the object, and/or masking materials may be used to mask certain portions of the object from having coating applied thereto.

As indicated above, the present invention contemplates applying one layer or multiple layers of the same or different types of coating (e.g., an open matrix coating, a closed film coating, and an intermediate matrix coating, in any combination). Such layers may perform identical or different functions (e.g., to provide for biocompatibility, to control drug release, etc.). Further, the one or more layers may be applied to conductive or non-conductive surfaces.

The object 15 may be a medical device amenable to the coating processes described herein. The medical device, or portion of the medical device, to be coated or surface modified may be made of metal, polymers, ceramics, composites or combinations thereof, and for example, may be coated with one or more of these materials. For example, glass, plastic or ceramic surfaces may be coated. Further, the present invention may be used to form a coating on surfaces of other objects as well, e.g., metal substrates or any other surfaces that may be rendered conductive (e.g., whether flat, curved, or of any other shape).

Although the coatings described herein may be used to coat a vascular stent, other medical devices within the scope of the present invention include any medical devices such as those, for example, which are used, at least in part, to penetrate and/or be positioned within the body of a patient, such as, but clearly not limited to, those devices that are implanted within the body of a patient by surgical procedures. Examples of such medical devices include implantable devices such as catheters, needle injection catheters, blood clot filters, vascular grafts, stent grafts, biliary stents, colonic stents, bronchial/pulmonary stents, esophageal stents, ureteral stents, aneurysm filling coils and other coiled devices, reconstructive implants, trans myocardial revascularization ("TMR") devices, percutaneous myocardial revascularization ("PMR") devices, lead wires, implantable spheres, pumps, dental implants, etc., as are known in the art, as well as devices such as hypodermic needles, soft tissue clips, holding devices, and other types of medically useful needles and closures. Any exposed surface of these medical devices may be coated with the methods and systems of the present invention.

The source material held in the source holding apparatus 30 may be any source of material (e.g., such as coating materials described herein including solvents and active ingredients) which can be provided in the defined volume in particle form as described according to the present invention. In one or more embodiments, the source material in source holding apparatus 30 is a liquid spray composition that may include a solution, a suspension, a microsuspension, an emulsion, a microemulsion, a gel, a hydrosol, or any other liquid compositions that when provided according to the present invention results in the generation of particles.

In one embodiment according to the present invention, the liquid spray composition may include at least one of a biologically active ingredient, a polymer, and a solvent (e.g., a solvent suitable to at least partially dissolve the polymer). Further, for example, such liquid spray compositions may include a biologically active ingredient, a polymer, and a solvent suitable to at least partially dissolve the polymer.

As used herein, an active ingredient refers to any component that provides a useful function when provided in particle form, particularly when provided as nanoparticles. The present invention is particularly beneficial for spraying nanoparticles and also is particularly beneficial for spraying particles including biologically active ingredients.

As such, the term "active ingredient" refers to material which is compatible with and has an effect on the substrate or body with which it is used, such as, for example, drug active ingredients, chemical elements for forming nanostructures, materials for modifying local cell adherence to a device, materials for modifying tissue response to a device surface, materials for modifying systemic response to a device, materials for improving biocompatibility, and elements for film coatings, e.g., polymers, excipients, etc.

The term "biologically active ingredient" or "biologically active material or component" is a subset of active ingredient and refers to material which is compatible with and has an effect (which may, for example, be biological, chemical, or biochemical) on the animal or plant with which it is used and includes, for example, medicants such as medicines, pharmaceutical medicines, and veterinary medicines, vaccines, genetic materials such as polynucleic acids, cellular components, and other therapeutic agents and drugs, such as those described herein.

As used herein, the term particle, and as such nanoparticle, includes solid, partially solid, and gel-like droplets and microcapsules which incorporate solid, partially solid, gel-like or liquid matter. Particles provided and employed herein may have a nominal diameter as large as 10 micrometers.

As used herein, nanoparticle refers to a particle having a nominal diameter of less than 2000 nm. The present invention is particularly beneficial in spraying nanoparticles having a nominal diameter greater than 1 nanometer (nm), particles having a nominal diameter less than 1000 nm, particles having a nominal diameter of less than 500 nm, particles having a nominal diameter of less than 200 nm, and particles having a nominal diameter of less than 100 nm.

Further, the particles used for coating as described herein are, in at least one embodiment, monodisperse coating particles. As used herein, monodisperse coating particles are coating particles that have a geometrical standard deviation of less than 1.2. In other words, the standard deviation with respect to mean particle size of particles provided according to the present invention is, at least in one embodiment, less than or equal to 20%.

The coating materials used in conjunction with the present invention are any desired, suitable substances such as defined above with regard to active ingredients and biologically active ingredients. In some embodiments, the coating materials comprise therapeutic agents, applied to medical devices alone or in combination with solvents in which the therapeutic agents are at least partially soluble or dispersible or emulsified, and/or in combination with polymeric materials as solutions, dispersions, suspensions, lattices, etc. The terms "therapeutic agents" and "drugs", which fall within the biologically active ingredients classification described herein, are used interchangeably and include pharmaceutically active compounds, nucleic acids with and without carrier vectors such as lipids, compacting agents (such as histones), virus, polymers, proteins, and the like, with or without targeting sequences. The coating on the medical devices may provide for controlled release, which includes long-term or sustained release, of a bioactive material.

Specific examples of therapeutic or biologically active ingredients used in conjunction with the present invention include, for example, pharmaceutically active compounds, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a non-infectious vector or in a viral vector which may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic polymers that are selected from a number of types depending on the desired application. For example, biologically active solutes include anti-thrombogenic agents such as heparin, heparin derivatives, urokinase, and PPACK (dextrophenylalanine proline arginine chloromethylketone); prostaglandins, prostacyclins/prostacyclin analogs; antioxidants such as probucol and retinoic acid; angiogenic and anti-angiogenic agents; agents blocking smooth muscle cell proliferation such as rapamycin, sirolimus, everolimus, tacrolimus, pimecrolimus, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine, chemokine antagonists, chemokine receptor antagonists, inhibitors of tissue-necrosis factor and nuclear factor-kB and other proinflammatory cytokines; lipoxygenase inhibitors; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, colchicine, epothilones, endostatin, angiostatin, Squalamine, and thymidine kinase inhibitors; L-arginine, its derivatives and salts (e.g., arginine hydrochloride); antimicrobials such as triclosan, cephalosporins, aminoglycosides, and nitorfuirantoin; anesthetic agents such as lidocaine, bupivacaine, and ropivacaine; nitric oxide (NO) donors such as lisidomine, molsidomine, NO-protein adducts, NO-polysaccharide adducts, polymeric or oligomeric NO adducts or chemical complexes; anticoagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Wafarin sodium, Dicumarol, aspirin, prostaglandin inhibitors, cyclo-oxygenase inhibitors, non-steroidal anti-inflammatory drugs (NSAIDs), platelet inhibitors and tick antiplatelet factors; interleukins, interferons, and free radical scavengers; vascular cell growth promoters such as growth factors, growth factor receptor antagonists, transcriptional activators, and translational promoters; vascular cell growth inhibitors such as growth factor inhibitors (e.g., PDGF inhibitor—Trapidil), growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; Tyrosine kinase inhibitors, chymase inhibitors, e.g., Tranilast, ACE inhibitors, e.g., Enalapril, MMP inhibitors (e.g., Ilomastat, Metastat), GP IIb/IIIa inhibitors (e.g., Intergrilin, abciximab), seratonin antagonist, and 5-HT uptake inhibitors; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof; and beta blockers. In one or more embodiments, these and other components may be added to a liquid spray composition that includes a polymer and a solvent suitable for dissolving all or at least a part of the polymer in the composition.

Modifications to or various forms of the coating materials and/or additional coating materials for use in coating a medical device according to the present invention are contemplated herein as would be apparent to one skilled in the art. For example, such coating materials may be provided in derivatized form or as salts of compounds.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include, as a primary example, those proteins or polypeptides that can compensate for defective or deficient species in an animal, or those that act through toxic effects to limit or remove harmful cells from the body. In addition, the polypeptides or proteins that can be incorporated into the polymer coating, or whose DNA can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Coating materials other than therapeutic agents include, for example, polymeric materials, sugars, waxes, and fats, applied alone or in combination with therapeutic agents, and monomers that are cross-linked or polymerized. Such coating materials are applied in the form of, for example, powders, solutions, dispersions, suspensions, and/or emulsions of one or more polymers, optionally in aqueous and/or organic solvents and combinations thereof or optionally as liquid melts including no solvents.

When used with therapeutic agents, the polymeric materials are optionally applied simultaneously with, or in sequence to (either before or after), the therapeutic agents. Such polymeric materials employed as, for example, primer layers for enhancing subsequent coating applications (e.g., application of alkanethiols or sulfhydryl-group containing coating solutions to gold-plated devices to enhance adhesion of subsequent layers), layers to control the release of therapeutic agents (e.g., barrier diffusion polymers to sustain the release of therapeutic agents, such as hydrophobic polymers; thermal responsive polymers; pH-responsive polymers such as cellulose acetate phthalate or acrylate-based polymers, hydroxypropyl methylcellulose phthalate, and polyvinyl acetate phthalate), protective layers for underlying drug layers (e.g., impermeable sealant polymers such as ethylcellulose), biodegradable layers, biocompatible layers (e.g., layers comprising albumin or heparin as blood compatible biopolymers, with or without other hydrophilic biocompatible materials of synthetic or natural origin such as dextrans, cyclodextrins, polyethylene oxide, and polyvinyl pyrrolidone), layers to facilitate device delivery (e.g., hydrophobic polymers, such as an arborescent polyisobutylene copolymer, or hydrophilic polymers, such as polyvinyl pyrrolidone, polyvinyl alcohol, polyalkylene glycol (i.e., for example, polyethylene glycol), or acrylate-based polymer/copolymer compositions to provide lubricious hydrophilic surfaces), drug matrix layers (i.e., layers that adhere to the medical device and have therapeutic agent incorporated therein or thereon for subsequent release into the body), and epoxies.

When used as a drug matrix layer for localized drug delivery, the polymer component of the coatings may include any material capable of absorbing, adsorbing, entrapping, or otherwise holding the therapeutic agent to be delivered. The material is, for example, hydrophilic, hydrophobic, and/or biodegradable, and is preferably selected from the group consisting of polycarboxylic acids, cellulosic polymers, gelatin, polyvinylpyrrolidone, maleic anhydride polymers, polyamides, polyvinyl alcohols, polyethylene oxides, glycosaminoglycans, polysaccharides, polyesters, polyurethanes, silicones, polyurea, polyacrylate, polyacrylic acid and copolymers, polyorthoesters, polyanhydrides such as maleic anhydride, polycarbonates, polyethylene, polypropylenes, polylactic acids, polystyrene, natural and synthetic rubbers and elastomers such as polyisobutylene (PIB), polyisoprene, polybutadiene, including elastomeric copolymers, such as Kraton®, styrene-isobutylene-styrene (SIBS) copolymers; polyglycolic acids, polycaprolactones, polyhydroxybutyrate valerates, polyacrylamides, polyethers, polysaccharides such as cellulose, starch, dextran and alginates; polypeptides and proteins including gelatin, collagen, albumin, fibrin; copolymers of vinyl monomers such as ethylene vinyl acetate (EVA), polyvinyl ethers, polyvinyl aromatics; other materials such as cyclodextrins, hyaluronic acid and phosphoryl-cholines; and mixtures and copolymers thereof. Coatings from polymer dispersions such as polyurethane dispersions (BAYHYDROL, etc.) and acrylic latex dispersions are also within the scope of the present invention. Preferred polymers include polyurethanes; polyacrylic acid as described in U.S. Pat. No. 5,091,205; and aqueous coating compositions comprising an aqueous dispersion or emulsion of a polymer having organic acid functional groups and a poly-functional crosslinking agent having functional groups capable of reacting with organic acid groups, as described in U.S. Pat. No. 5,702,754. Other polymers that may be used include poly(DL-lactide-co-ε-caprolactone, 80/20) (PLCL), Chronoflex AR (CFR) which is polyurethane 22% solid in dimethylacetamide, and poly(tetrahydrofurfuryl methacrylate-co-ethyl methacrylate) PTHFMA-EM, poly-ethylene-co-vinyl acetate (PEVA), and poly-n-butyl methacrylate (PNBA).

One or more solvents may be used as part of the liquid spray composition to fully or partially dissolve one or more polymers thereof. Such solvents may range from polar solvents (e.g., acetone and methanol) to non-polar solvents (e.g., chloroform and toluene).

Polar solvents, as used herein, are liquids that tend to have higher dielectric constants, where the higher the dielectric constant, the greater the relative polarity. Such polar solvents may include, for example, but are not limited to, water, methanol, ethanol, isopropanol, acetonitrile, acetone, and tetrahydrofuran.

Non-polar solvents, as used herein, are liquids that tend to have lower dielectric constants than polar solvents, where the lower the dielectric constant, the lower the relative polarity. Such non-polar solvents may include, for example, but are clearly not limited to, toluene, chloroform, hexane, and dichloromethane.

In one or more embodiments herein, particularly where an open matrix coating is desired, high dielectric constant solvents may be used. Such high dielectric constant solvents include solvents having a dielectric constant equal to or greater than 10. For example, high dielectric constant solvents include water (dielectric constant of 80), methanol (dielectric constant of 33), ethanol (dielectric constant of 24), or acetone (dielectric constant of 21).

In one or more other embodiments, low dielectric constant solvents may be used. Such low dielectric constant solvents include solvents having a dielectric constant less than 10. One will recognize that some polar solvents, such as tetrahydrofuran, are low dielectric constant solvents even though they are polar solvents. For example, low dielectric constant solvents include tetrahydrofuran (dielectric constant of 7.5), chloroform (dielectric constant of 4.8), or toluene (dielectric constant of 2.4).

The release rate of drugs from drug matrix layers is largely controlled, for example, by variations in the polymer structure and formulation, the diffusion coefficient of the matrix, the solvent composition, the ratio of drug to polymer, potential chemical reactions and interactions between drug and polymer, the thickness of the drug adhesion layers and any barrier layers, and the process parameters, e.g., drying, etc. The coating(s) applied by the methods and apparatuses of the present invention may allow for a controlled release rate of a coating substance with the controlled release rate including both long-term and/or sustained release.

The source material held in the source holding apparatus 32 may be any liquid diluent composition which when provided in combination with the liquid spray composition at the dispensing end 23 of the nozzle structure results in coating particles being provided in the defined volume in particle form as described according to the present invention herein. The source material in source holding apparatus 32 is a liquid diluent composition that includes at least one of a polar or non-polar solvent as described herein.

At least in one embodiment, the liquid diluent composition includes one or more high dielectric constant solvents. Further, at least in one embodiment, the liquid diluent composition has a high dielectric constant (i.e., a dielectric constant that is equal to or greater than 10). For example, the liquid diluent composition may include a high dielectric constant solvent and include a low dielectric constant solvent (e.g., mixed solvents), yet still the liquid diluent composition may have a high dielectric constant.

Further, when the liquid diluent composition has a high dielectric constant, the liquid diluent composition may further include an active ingredient, such as a polymer or a drug. Further, at least in another embodiment, the liquid diluent composition is a high dielectric constant composition and includes a biologically active ingredient (i.e., without a polymer).

Further, at least in one embodiment, the liquid diluent composition has a weight concentration of active ingredient that is less than 1 percent of the total weight concentration of the liquid diluent composition (e.g., a biologically active ingredient that is less than 1 percent of total weight concentration). Further, in another embodiment, the liquid diluent composition has a weight concentration of active ingredient that is less than 0.5 percent of the total weight concentration of the liquid diluent composition.

Still further, in one embodiment, the liquid diluent composition may further include an additive that is used to control conductivity of the liquid diluent composition. For example, the additive used to control conductivity may include a buffer solution such as a phosphate buffer (e.g., for spraying particles including peptides), an acid such as nitric acid, or a salt such as ammonium chloride. Generally, with use of a low dielectric constant solvent, an additive to increase the conductivity of the liquid diluent composition is needed to apply an open matrix coating.

Still further, at least in one embodiment, the liquid diluent composition includes only solvents and has a high dielectric constant (e.g., includes at least one high dielectric constant solvent. With use of only solvents in the liquid diluent composition, fouling of the spray tip is less likely.

The coatings of the present invention are applied such that they result in a suitable thickness, depending on the coating material and the purpose for which the coating or coatings are applied. For example, coatings applied for localized drug delivery are typically applied to a thickness of at least about 1 micron and not greater than 30 microns. In one embodiment, the thickness is greater than 2 microns. Further, in another embodiment, the thickness is not greater than 20 microns. In addition, very thin coatings such as those as thin as 100 Angstroms may be provided. Much thicker coatings of more than 30 microns are also possible.

Figure 7A:
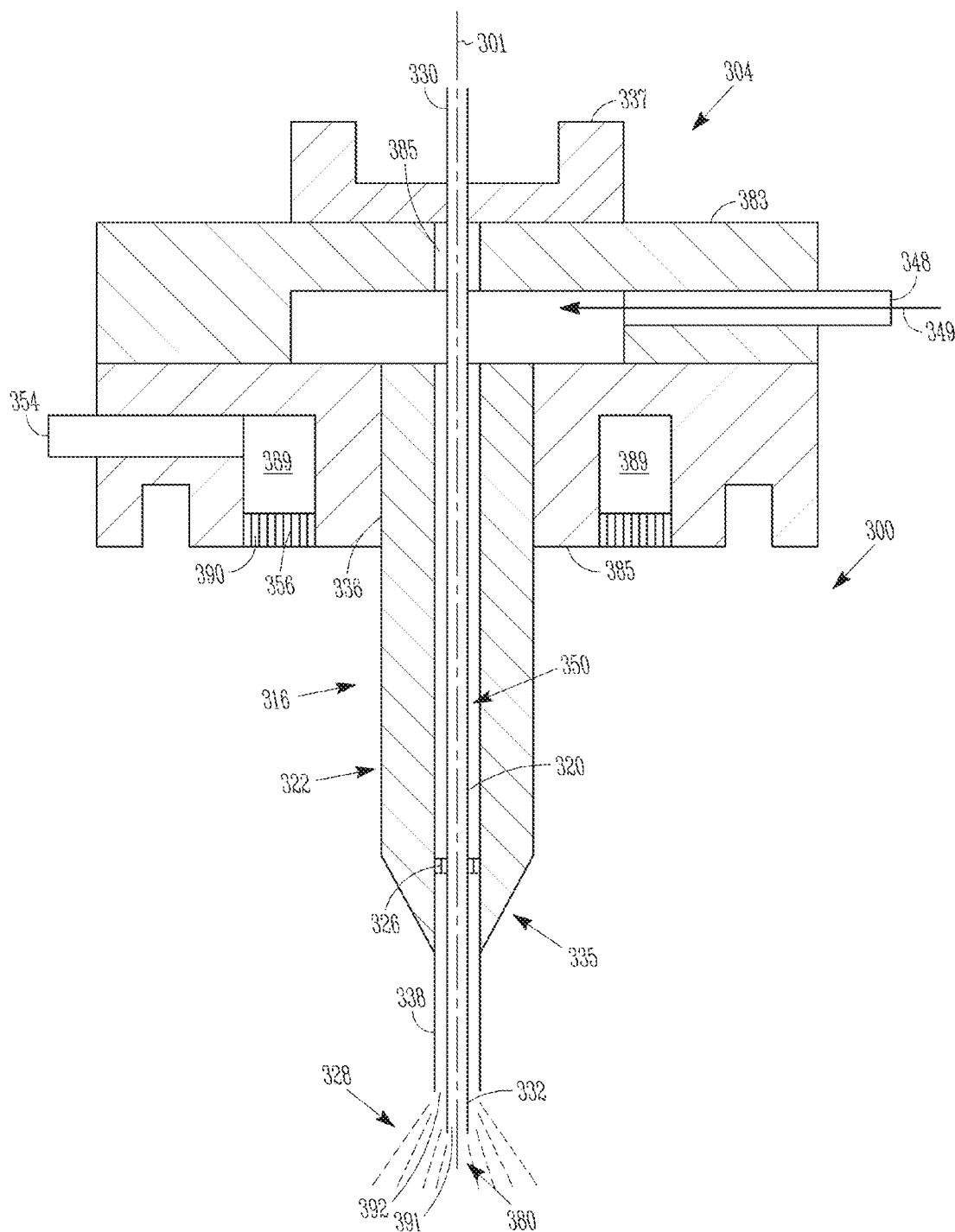
FIG. 7A shows a more detailed diagram of one embodiment of a dual opening electrospray dispensing apparatus according to the present invention that may be controlled for applying one or more of the types of coatings such as generally shown in FIGS. 3A-3C.

Several detailed configurations for the dispensing device 19 are described in further detail herein. For example, FIG. 7A is a more detailed diagram of one configuration of a portion 300 of an electrospraying apparatus such as shown generally in FIG. 1 including a dual concentric opening dispensing device 314 extending along axis 301 according to the present invention from a first end 304 to a second end or dispensing end 380. First end 304 may be formed of conductive portions to facilitate application of voltages or ground to capillary tube 320.

The first end 304 includes a distributor head 316 that is coincident with axis 301 for use in establishing the spray of particles. The distributor head 316 includes capillary tube 320 having an axis therethrough coincident with axis 301. The capillary tube 320 includes a first end 330 sealingly positioned in aperture 385 of the first end 304 by conductive sealing element 337 at the upper surface 383 of the first end 304. The capillary tube 320 further includes a second end 332 positioned for providing a liquid spray composition to the dispensing end 380 (i.e., through an inner opening 391 that terminates at the dispensing end 380 for use in generating the spray of particles as desired). The capillary tube 320 may be made of any suitable material, such as, for example, platinum, silica, stainless steel, etc. and may be of any suitable size. For example, the capillary tube may, at least in one embodiment, have an outer diameter in the range of about 8 µm to about 2.5 mm, and an inner diameter in the range of about 6 µm to about 2 mm. Further, in another embodiment, the inner diameter of the capillary tube is in the range of about 10 µm to about 200 µm.

Further, the distributor head 316 includes a nozzle portion or casing 322 which as illustrated in FIG. 7A is an elongate substantially cylindrical metal casing concentric with the capillary tube 320 for providing an outer opening 392 concentric with inner opening 390 for providing liquid diluent compositions to the dispensing end 380. However, the casing 322 can be conductive or nonconductive. Together, in this particular embodiment, the capillary tube 320 and the casing 322 form the dual opening capillary tube electrode of the distributor head 316 for use in providing the spray of particles when operating in a cone-jet mode. The casing or nozzle portion 322 includes a first end portion 336 which tapers at section 335 thereof to a narrower second end portion 338. The second end portion 338 extends from the tapered section 335 and is concentric with the second end 332 of the capillary tube 320. The narrow end of the tapered section 335 extends a distance of about 5 mm to about 5 cm from the lower surface 385 of the first end 304. The outer diameter of the second end portion 338 is in the range of about 2 mm to about 5 mm and the inner diameter of the second end portion 338 is in the range of about 0.1 cm to about 0.2 cm. The second end 332 of the capillary tube 320 extends beyond the second end portion of the metal casing or nozzle portion 322 towards the target surface to be coated by a distance of about 2 mm to about 5 mm. The nozzle portion 322 is formed of any suitable metal or nonconductive material such as stainless steel, brass, alumina, or any other suitable material. The nozzle portion 322 is spaced from the capillary tube 320 by spacers 326 or other spacing structures. For example, a metal casing 322 may be deformed at particular portions, such as pin points or depressions, to create a neck for centering the capillary tube 320 therein. An inlet 348 is configured for directing the liquid diluent composition 349 in aperture or opening 392 between the concentric capillary tube 320 and the nozzle portion 322. One will recognize the capillary tube electrode may take one of many configurations.

A gas inlet 354 is provided in the first end 304 to allow for input of a stream of electro-negative gases, e.g., $CO_2$, $SF_6$, etc., to form a gas sheath about the capillary tube 320 or flood the region about dispensing end 380. This gas sheath allows the applied voltage to be raised to higher levels without corona discharge, e.g., the electrostatic breakdown voltage for the capillary tube electrode is increased. The entire portion of end 304 or portions thereof may be formed of conductive materials to facilitate application of a voltage or ground to the capillary tube electrode. For example, sealing elements 337 may be nonconductive, but in one embodiment are conductive to facilitate application of a voltage or ground to capillary tube 320. Further, in one or more embodiments, generally, the region around the capillary tube 320 and the nozzle portion 322 is flooded with a gas through the port 354 to increase the electrostatic breakdown voltage for the capillary tube electrode. In one embodiment, a chamber in which the coating process is being completed is flooded with the gas through the port 354 and then a flow in the range of about 5 cc/min to about 200 cc/min is continued through the port 354.

To establish the spray of particles from the dual opening dispensing device 314, a first flow of a liquid spray composition is received in the first end 330 of the capillary tube 320 and flows through opening 391. For example, the flow rate of the liquid spray composition may be greater than about 0.01 μl/min or less than about 10 μl/min; or further may be less than about 5 μl/min, or even less than about 3 μl/min. Further, a second flow of a liquid diluent composition 349 is received in the port 348 of the nozzle and provided to opening 392. For example, the flow rate of the liquid diluent composition may be greater than about 0.01 μl/min or less than about 10 μl/min; or further may be less than about 5 μl/min.

In one embodiment, a relatively high voltage, for example, in the range of about 2000 volts to about 6000 volts, may be applied between the object being coated and the capillary tube 320 to establish the potential difference between the first and second electrode of the spraying apparatus and cause operation in cone-jet mode. In this particular illustrative configuration, capillary tube 320, metal casing 322, and sealing element 337 are conductive. Spray 328 is established forward of the dispensing tip 380 of the second end 332 of the capillary tube 320 per a mode of operation as previously described. The potential difference between the electrodes establishes an electric field there between, causing operation in a cone-jet mode for generation of coating particles according to the present invention.

The electrospray coating system 10 illustrated and described generally herein with reference to FIG. 1 can be controlled to provide for particular types of selected coatings according to the present invention. For example, one or more different parameters of the system 10 may be controlled so as to form an open matrix coating as opposed to a closed film coating.

According to one or more embodiments of the present invention, the coating process using one or more controlled parameters as described herein allows for applying nanocomposite coatings onto objects such as coronary stents and/or other medical devices. The cone-jet mode of operation produces highly charged, uniform, monodisperse nanoparticles comprised of one or more components that are used to coat the object. Non-line-of-sight coating can be achieved (i.e., coating of surfaces not directly in the line of sight of the dispensing end 23, such as the interior surface of a stent). The coating particles in such non-line-of-sight coating are directed to the surface of the object being coated by the established electrical field, which aids in the uniform coating of objects with intricate architecture. Use of the dual opening nozzle structure (e.g., a dual-capillary spray head) permits two liquid streams of materials to be mixed at the spray tip or dispensing end 23, which enables the application of multiple agents in a nanocomposite open matrix coating and the co-spraying of materials which are otherwise incompatible. The electrospray process can accommodate a range of polymers and solvents that are used or likely to be used in coating objects such as stents.

In at least one embodiment, solvents required to dissolve a polymer (e.g., poly(isobutylene), poly(styrene-b-isobutylene-b-styrene, etc.) to be sprayed are low dielectric constant non-polar solvents (e.g., toluene) or are low dielectric constant polar solvents (tetrahydrofuran) and not easily amenable to electrospray. However, using the following techniques including, for example, adding a higher dielectric constant solvent such as methanol in the inner or in the outer capillary liquid stream, as further described herein, a liquid spray composition that includes such a hard to spray dissolved polymer can be used to coat an object.

Generally, one or more control parameters may be useful in selecting a type of coating to be formed on the object 15. Such control parameters which shall be discussed in further detail herein include controlling a flow rate of the second flow of the liquid diluent composition in the outer opening 29 relative to a flow rate of the first flow of the liquid spray composition in the inner opening 27 (e.g., controlling the ratio of the flow of the liquid diluent composition to the total flow of the liquid spray composition and liquid diluent composition dispensed at the dispensing end 23), selecting a particular liquid diluent composition to be provided in the outer opening 29 (e.g., selecting a particular liquid diluent composition having a particular conductivity); and controlling the evaporation process of the microdroplets dispensed from the dispensing end 23 of the nozzle structure 18.

The relative flow rate of the second flow of the liquid diluent composition in the outer opening 29 to the flow rate of the first flow of the liquid spray composition in inner opening 27 can be selected to achieve a desired coating described herein. For example, selection of a higher ratio of flow rate for the liquid diluent composition relative to the total flow rate of the liquid spray composition and liquid diluent composition dispensed at the dispensing end 23, may result in the formation of a closed film coating.

As would be recognized, the ratio necessary to achieve a desired selected coating may depend on the compositions being used. However, generally, according to the present invention as the flow rate of the liquid diluent composition in the outer opening 29 exceeds 5 times the flow rate of the liquid spray composition in the inner opening 17, a closed film coating occurs. In other words, as the ratio of flow rate for the liquid diluent composition at the outer opening 29 relative to the total flow rate of the liquid spray composition and liquid diluent composition dispensed at the dispensing end 23 gets closer to 1, a closed film coating is achieved. As such, a user with the desired compositions known, can adjust the flow rates to achieve a selected type of coating by controlling the flow rate of the second flow of the liquid diluent composition in the outer opening 29 relative to the flow rate of the first flow of the liquid spray composition in inner opening 27.

Selecting a particular liquid diluent composition to be provided in the outer opening 29 can also be used to achieve a desired coating described herein. For example, selecting a liquid diluent composition that includes one or more high dielectric constant solvents (e.g., such as a liquid diluent composition that includes at least one of acetone or methanol (both higher dielectric constant solvents)) such that the liquid diluent composition has a high dielectric constant is likely to result in an open matrix coating. Likewise, selecting a liquid diluent composition that includes one or more low dielectric constant solvents (e.g., such as a liquid diluent composition that includes at least one of chloroform, toluene, or tetrahydrofuran (all low dielectric constant solvents)) such that the liquid diluent composition has a low dielectric constant is likely to result in a closed film coating.

In other words, selecting a liquid diluent composition for the outer opening that has a certain dielectric constant can be used to achieve a particular selected coating. For example, liquid diluent compositions that have a high dielectric constant (i.e., greater than 10) are typically required to obtain an open matrix coating.

Yet further, at least in one embodiment, selecting a particular high dielectric constant solvent for use in the liquid spray composition to be provided in the inner opening 27 may also be used to achieve a desired coating described herein. For example, selecting a solvent for use in the liquid spray composition that includes one or more high dielectric constant solvents (e.g., such as a liquid diluent composition that includes at least one of acetone or methanol (both higher dielectric constant solvents)) may be beneficial in providing an open matrix coating. For example, such a high dielectric constant solvent may be added to a low dielectric constant solvent that is required to dissolve a particular polymer to provide the ability to apply an open matrix coating (e.g., making the dielectric constant of the liquid spray composition higher).

Yet further, increasing the conductivity of the second flow of the liquid diluent composition is useful for achieving an open matrix coating on the at least one surface of the object 15. Such conductivity may be achieved by selecting, at least in one embodiment, a liquid diluent composition that has a conductivity greater than 1 $\mu S\ cm^{-1}$ (microSiemen/cm). In another embodiment, a liquid diluent composition that has a conductivity greater than 6.8 $\mu S\ cm^{-1}$ is beneficial in forming an open matrix coating.

Use of a liquid diluent composition that has a conductivity greater than 1 $\mu S\ cm^{-1}$, or even greater than 6.8 $\mu S\ cm^{-1}$, provides for substantially round particles being formed in the open matrix coating. Such substantially round particles are shown in FIG. 10c,d,g,h, as opposed to elongated fiber particles shown in FIGS. 10a,b,e,f. The substantially round particles are a direct result of using a high conductivity liquid diluent composition in the outer opening.

The conductivity of the liquid diluent composition can be manipulated using any known techniques. The liquid diluent composition may include a single component having a relatively high conductivity or a relatively high conductivity component may be added to a relatively low conductivity component. For example, an acid (e.g., nitric acid) or a salt (e.g., ammonium chloride) may be used to increase the conductivity of certain types of solvents (e.g., acetone, methanol, or water) that are desired for use as part of the liquid diluent composition.

At least in one embodiment, a lower conductivity liquid spray composition is provided at the inner opening 27. For example, the conductivity of the liquid spray composition (e.g., including de-ionized water and toluene) may be in the range of about 0.3 $\mu S\ cm^{-1}$ to about 1.0 $\mu S\ cm^{-1}$. In such a case, a liquid diluent composition (e.g., such as that including nitric acid) having a conductivity in the range of about 100 $\mu S\ cm^{-1}$ to about 1000 $\mu S\ cm^{-1}$ may be necessary to facilitate breakup of the inner stream of liquid spray composition so as to spray the coating particles.

At least in one embodiment, the liquid spray composition includes at least a biologically active material and a polymer. For example, in one or more embodiments, the ratio of weight concentrations of polymer to biologically active material (e.g., polymer:dexamethasone) may be as high as 10:1 or as low as 5:1. However, even lower ratios may be sprayed. Further, in one or more other embodiments of the liquid spray composition, the weight concentration of the active ingredient (e.g., the polymer or the polymer and biologically active ingredient) may be less than 5 percent of the total weight of the liquid spray composition, and may be less than 1 percent of the total weight concentration of the liquid spray concentration.

Further, the evaporation process of the microdroplets dispensed from the dispensing end 23 of the nozzle structure 18 may be controlled to achieve a particular selected coating. For example, the time allowed for evaporation of the microdroplets may be controlled as a function of selected type of coating to be applied.

In one embodiment, the time allowed for evaporation of the microdroplets before they reach the object 15 to form a coating thereon is increased so that an open matrix coating can be formed. For example, as shown in FIG. 4, a dual opening nozzle structure 120 is shown that has a dispensing end 122. The distance between the dispensing end 122 of the nozzle structure 120 and the surface 13 of the object 15 to be coated is controlled depending on the selected type of coating to be applied. For example, the distance d between the dispensing end 122 of the nozzle structure 120 and the surface 13 of the object 15 may be increased upon selection of an open matrix coating to allow more time of flight for evaporation of the microdroplets or decreased upon selection of a closed film coating to allow less time for evaporation. As would be recognized, either the nozzle structure 120 or the object 15 may be moved to adjust the distance d.

As described above, as the microdroplets evaporate, the charge of the microdroplets concentrates on the active ingredients resulting in a spray of charged particles. In one embodiment, the coating system 10 is configured such that prior to contact with the at least one surface 13 of the object 15, the weight percent of solvent in the evaporated microdroplet is less than 85% (e.g., corresponding to a weight percent of 15% polymer in a droplet that only includes only polymer solids and the solvent). At least in one embodiment, some solvent component forms a part of the particle volume as the particle contacts the surface 13 of the object 15. With some solvent component being a part of the residual particle volume occupied by the evaporated microdroplet, adhesion of the microdroplet (including the particle) to the surface 13 of the object 15 may be enhanced. After the microdroplet has contacted the surface 13 of the object 15, the remainder portion of the solvent evaporates, leaving the particle coated on the surface 13 of the object 15.

Generally, at least in one embodiment, an open matrix coating is facilitated by solvent evaporation such that the residual solvent immediately prior to contact with the at least one surface 13 of the object 15 is less than 85% by weight of the evaporated microdroplet. However, the relative composition of solvent:polymer in the particle that promotes open matrix formation may be different depending on the polymer used. But, generally, at least in one embodiment, an open matrix coating would be facilitated by solvent evaporation such that the residual solvent prior to contact with the at least one surface 13 of the object 15 is less than 80% by weight of the evaporated microdroplet. Likewise, generally, at least in one embodiment, a closed film coating would be facilitated by solvent evaporation such that the residual solvent immediately prior to contact with the at least one surface 13 of the object 15 is more than 90% by weight of the evaporated microdroplet. It will be apparent to one skilled in the art that the relative percentages of solvent and polymer that are given may vary according to the characteristics of the specific polymer that is used.

The amount of evaporation prior to the microdroplet/particle contacting the surface 13 of the object 15 may be controlled in a number of different ways for applying one or more different selected types of coatings, in addition to selecting a distance d as shown in FIG. 4. For example, the evaporation may be controlled by the type of solvent used, the temperature and pressure of a chamber in which the medical device is provided, the size of the microdroplet, the humidity, etc.

For example, maintaining a temperature in the defined volume in the range of 20 degrees centigrade to 30 degrees centigrade may be necessary upon selection of an open matrix coating. The temperature typically should not exceed the glass transition temperature for a given polymer.

Further, in one embodiment, maintaining humidity in the defined volume 17 to less than 20 percent RH assists in maintaining stability of the coating process. Controlling relative humidity prevents arcing or corona discharge. If the relative humidity is kept lower, higher voltages can be used before corona discharge becomes a problem, facilitating the cone-jet formation and maintenance.

As shown in FIG. 5, evaporation may also be controlled by providing a gas stream 130 in proximity to the cone-jet formed at the dispensing end 134 of a nozzle structure 132. As stream of gas along side the nozzle structure 132 may be provided, or the defined volume may be flooded with a gas. For example, one or more gases such as nitrogen or carbon dioxide may be used to increase evaporation. As such, with increased evaporation, achieving an open matrix coating is more likely. Yet further, providing the gas stream may assist in keeping the cone-jet stable (e.g., provide anti-fouling of the dispensing end 23). Still further, the gas stream should not generate turbulence around the cone jet, as this could cause instability thereof.

As previously mentioned, as the microdroplets evaporate and charge is concentrated on the particles, the nonuniform electric field provides for containment of particles and/or direction for the particles which would otherwise proceed in random directions due to the space charge effect; the space charge effect being necessary to provision of monodisperse and nonconglomerated particles. The space charge effect is generally dependent upon the size of the particles and the charge thereon. With the electric field being utilized to move the particles towards the object 15 and preventing them from scattering to other locations, the amount of coating material necessary to coat the object 15 is substantially reduced.

The loop electrode 40 as shown in FIG. 4 can also be used to prevent scattering and decrease the amount of coating material necessary to coat the object 15. For example, the loop electrode 40 can be used to establish the nonuniform electric field when positioned along a plane generally orthogonal to an axis 128 along which the nozzle structure 120 extends. The position, size and shape of the loop can be used to control the direction of the coating particles so as to coat the desired surfaces of the object 15. Generally, the loop 40 may be provided at a distance 126 that is about 1 mm from the target object 15 or may be further away from the target object. For example, the loop may be as far from the target as possible but still capable of generating the desired non-uniform electric field. For example, the loop 40 may lie in approximately the same plane as the tip of the nozzle structure (e.g., orthogonal to the axis along which the nozzle structure extends).

Yet further, one or more process techniques may be implemented to maintain a stable cone-jet during operation of the coating process so as to achieve the selected type of coating. For example, such techniques may include adjusting the voltage between the dispensing end of the nozzle structure 18 and the object 15 being coated as the thickness of the selected type of coating increases so as to maintain a stable cone jet at the dispensing end 23 of the nozzle structure 18 and/or monitoring at least one characteristic associated with the cone-jet to determine the stability of the cone-jet based thereon, and thereafter adjusting one or more process parameters to maintain a stable cone-jet.

When the thickness of the selected type of coating 105 increases on the object 15, the cone-jet may become unstable. For example, as the coating thickness increases, the electrical potential between the first and second electrode of the system 10 may no longer be sufficient to continue cone-jet mode operation. As such, adjusting the voltage between the dispensing end 23 of nozzle structure 18 and the object 15 being coated may be needed to maintain a stable cone-jet at the dispensing end of the nozzle structure 18. The adjustment of the voltage may be done manually by a user or may be performed automatically as a function of one or more characteristics of the cone-jet as described further herein.

For example, as illustratively shown in FIG. 1, a detection apparatus 50 (e.g., an imaging apparatus) may be used to detect at least one characteristic associated with the cone-jet (e.g., shift in angle 104 as shown in FIG. 2C). The stability of the cone-jet may then be determined based on the at least one characteristic and one or more process parameters may be adjusted accordingly to maintain a stable cone-jet. In other words, at least in one embodiment, an imaging apparatus may be used to detect the angle 104 as shown in FIG. 2C associated with the cone-jet. Depending on the desired angle 104 for maintaining stability, control apparatus 55 may determine that the cone-jet is on the verge of instability (e.g., due to increased thickness of the coating 105 being formed on the object 15). Upon such a determination, the electrical potential between the dispensing end 23 and the object 15 may be increased to maintain stable cone-jet operation.

Yet further, other characteristics associated with the cone-jet may be monitored. For example, the detection apparatus 50 may detect one or more flutters in the cone-jet (e.g., the cone-jet going into pulsating mode temporarily from cone-jet mode). Further, the detection apparatus may use imaging of the cone-jet to detect bubbles in at least one of the liquid flows being provided thereto. If bubbles are detected or flutters are detected, one or more various actions may be taken. For example, the flow of liquid to the nozzle may be modified, the flow may be interrupted to prevent sputtering on the surface of the target, and/or the voltage may be adjusted to eliminate the instability of the cone-jet.

Figure 6:
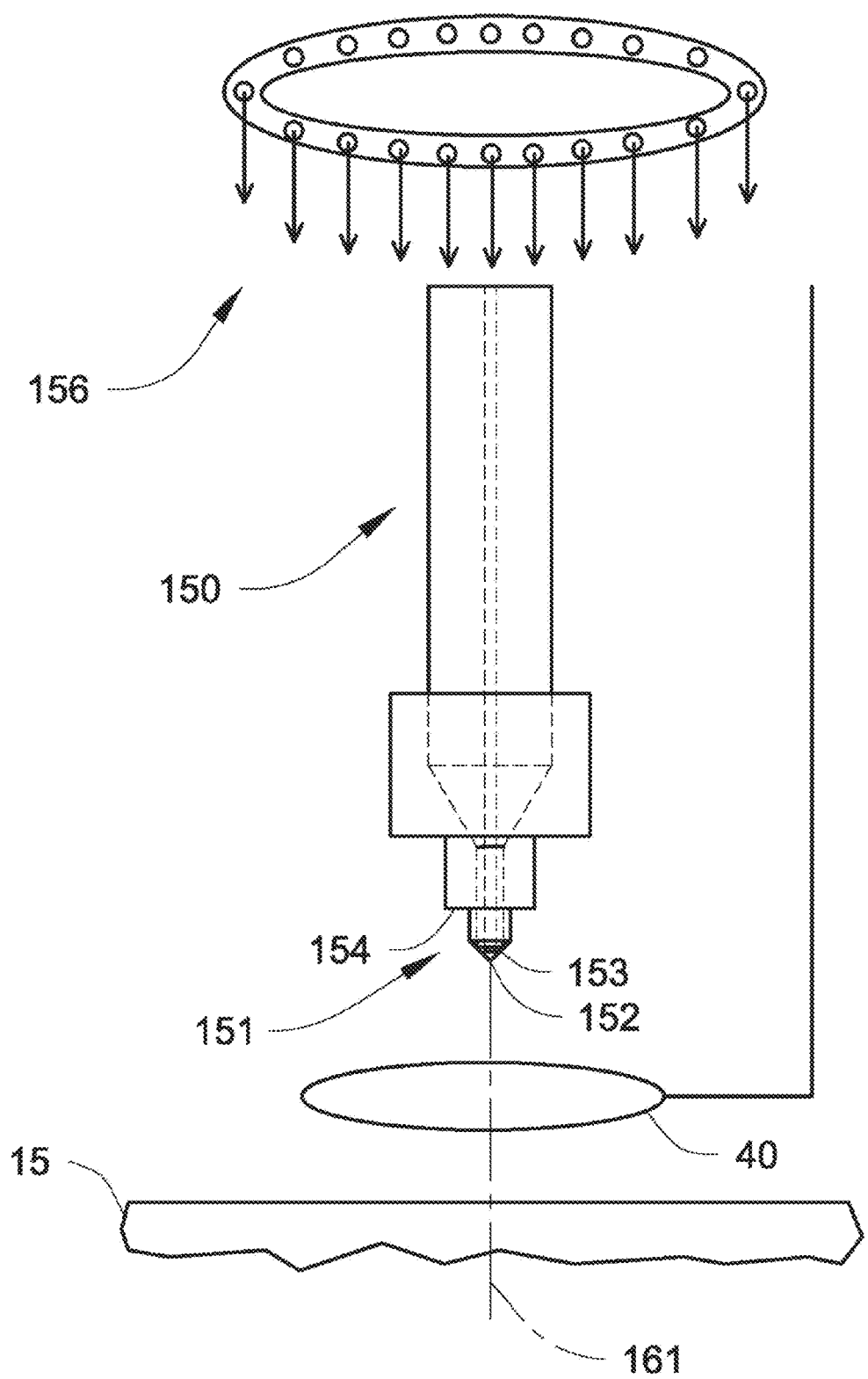
FIG. 6 shows a general diagrammatical illustration of one embodiment of an electrospray dispensing device that includes a triple opening nozzle in accordance with the present invention, and further includes a ring electrode for controlling particle spread as well as a gas flow for use in controlling the application of one or more of the types of coatings such as generally shown in FIGS. 3A-3C.

One will recognize that more than two concentric openings may be provided which terminate at the dispensing end 23 of the nozzle structure 18 (e.g., to provide more than two flows of compositions at the dispensing end). For example, although any suitable number of openings may be used, FIG. 6 shows a nozzle structure 150 that includes three concentric openings that terminate at the dispensing end 151 and which lie along axis 161. One will recognize that the termination of such openings can be displaced from one another along the axis 161 but must be in close proximity to allow the cone-jet to form from all compositions provided at the termination of such openings.

As shown in FIG. 6, inner opening 152 is provided along axis 161, and outer opening 154 is formed concentric therewith. An intermediate opening 153 is provided therebetween. At least in one embodiment, a biologically active material is provided in a liquid composition to the inner opening 152, a polymer at least partially dissolved in a solvent is provided to the intermediate opening 153, and a liquid diluent composition is provide to the outer opening 154. In cone-jet operation, a spray of coated particles is formed for coating an object 15.

For example, at least in one embodiment, the coated particles may include biologically active material encapsulated by the polymer.

Figure 7B:
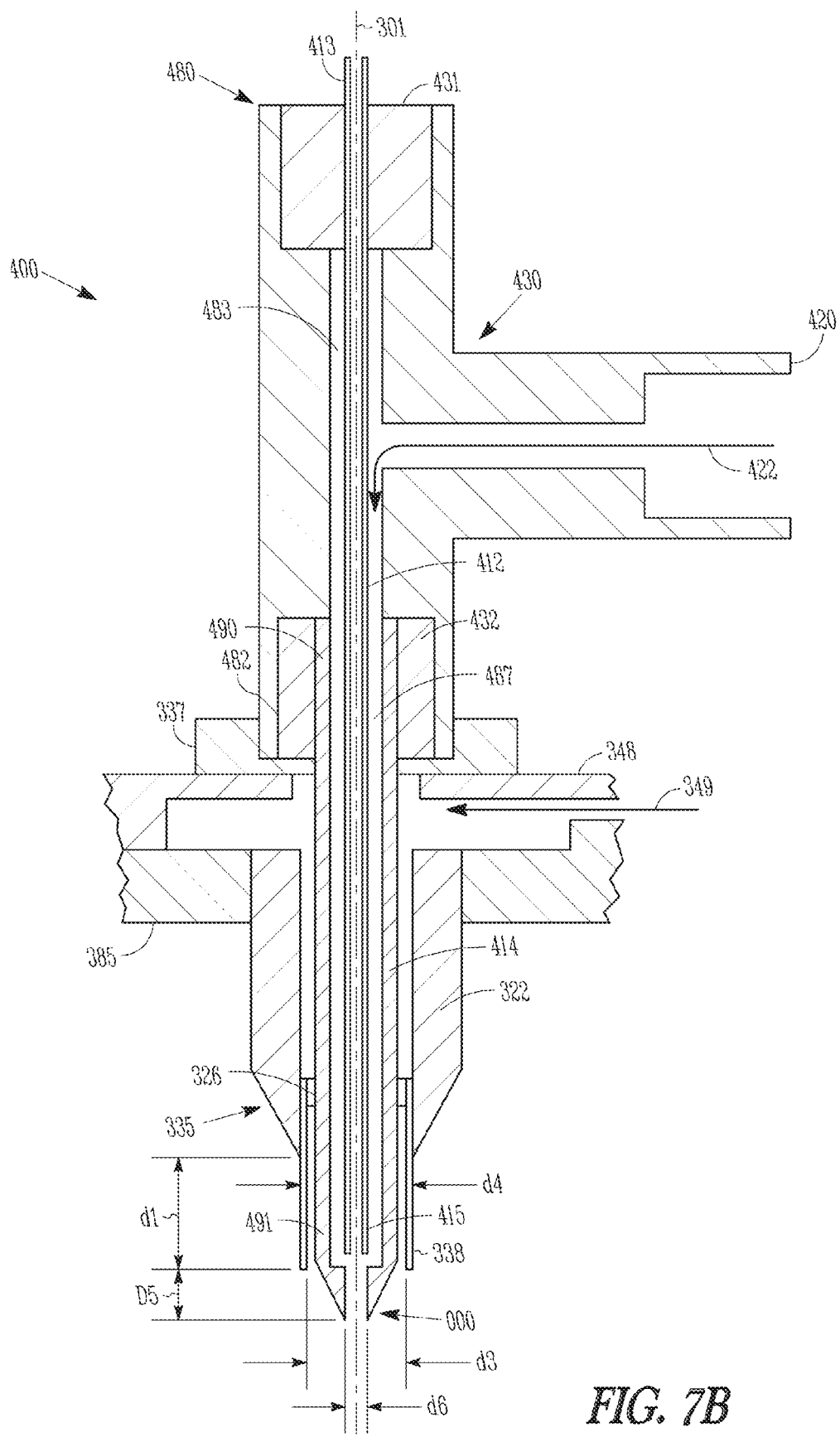
FIG. 7B shows a more detailed diagram of one embodiment of a triple opening electrospray dispensing apparatus according to the present invention that may be controlled for applying one or more of the types of coatings such as generally shown in FIGS. 3A-3C.

FIG. 7B is a more detailed diagram of an alternate exemplary capillary electrode configuration 400 for the distributor head 316 of FIG. 7A which includes the ability to spray particles from three flows of three different liquid compositions. Like reference numbers are used in FIG. 7B for corresponding like elements of FIG. 7A to simplify description of the alternate capillary configuration 400.

The capillary electrode configuration 400 includes a first capillary tube 412 having an axis coincident with axis 301 for receiving a first flow of a liquid spray composition from a source, e.g., a suspension of biologically active material, such as a drug. Further, a second capillary tube 414 is concentric with the first capillary tube 412. An annular space 487 between the inner and outer capillaries 412, 414 is used to receive a second flow of a liquid spray composition (e.g., a polymer dissolved in a suitable solvent) and provide the flow to the dispensing tip 495 for use in establishing the spray forward thereof. In more detail, the housing portion 430 includes an aperture 483 extending from a first end 480 of the housing portion 430 to a second end 482 thereof. An inlet port 420 opens into the aperture 483. The inlet port 420 receives the second flow of liquid spray composition 422 to be directed in the annular space 487 about the capillary tube 412.

The first capillary tube 412 has a first end 413 and a second end 415. The capillary tube 412 is positioned in the aperture 483 of the housing portion 430 of generally T-shaped configuration. The first end 413 of the capillary tube 412 is sealed to housing 430 using conductive element 431 at the first end 480 of the housing portion 430. The capillary tube 412 extends from the second end 482 of the housing portion 430 and with the second capillary tube 414 forms the annular space 487.

The second capillary tube 414 includes a first end 490 and a second end 491. The second capillary tube 414 is positioned so that it is concentric with the first capillary tube 412. The first end 490 of the second capillary tube 412 is coupled to the second end 482 of the housing portion 430 using conductive element 432. Further, the second end 491 of the second capillary tube 414 is held in place relative to the nozzle portion 322 by spacers 326. The second capillary tube 414 extends beyond the first capillary tube 412 a predetermined distance in the direction of the target surface to be coated; about 0.2 mm to about 1 mm. The portion of the second capillary tube 414 at the dispensing tip 495 which extends beyond the first capillary tube is tapered at a 60 degree to 75 degree angle for obtaining stable spray pattern and operation mode, e.g., consistent spraying patterns.

Further, the second capillary tube 414 extends beyond the second end 338 of the nozzle portion 322 a predetermined distance (d5), about 2 mm to about 5 mm. The first capillary tube 412 has diameters like that of capillary tube 320 of FIG. 7A. The second capillary tube concentric with the first capillary tube has an outer diameter of about 533.4 μm to about 546.1 μm and an inner diameter of about 393.7 μm to about 431.8 μm. The gap d6 at the tip of the second capillary tube 414 is in the range of about 10 μm to about 80 μm. The other configuration parameters are substantially equivalent to that described with reference to FIG. 7A. In such a configuration, dual streams of liquid spray compositions are provided for establishing a spray from dispensing tip 495 of the apparatus. However, further, a third liquid diluent composition 349 is also provided through inlet port 348 to dispensing tip 495.

Clearly, the present invention is not limited to the use of capillary-type nozzle structures as various suitable nozzle structures may be employed. For example, any nozzle structure suitable to provide a spray of particles according to the principles described herein may be used, e.g., slits that may provide various cone-jets, nozzle structures having portions thereof that are integral with portions of other nozzle structures, nozzle structures that form a part of a chamber wall, radially or longitudinally configured slots, or other multiple opening nozzle structures (e.g., micromachined nozzle structures that have dual or triple openings), etc.

Figure 8:
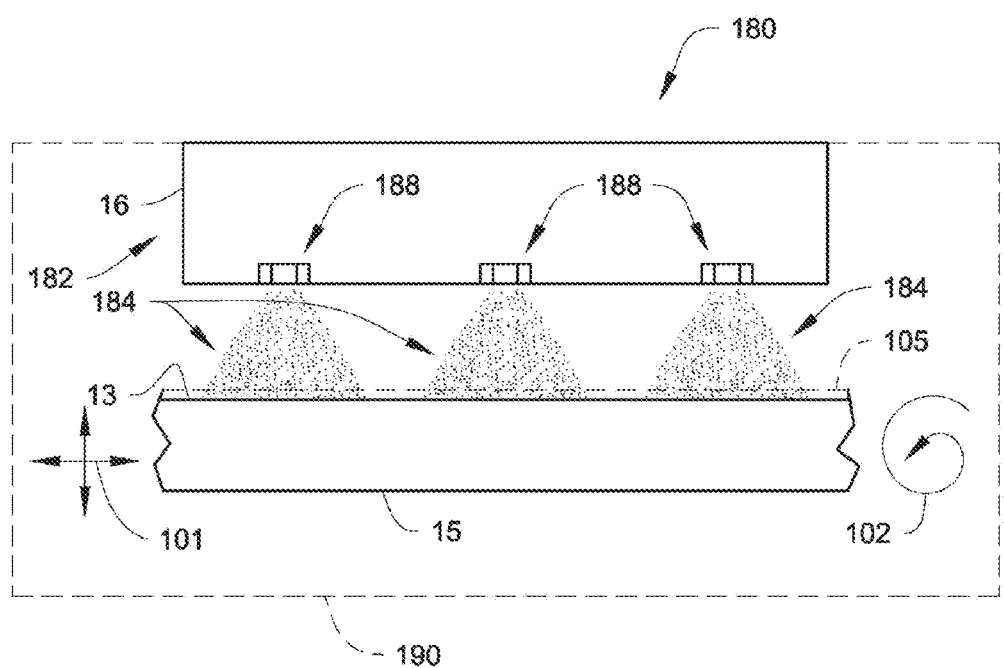
FIG. 8 shows a general diagrammatical illustration of a configuration of providing multiple electrospray nozzle structures according to the present invention that may be employed in the coating system shown generally in FIG. 1.

Yet further as would be recognized by one skilled in the art multiple nozzle structures may be used to increase coating capacity according to the present invention. For example, as shown in FIG. 8, an electrospray coating system 180 employs a dispensing apparatus 182 to establish one or more sprays of particles 184 (e.g., sprays of microdroplets which evaporate to form sprays of coating particles). The dispensing apparatus 182 includes a plurality of nozzle structures 188 which operate in a manner like that of nozzle structure 18 as shown in FIG. 1 to provide a selected type of coating 105 on surface 13 of object 15 positioned in a defined volume (shown generally by the dashed line 190).

Examples Setup

The examples to follow were carried out to produce nanocomposite coatings on surfaces with intricate architecture using an electrospray process that generates nanoparticles, initially focusing on coronary stents, and quantifying their physical characteristics. Further, the examples were carried out to achieve a level of reproducibility and performance of surface coatings. Yet further, the examples were carried out to:

1. Assess the relative importance of multiple coating process parameters on achieving the type of coating desired where outcome measures included coating weight, coating characteristics, and voltage required to maintain a stable cone-jet for each set of conditions including:
   a. Feed rate and composition of polymer, drug and solvent
   b. Polymer and drug concentration in sprayed material
   c. Conductivity of spray fluids
   d. Distance between spray tip and target
2. Using optimized process parameters, apply consistent coating weights to the surface of a coronary stent for one or more polymers, where the target weight of coating was between 400 and 600 μs for polymer and drug combined.
3. Determine the transfer efficiency for each coating, defined as the ratio of the coating weight to the mass of solid material sprayed.
4. Determine coating thickness using tangential cryomicrotomy and scanning electron microscopy and profilometry.
5. Determine coating characteristics, surface uniformity, and adherence of each coating type before and after balloon expansion of the stent.
6. Determine the uniformity of the drug/polymer matrix exploring other possibilities including atomic force microscopy and FTIR microscopy.
7. Determine the stability of biodegradable coatings under high ambient humidity.

Coating Reagents Used in the Examples

For the primary coating experiments, conducted to determine coating consistency and to optimize process-control variables, we selected polymers available on the market that represented a range of potential coating materials, from biodegradable materials to drug-eluting materials. The required solvents to dissolve these polymers ranged from solvents with higher dielectric constants (e.g., acetone and methanol) to solvents with lower dielectric constants (e.g., tetrahydrofuran and toluene).

The majority of experiments were made using two polymers: Poly(DL-lactide-co-ε-caprolactone, 80/20) (PLCL), inherent viscosity 0.77 dL/g in chloroform, is a biodegradable polymer that was available from Absorbable Polymers International, Pelham, Ala., USA; and Chronoflex AR (CFR) is polyurethane 22% solid in dimethylacetamide. CFR, a biodurable polymer, is available from CardioTech International, Wilmington, Mass., USA.

Solvents used for these various polymers included acetone, chloroform, tetrahydrofuran (THF), methanol (solvents were HPLC grade) and phosphate buffer, pH 7.4, all available from Sigma-Aldrich, St. Louis, USA. We also conducted exploratory spray experiments with two additional polymers, poly (isobutylene) (PIB) and poly(tetrahydrofurfuryl methacrylate-co-ethyl methacrylate) PTHFMA-EM, also available from Sigma-Aldrich.

Initially three drugs were proposed for use in the coatings: dexamethasone, rapamycin and paclitaxel; e.g. see Ranade et al (2004). In the course of these studies, we sprayed both dexamethasone and paclitaxel successfully. Because of the potential toxicity of rapamycin and paclitaxel and the possibility of contaminating the shared instruments in the facility where the imaging was conducted, we elected to conduct the characterization studies using dexamethasone as the primary drug agent. Dexamethasone (99% purity) was available from Alexis Biochemicals, San Diego, Calif., USA.

Solutions of polymers were prepared at different concentrations as determined by the spraying conditions. A variety of polymer concentrations and solvent combinations were investigated; acceptable concentrations (weight/volume) and primary solvents included PLCL 5% in acetone or a blend of acetone and chloroform, CFR 2% in THF or a blend of THF and methanol, PIB 1% in THF, and PTHFMA-EA 2% in THF, e.g. see Alexis et al (2004), Puskas et al (2004), Szycher et al (2002), and Verhoeven et al (2004). Dexamethasone was added to polymer solutions, with final concentrations varying from 10% to 20% of the polymer weight, resulting in a 10:1 polymer:dexamethasone ratio by weight. Conductivity of solvent solutions was adjusted to appropriate ranges, typically by adding μl quantities of concentrated nitric acid, measured using a Orion Benchtop Conductivity Meter, model 555A with probe M (Thermo Electron Corp., Waltham, Mass., USA).

The optimal spray solvent for each polymer was determined by comparing the various solvents specified as compatible with each polymer by the manufacturer and assessing spray performance in terms of ability to form a stable cone-jet (i.e., stable dark tip appearance, no fluttering between cone-jet and non-cone-jet mode, and no corona discharge, see FIG. 2C herein). A stable cone-jet is required to maintain uniformity of particle size during the spray process. Likewise, optimal feed rates were determined by evaluating the voltage required to generate a stable cone-jet spray mode while, at the same time, visually inspecting the target for obvious flaws such as spatter marks on the surface that were seen when the cone-jet was disrupted. This process produced a set of voltages and feed rates for each polymer and solvent combination that were compatible with electrospray operation in the cone-jet mode.

Targets Used for Coating Examples

Generic stents that could be expanded in diameter 3-fold by balloon were obtained (Pulse Systems, Concord, Calif., USA). These were fabricated from 316 stainless steel that was annealed and electropolished. Dimensions were 12 mm in length, 1.57 mm in outer diameter and 1.30 mm in inner diameter, a size and general configuration that is equivalent to stents in current use.

Because some of the coating characterization tools could not be used to assess a rounded surface, flat stainless steel plates were used for some aspects of coating development. One cm-square pieces were pressed from 30.5 cm-square mirror-finished 316 stainless steel sheets 0.79 mm thick (McMaster Carr, Chicago, Ill., USA). For coating experiments, the coating was sprayed on the mirror-finished side of the small cut pieces.

Electrospray Coating Apparatus

Two electrospray systems were used in these experiments. One system, which had a fixed target, was used to explore optimum spray conditions. The second system, which had a movable spray target platform, was used as the primary stent-coating apparatus. The spray head in both of these systems was a custom-manufactured dual capillary design, in which each capillary was fed by external syringe pumps (Harvard Apparatus, Holliston, Mass., USA). A high-voltage power supply (Bertan Associates, Hicksville, N.Y., USA) was used to apply voltage to the spray tip, typically over a range of 3.5-5.5 kV at ~2.5 mA. The target was moved into position by a motor-driven, computer-controlled, movable stage that permitted vertical and horizontal adjustments in positioning the target with respect to the spray tip as well as a variable advancement rate of the target through the spray field. The spray operation was imaged using a video inspection microscope (Panasonic) that produced real-time images of the spray tip as well as the target. The spray operation was contained within a negative-pressure chamber that drew gas supply (air, nitrogen or carbon dioxide) through a filtered supply line and was vented through a filter and fume hood. Temperature and relative humidity were monitored continuously.

Unless otherwise indicated, the spray apparatus used to coat objects by electrospray was equivalent to that shown in and described with reference to FIG. 7A. The apparatus included a dual concentric opening dispensing device 314 extending along axis 301. First end 304 was formed of conductive portions to facilitate application of voltages or ground to capillary tube 320. The capillary tube 320 was formed of stainless steel and had an outer diameter of 560 μm and an inner diameter of 260 μm. Further, the distributor head 316 included a nozzle portion or casing 322 that was an elongate substantially cylindrical metal casing concentric with the capillary tube 320 for providing an outer opening 392 concentric with inner opening 391 of the capillary tube 320. The casing or nozzle portion 322 included a first end portion 336 which tapered at section 335 thereof to a narrower second end portion 338. The second end portion 338 extended from the tapered section 335 and is concentric with the second end 332 of the capillary tube 320. The distance from the end of the tapered section 335 to the end of the metal casing 322 is about 4.7 mm. The outer diameter of the second end portion 338 is about 1050 μm and the inner diameter of the second end portion 338 is about 680 μm. The second end 332 of the capillary tube 320 extends beyond the second end portion of the metal casing or nozzle portion 322 towards the target surface to be coated by a distance of about 5 mm.

The dispensing device was constructed of various materials. Primarily, the conductive elements (e.g., element 316) were constructed of stainless steel, the apparatus was used in a chamber made of plexiglass, and insulative parts (e.g., element 383) thereof were made of a plastic, black delrin, material.

The electrospray was operated in a cone-jet mode with a flow of 4000 cc/min flow of $N_2$ through port 354 and about the same amount exhausted from the coating system.

Determining Optimal Spray Operating Parameters

Coating Weight

For each coating, at least 10 to 12 individual stents were sprayed consecutively. Coating weight was determined by weighing the spray target before and after spraying using a Cahn electrobalance, Model 21. A goal was to achieve coatings of approximately 500 µg per stent; however, we also conducted some spray experiments where very thin coatings of approximately 40 µg were applied, or where we coated only certain regions of the stent, for a coating weight of approximately 30 µg.

Transfer Efficiency

Transfer efficiency is defined as the ratio of the mass of solid material sprayed to the weight of the coating. Only the weight of coating on the target stent was determined; the weight of material that adhered to the spray fixture was not used in the calculation due to the inability to weigh the much larger fixture reliably. Most likely the portion of sprayed material that was not present on the stent was captured by the fixture due to the force of attraction generated by the strong electrical field.

Coating Uniformity

Stents were imaged using light and scanning electron microscopy (SEM) to verify coating qualities, surface uniformity, and lack of void areas or webbing at strut junction points. A light microscope image was used to record lack of obvious deformity in the stent structure. Coating images were assessed on multiple points over the outer and inner surfaces of the struts, at low (45×) and high (5000× and 20,000×) magnifications. For production lots, samples were selected randomly from each lot.

Surface coating thickness uniformity was also assessed by SEM imaging of cross sections of tangential cuts made by glass blade microtome at two or more points on each individual stent. Because the nanocomposite coating distorted under conditions of room-temperature sectioning, tangential cryomicrotomy was used to cut the coating on the selected strut at low temperature. A series of experiments were done to find the optimal temperature. At –120° C., the coating started coming off as pieces, leaving the cutting edge clean. Because of the low stiffness of the coating, a glass knife was used to cut at 1 mm/s cutting rate and 0.5 um per step feeding rate. SEM images were then taken and the thickness for each type of coating was estimated.

Coating thickness was also assessed using profilometry. Because the profile across the curved stent surface could not be obtained, coatings were sprayed on 1-cm-square polished 316L stainless steel plates, using similar spray conditions and time for each of the polymer-drug blends and surface types, respectively. Three squares were placed on a flat fixture and coated during a single spray period. Samples were evaluated using a Dektak 3030 profilometer (Veeco Instruments, Woodbury, N.Y., USA) and a Tencor P-10 profilometer (KLA-Tencor Instruments, San Jose, Calif., USA). As the stylus scanned the surface, the profile was recorded. The stylus load was kept at 0.05 mg so that the coating would remain intact without leading to false measurement. Thickness data was derived from the profile.

Imaging

Imaging experiments utilized light images of stents taken using a Nikon Model SMZ1500 stereomicroscope. Higher-magnification surface images were taken using a Hitachi Model S-3500N VP scanning electron microscope (SEM). For this, samples were mounted and then coated with gold under 250 µm Hg of argon, using 15 µA of current for 1.5 minutes, and then placed on the microscope stage. For atomic force microscopy, a Digital Instruments Nanoscope III MultiMode Scanning Probe Microscope with an auxiliary Extender electronics module was used in tapping mode. For Fourier Transform Infrared (FTIR) Spectra microscopy, PLCL coated stents with and without dexamethasone were imaged using a Nicolet Magna-IR 750 model attached to a Nic-Plan IR Microscope. The microspectroscopy was done under reflectance mode with 10 µm beam size. The background was collected on a mirror with gold coating. FTIR spectra on multiple spots of the coating were compared.

Coating Adherence

Two techniques were used. Coating adherence after balloon expansion of the stent was assessed by SEM imaging, looking for patterns of obvious cracking or delamination of the coating surface from the stent structure. In another approach, we also explored use of a "tape test," in which the coated stent mounted on a rigid wire fixture was placed with gentle pressure onto the adhesive side of Scotch Magic tape (3M, St. Paul, Minn., USA) and then removed from the tape quickly by pulling at either end of the wire fixture. This method was less satisfactory due to problems standardizing the technique and deforming the stent.

Effect of Humidity on Coating Surface

Because the PLCL polymer is known to biodegrade in the presence of water, we evaluated the effect of short-term exposure of a high moisture environment on the surface characteristics. Stents coated with the PLCL open matrix coating and the PLCL smooth coating (i.e., closed film coating) were exposed to 99% relative humidity at room temperature in a closed container. Stents were evaluated at 24 and 72 h and these images compared to control stents that were maintained under dry conditions.

Statistical Methods

Experimental outcome data descriptive statistics were calculated using Microsoft Excel and reported as mean, standard deviation (SD) and coefficient of variation (CV).

RESULTS OF EXAMPLES

Design of Experiment (DOE) Results

Evaluation of the Spray Process Variables on Coating Matrix

These experiments were conducted to investigate the impact of PLCL polymer concentration in final spray stream, presence of the drug dexamethasone (DEX), conductivity, and distance from spray head to target on the final coating matrix appearance. The desired coating matrix was a uniform open matrix of round particles. As explained above, a Design of Experiment (DOE) approach was taken to setting up the experimental conditions and evaluating the impact of the various process parameters. This is a highly efficient way of identifying optimal coating conditions for a particular polymer and coating finish. The experimental conditions are summarized in the table of FIG. 9 and the images of the resulting coatings shown in FIG. 10. The table of FIG. 9 includes the experimental conditions and outcome measures to assess impact of process parameters on achieving desired coating surface appearance.

The effect of the process parameters with respect to achieving the desired coating appearance is summarized in the table of FIG. 11 which shows the relationship of process parameters to experimental outcome variables (↔ little effect, ↑ increase). As can be seen from this chart, a higher polymer-to-diluent ratio (i.e., liquid spray composition provided at the inner opening or inner capillary to liquid diluent composition provided at the outer opening of the spray apparatus), is the sole factor associated with greater coating weight; spray distance (i.e., distance from dispensing end to the target) and conductivity of the diluent in the outer capillary (which has a major impact on conductivity of final spray stream) are both associated with the requirement for a higher spray voltage, and a higher conductivity is the sole factor associated with achieving the desired coating surface.

Another factor that was determined to affect the stability of the spray operation was defining the range of voltage for a particular fluid that was associated with a stable cone-jet mode. The cone-jet mode is the operating mode that produces the most uniform particles. The voltage that must be applied to achieve the cone-jet mode is related to the conductivity of the spray fluid, so in one sense it is an outcome measure defined by the feed fluid. However, it can also be controlled within a certain range to produce the cone-jet operation. As shown in FIGS. 2A-2C herein, voltage is increased, the dripping spray tip (FIG. 2A) first assumes a pulsating appearance (FIG. 2B) and eventually the cone-jet mode (FIG. 2C) which produces the most stable nanometer-sized particles.

As has been reported previously by Chen and Pui (1995), there is hysteresis in the operating current across the target during cone-jet operation and the operating voltage, which is different when the voltage is increasing than when it is decreasing.

Figures 12, 13:
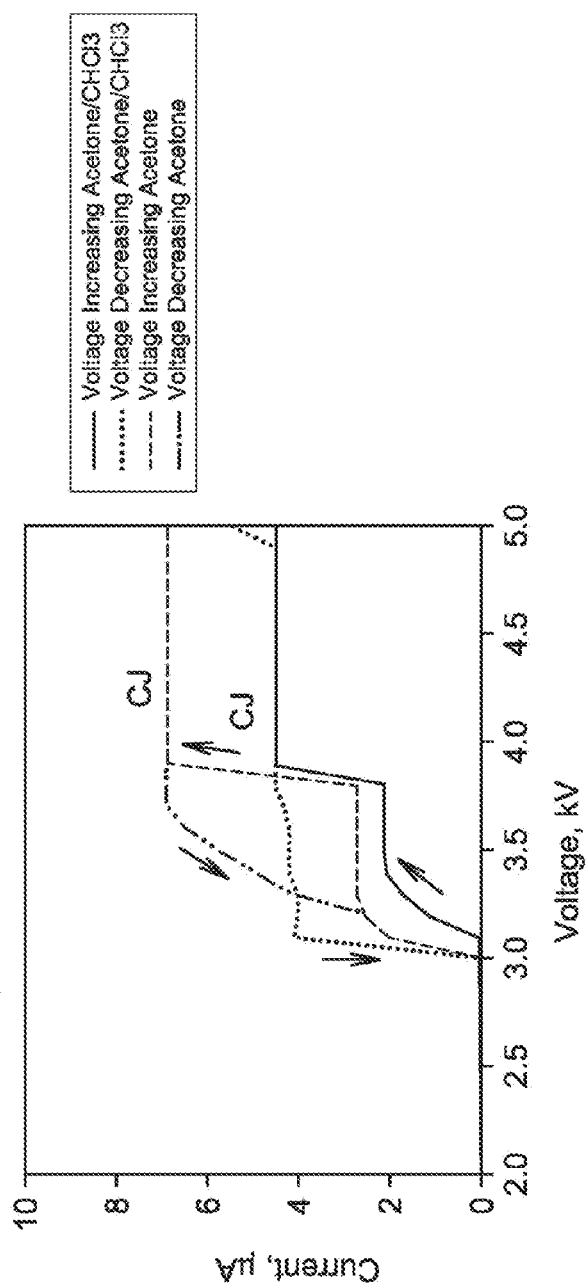
FIG. 12 shows a graph of hysteresis effect on the relationship between voltage and current through the spray target while operating the electrospray technique according to one or more examples provided herein.
FIG. 13 shows a table of stent and coating weights for each lot of various coating polymers and surfaces according to one or more examples provided herein.

This is a unique relationship for each polymer/solvent combination, as shown in FIG. 12. In this experiment, the polymer was PLCL and the solvent was acetone alone or a blend of acetone and chloroform (90:10) (used to produce the open matrix and smooth coating (i.e., closed film) surfaces, respectively). FIG. 12 shows the hysteresis effect on the relationship between voltage and current through the spray target while operating electrospray in the cone-jet mode. Cone-jet (CJ) operation was observed within the voltage ranges that were marked by rapid changes in the current, depending on whether voltage was increasing or decreasing.

These process control experiments are significant because they demonstrate that a set of operating parameters can be identified for a given polymer, drug and solvent combination that produce a desired surface finish (e.g., selection of a particular type of coating).

Results of Coating Weight Consistency for Production Lots of Three Different Coating Surfaces Three separate lots of a minimum of 10 stents each were coated with two different polymers, both containing the anti-inflammatory agent dexamethasone. The biodegradable polymer PLCL was used to apply coatings with two unique surface characteristics—a highly porous ("open matrix") finish, or a smooth ("closed") finish. The drug-eluting polymer Chronaflex AR produced a smooth, "closed" finish with the family of solvents investigated. Coating spray times were approximately 20 minutes for each of these spray runs. Images for each of these coating surfaces are provided under description related to "Coating Adherence," below. Stent and coating weights are summarized in the table of FIG. 13 which shows stent and coating weights for each lot of the various coating polymers and surfaces.

Figure 14:
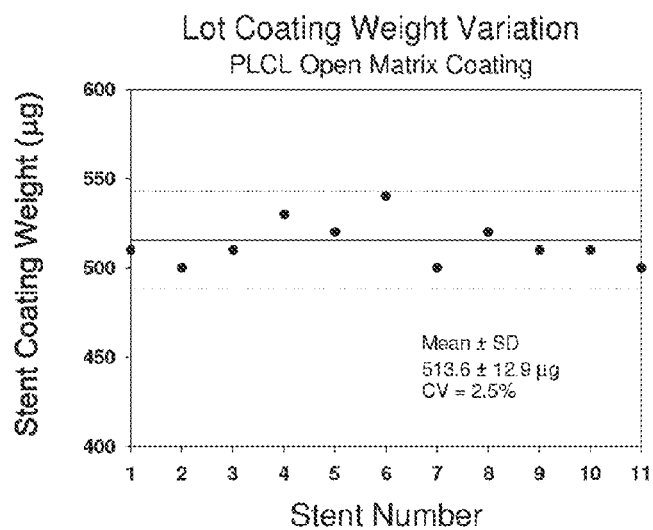
FIGS. 14, 15 and 16 show graphs of coating net weights for lots of stents provided with open matrix coatings and closed film coatings according to one or more examples provided herein.

Coating weights of individual stents were plotted for each lot to determine how many individual samples had coating weights exceeding 2 SD. FIG. 14 shows a plot for the open-matrix coating with PLCL, FIG. 15 for the smooth coating (i.e., closed film) with PLCL, and FIG. 16 for the smooth coating with Chronoflex AR. Notably, in none of the lots did a single stent coating weight exceed 2 standard deviations.

FIG. 14 shows the coating net weights for a lot of stents produced with the open matrix PLCL coating. The optimum solvent for PLCL was acetone. To produce this coating finish, the ideal feed rate of the polymer/acetone solution was determined to be 6.5 µl/min sprayed at a distance of 10 mm. (See, for example, DOE results for the impact of various spray operating parameters on final coating appearance.) Maintenance of the cone-jet mode required some increase of voltage during each individual spray run. For the stents in this lot, the inner capillary feed was PLCL 5% and DXM 0.5% in acetone at a rate of 1.5 µl/min, with an outer capillary feed of acetone, with nitric acid added to adjust conductivity to 6.8 µS/cm, at a flow rate of 5 µl/min.

Figure 15:
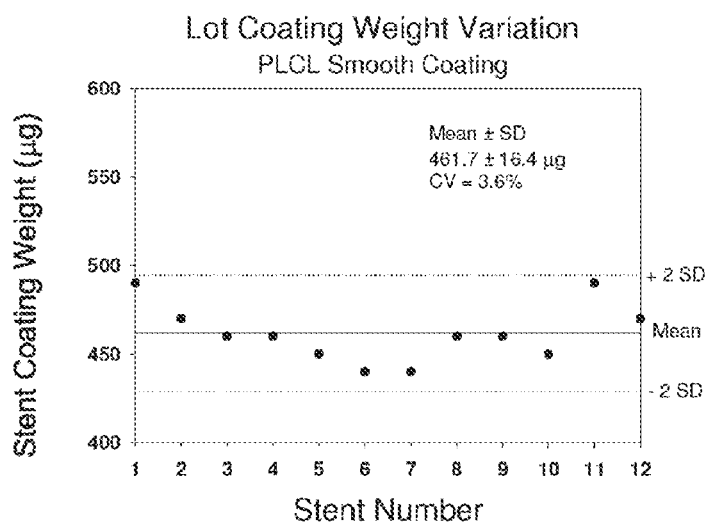

FIG. 15 shows coating net weights for a lot of stents produced with the smooth PLCL coating (i.e., closed film coating). To produce this coating finish, the feed rate of the polymer/acetone/chloroform solution was 10.75 µl/min sprayed at a distance of 10 mm. Voltage was stable throughout each individual spray run. For the stents in this lot, the inner capillary feed was PLCL 5% and DXM 0.5% in acetone at a rate of 0.75 µl/min, with an outer capillary feed of acetone 40% and chloroform 60%, at a flow rate of 10 µl/min.

Figure 16:
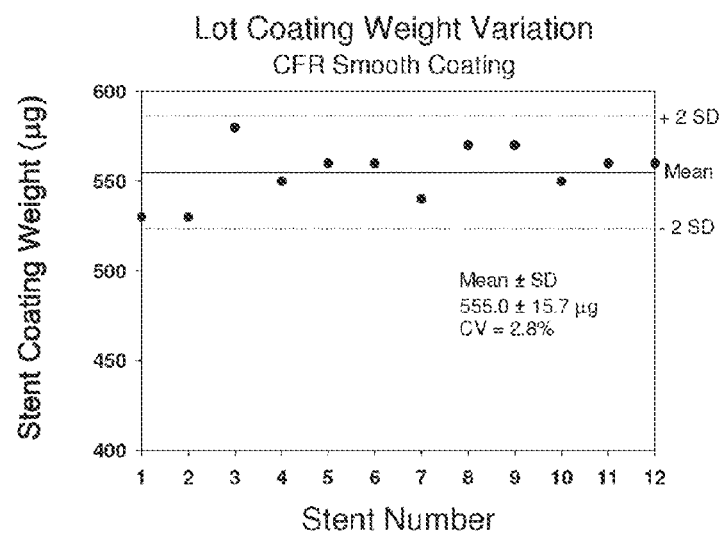

FIG. 16 shows coating net weights for a lot of stents produced with the smooth Chronoflex AR coating (i.e., closed film coating). The optimum solvent for this polyurethane was a blend of tetrahydrofuran and methyl alcohol. Polymer solution feed rate was 10.0 µl/min sprayed at a distance of 8 mm. Voltage was stable throughout the coating of each individual stent. For the stents in this lot, the inner capillary feed was CFR 2% and DXM 0.2% in THF 83.3% and methanol 16.7% 2.0 µl/min, with an outer capillary feed of THF 83.3% and methanol 16.7% at a flow rate of 8 µl/min.

The consistency of these coating runs is significant because it demonstrates that these three different coatings can be reproduced with minimal between-stent variation in coating weight. These experiments furthermore demonstrate that coatings of acceptable weights can be achieved with these particular drug/polymer combinations.

One process parameter is the length of spray time. The coatings in these experiments, made using single spray units, took a spray time of 20-25 min. This can be shortened by operating multiple spray units in serial or parallel or by adding additional spray heads targeting each individual stent.

Coating Transfer Efficiency Results

Figures 17, 18:
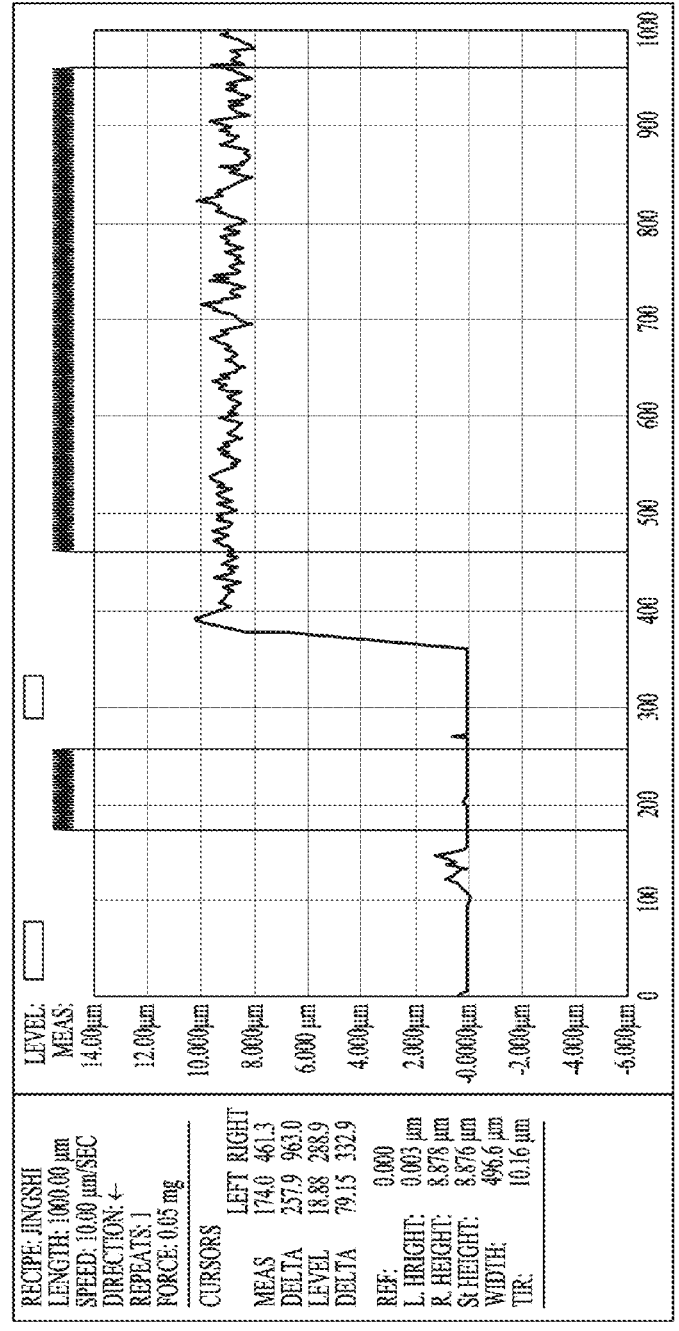
FIG. 17 shows a table regarding coating transfer efficiency as a function of coating polymer, surface, and solvents, according to one or more examples provided herein.
FIG. 18 shows a graph of a profilometer scan showing coating thickness according to one or more examples provided herein.

Coating transfer efficiency is the amount of sprayed material that is applied to the stent surface. Transfer efficiency for each of the three coatings is shown in the table of FIG. 17 which shows coating transfer efficiency as a function of coating polymer, surface and solvents. The lowest transfer efficiency was seen for the PLCL open matrix finish. The spray pattern for this finish was much broader than seen for the other two finishes due to the higher conductivity of the sprayed material. Higher conductivity fluids generate smaller nanoparticles, which appears to correlate with wider spray patterns. A broader spray pattern means that more material is applied beyond the stent target area to the fixture.

Coating Thickness Results

Coating thickness was assessed by two different methodologies: profilometry, which uses a surface scan on the coating and a baseline uncoated reference area, and cyromicrotomy followed by SEM imaging.

Figure 19:
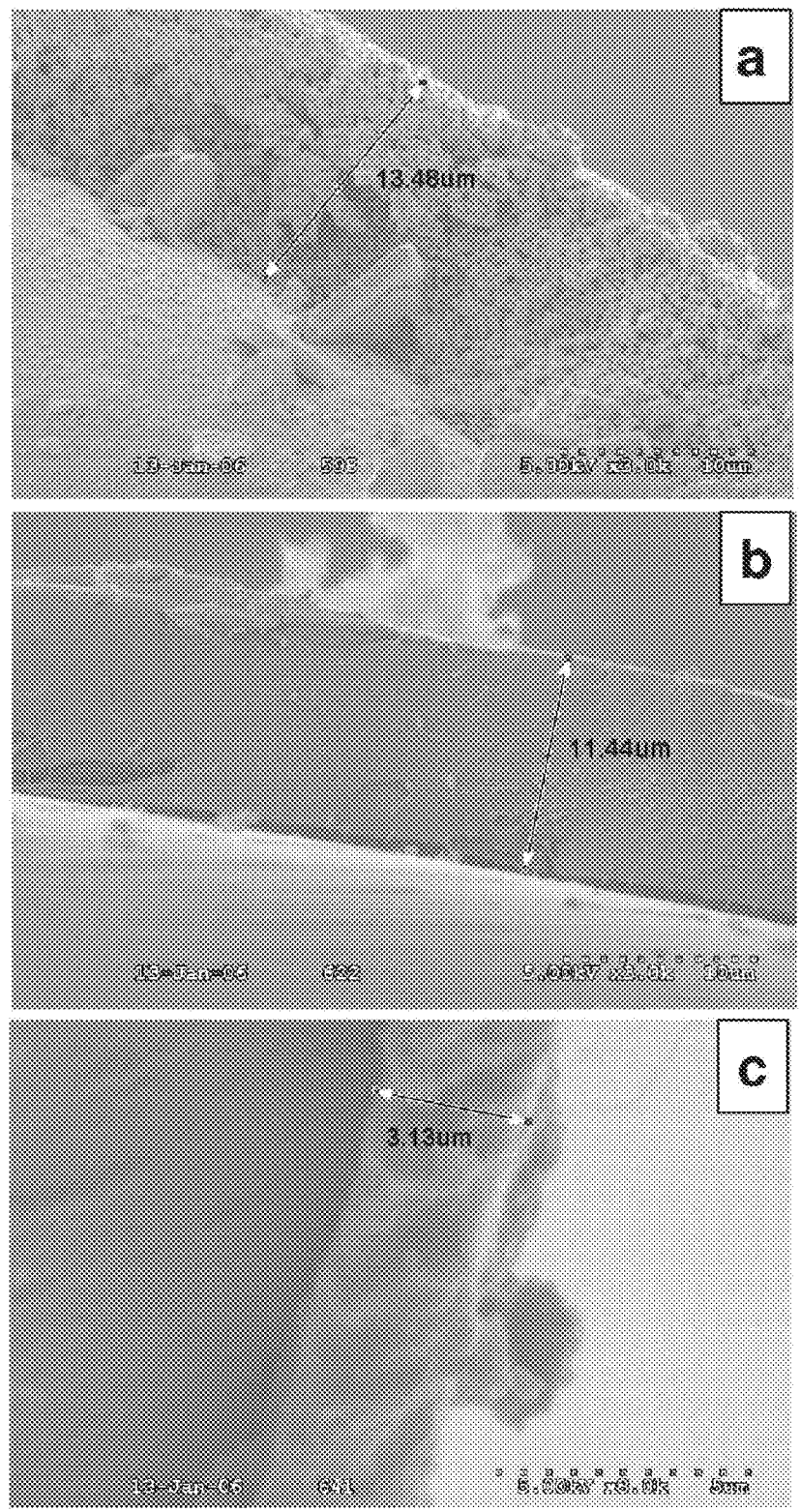
FIGS. 19a, 19b and 19c show cross-sectional images of three coatings produced according to one or more examples provided herein.
Figure 20:
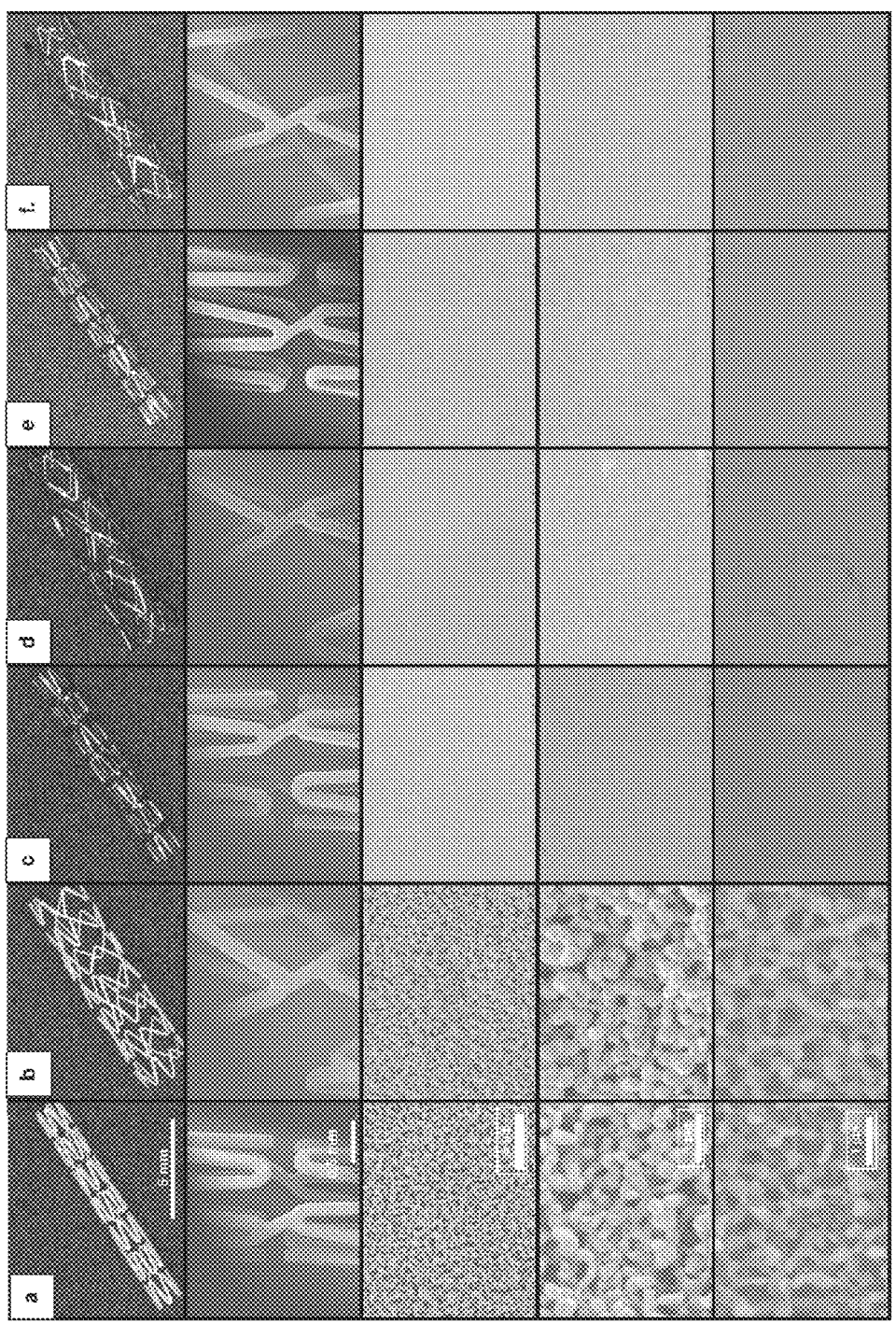
FIGS. 20a, 20b, 20c, 20d, 20e and 20f show SEM images of coatings according to one or more examples provided herein.
Figure 22:
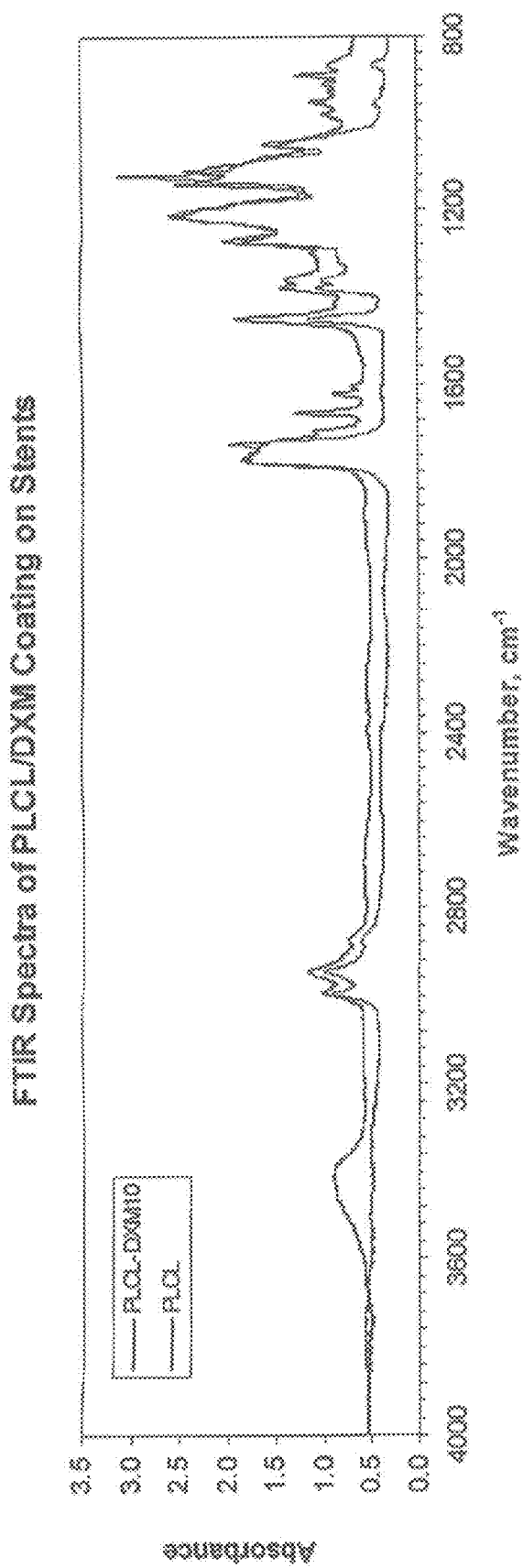
FIG. 22 shows an FTIR Spectra of a couple of coatings according to one or more examples provided herein.

Profilometry was only capable of measuring thickness on flat surfaces. Samples were prepared by coating the surface of the polished 316 stainless steel squares described earlier. While coating thickness estimates were roughly equivalent to those reported above for cryomicrotomy, this method is of limited utility because it is not applicable in its present form for the curved surface of the coronary stent. An example of a scan is shown for a PLCL open matrix coating on the flat surface in FIG. 18 which is a profilometer scan made with a Tencor P10 instrument. Coating thickness was estimated at approximately 10 μm. Cryomicrotomy followed by SEM imaging was of considerably greater utility. The cross-sectional images also provide a view of the uniformity of the coating. Examples of microtomed samples are shown in FIGS. 19*a-c*. FIG. 19 shows cross-sectional images of the three coating types produced during the production lots. Extraneous material in each image is debris caused when the microtome glass knife shatters the surface during section cuts. FIG. 19*a* shows an open matrix PLCL coating. The crystalline-appearing debris is fragments broken from the glass knife when it hits the stent surface. Coating thickness is measured to be 13.48 μm. FIG. 19*b* shows a smooth PLCL closed film coating. Thickness is measured to be 11.44 μm. The minor separation between the coating and the stent surface that is visible in this image may be artifact produced when the coated stent is cooled under liquid nitrogen in preparation for sectioning. FIG. 19*c* shows a Chronoflex AR coating. Thickness is measured to be 3.13 μm.

Cryomicrotomy and SEM imaging is the most practical method for assessing coating thickness. Ideally a profilometer-type assay could be developed, using cryomicrotomy/SEM imaging as a benchmark for method validation.

Results for Coating Surface Characteristics, Surface Uniformity and Adherence, Before and after Balloon Expansion Coating surface characteristics were initially evaluated through pilot studies and SEM imaging. After optimizing process variables for a particular polymer/drug combination and the desired surface architecture, we needed to demonstrate that these surface characteristics could be reliably and consistently produced. Using the uniform lots of coated stents, the consistency of coating surface characteristics was assessed by randomly selecting and SEM-imaging three stents from each lot in the non-expanded state and three stents after balloon expansion to 3 mm. Representative images for each coating (as shown by the key to the images provided in the table of FIG. 21) are shown in FIGs. a-f. Small type information too small to read at the bottom of each image is summarized in the key.

As is clear in the images of FIG. 20*a-f*, all three types of coating surfaces are uniform without obvious coating voids. Coatings were deemed to be acceptable if they exhibited overall uniformity, no obvious coating voids, evenness on the internal surface of the strut, and lack of webbing or pooling and strut angles.

We also conducted pilot spraying experiments using PIB 1% in THF, and PTHFMA-EA 2% in THF, both with dexamethasone at 10% the level of the polymer. The PIB gave a smooth coating, while the PTHFMA-EA gave a large, irregular open matrix surface.

In the images shown in FIGS. 20*a-f*, all surfaces appeared to be adherent prior to balloon expansion. The PLCL open matrix coating showed evidence of minor cracking along strut angles after balloon expansion. At higher magnification (not shown), these cracks did not appear to reach the stent surface. None of the coatings delaminated after balloon expansion. We also evaluated adherence using the "Scotch Tape" test. In practice, this test was difficult to standardize. While this removed some of the material from the open matrix PLCL coating (image not shown), some particulate surface remained. This finding is consistent with the balloon expansion observation, demonstrating tight adherence to the stent surface layer.

These images demonstrate that all three polymer/drug coatings could be uniformly applied. PLCL, but not Chronoflex AR, gave a very uniform open matrix surface. Both PLCL and Chronoflex AR gave very smooth coatings with minor surface variations only visible at 20,000× magnification Inner and outer strut surfaces were similar in appearance and there were no obvious voids, demonstrating the important sheath-like coating that is achieved with the non-line-of-sight electrospray process.

Methods for testing coating adherence under likely stress conditions, include, for example, balloon expansion. Adherence could be improved for some polymers, if necessary, with use of a surface priming treatment on the stent surface. The open matrix PLCL coating showed minor cracking at the strut points after balloon expansion, providing information for further coating optimization.

Matrix Stability With Humidity Results

Figure 23:
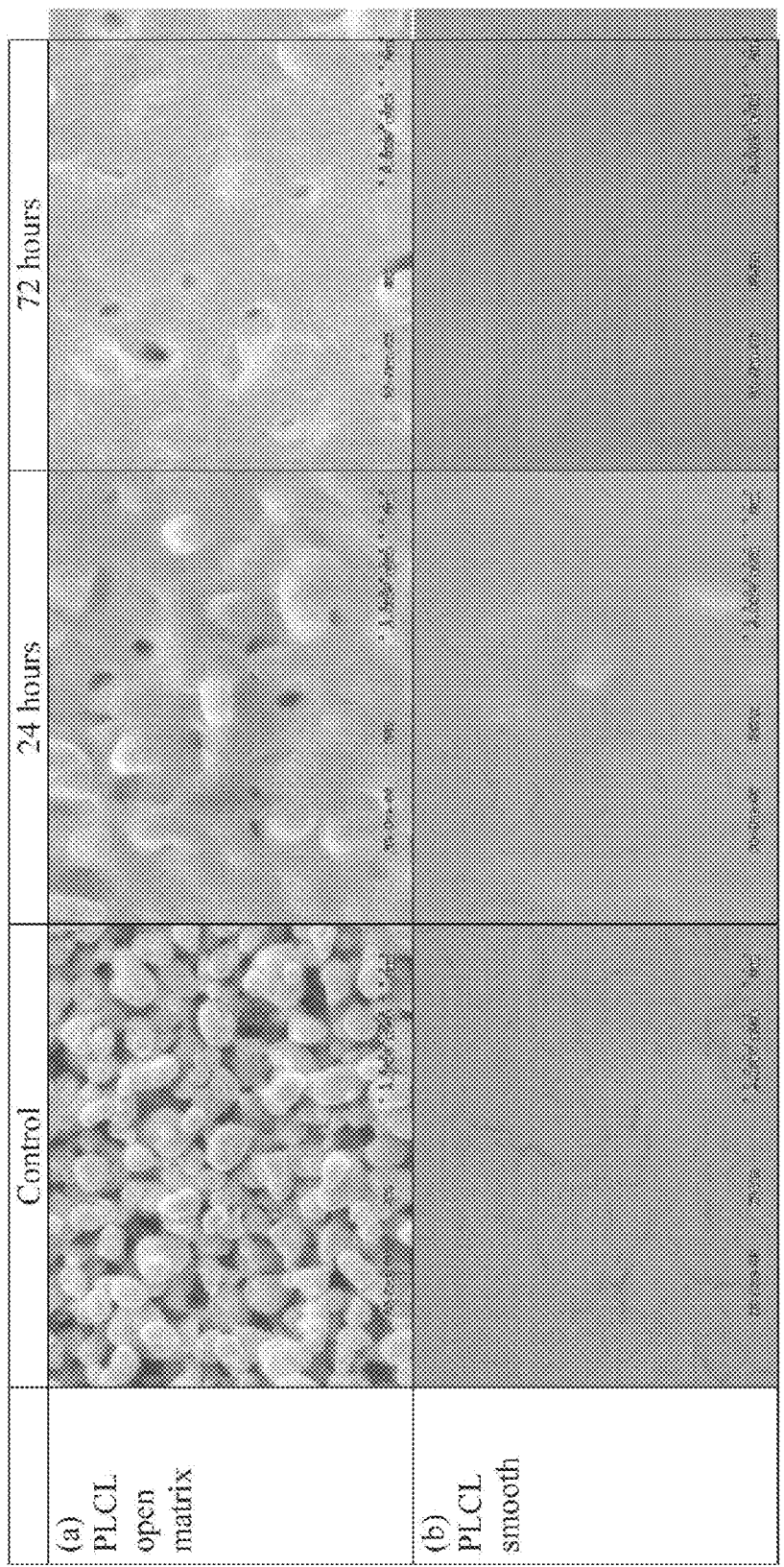
FIGS. 23a and 23b show images of the effect of humidity on open matrix coatings and closed film coatings according to one or more examples provided herein.
Figure 24B:
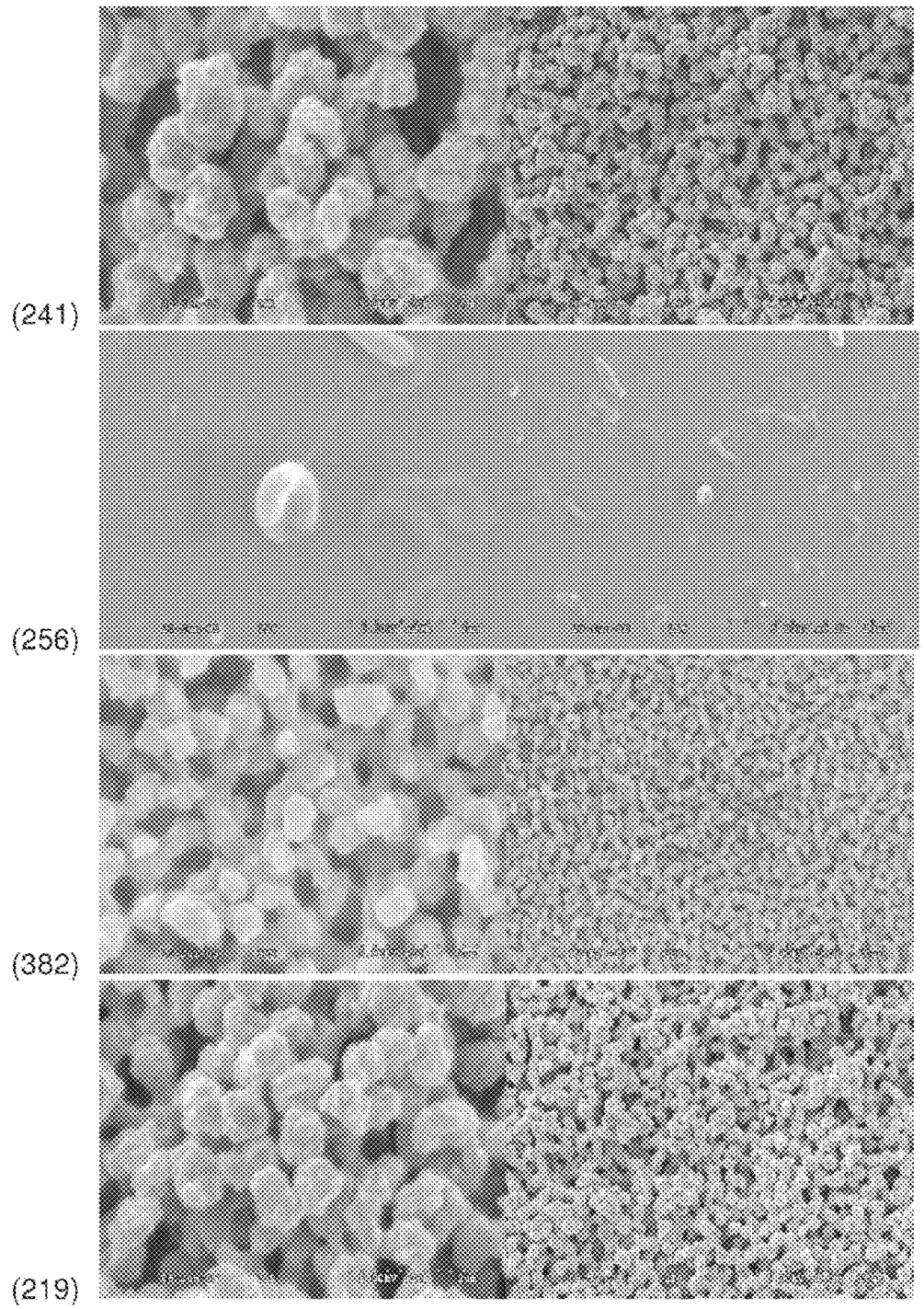
FIG. 24B shows respective images (higher magnification and lesser magnification) of the resulting coatings corresponding to the Sample #'s shown in the table.
Figures 25A, 25B:
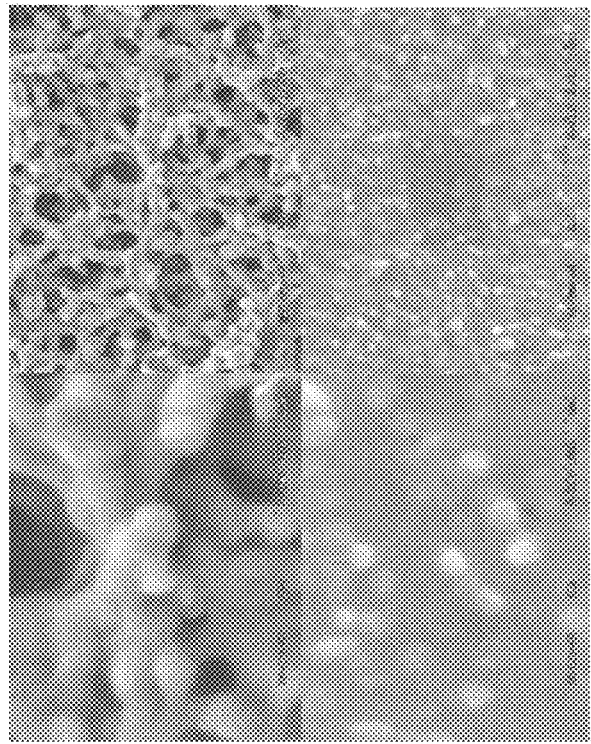
FIG. 25A shows a table of solutions and parameters used in the application of one or more coatings according to one or more examples provided herein.
FIG. 25B shows respective images (higher magnification and lesser magnification) of the resulting coatings corresponding to the Sample #'s shown in the table.
Figures 27A, 27B:
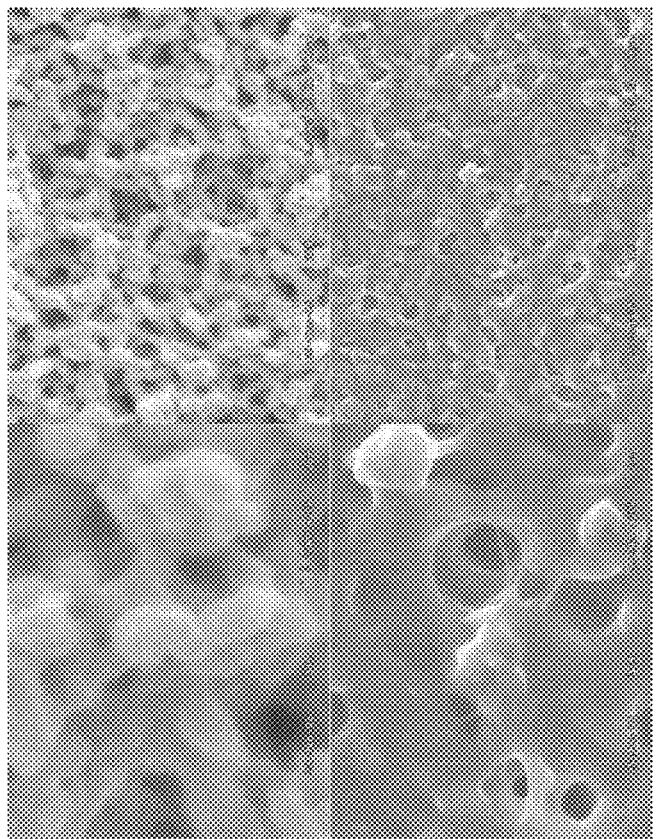
FIG. 27A shows a table of solutions and parameters used in the application of one or more coatings according to one or more examples provided herein.
FIG. 27B shows respective images (higher magnification and lesser magnification) of the resulting coatings corresponding to the Sample #'s shown in the table.
Figures 28A, 28B:
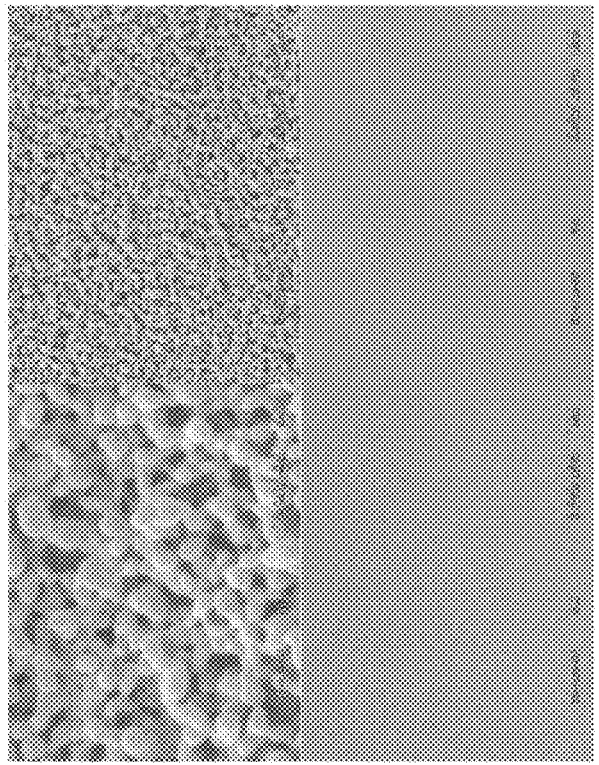
FIG. 28A shows a table of solutions and parameters used in the application of one or more coatings according to one or more examples provided herein.
FIG. 28B shows respective images (higher magnification and lesser magnification) of the resulting coatings corresponding to the Sample #'s shown in the table.
Figures 29A, 29B:
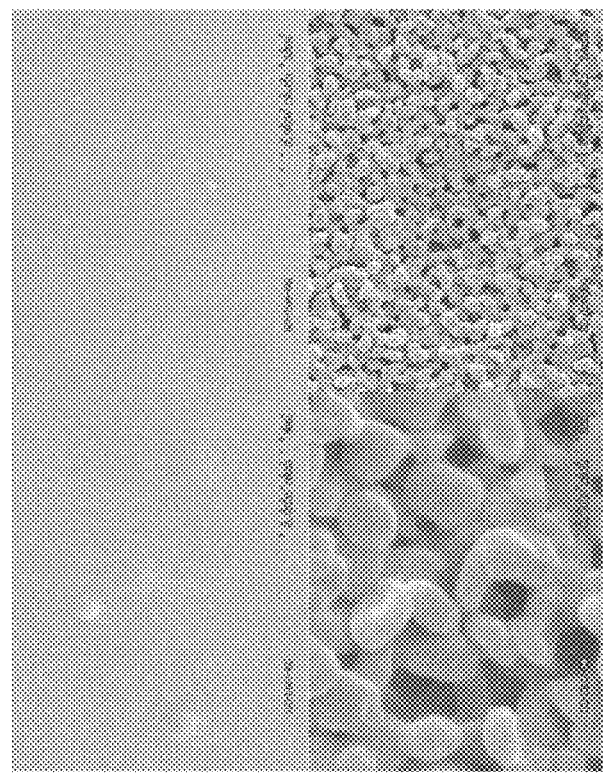
FIG. 29A shows a table of solutions and parameters used in the application of one or more coatings according to one or more examples provided herein.
FIG. 29B shows respective images (higher magnification and lesser magnification) of the resulting coatings corresponding to the Sample #'s shown in the table.
Figures 30A, 30B:
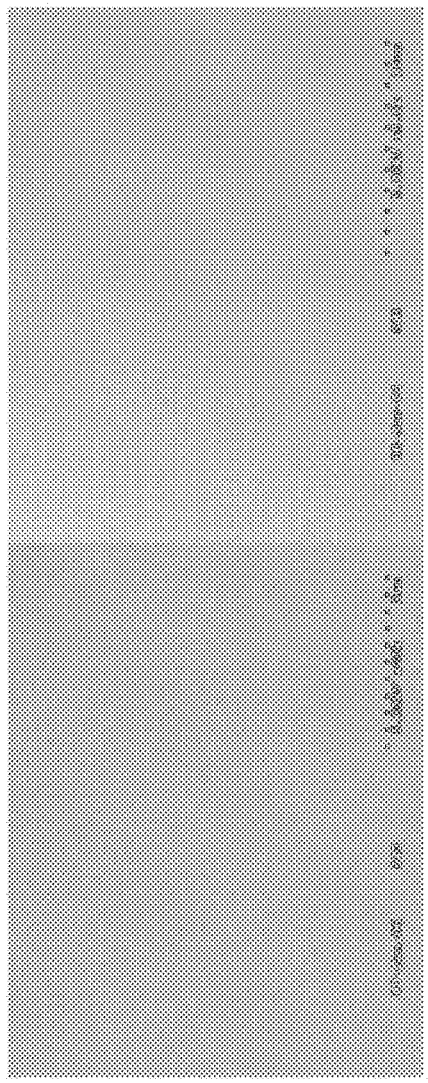
FIG. 30A shows a table of a solution and parameters used in the application of one or more coatings according to one or more examples provided herein.
FIG. 30B shows respective images (higher magnification and lesser magnification) of the resulting coating corresponding to the Sample # shown in the table.
Figures 31, 32:
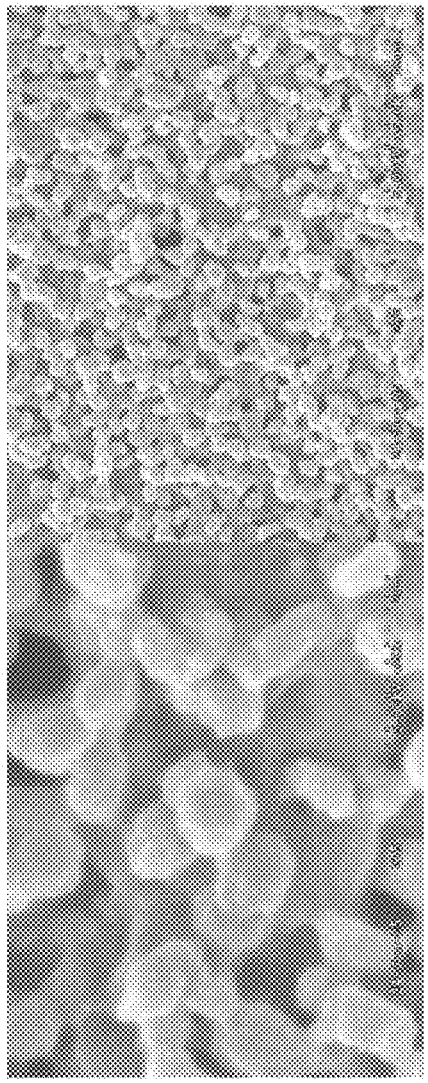
FIG. 31 shows a table of a solution and parameters used in the application of one or more coatings according to one or more examples provided herein.
FIG. 32 shows respective images (higher magnification and lesser magnification) of the resulting coating corresponding to the Sample # shown in the table of FIG. 31.
Figures 33, 34:
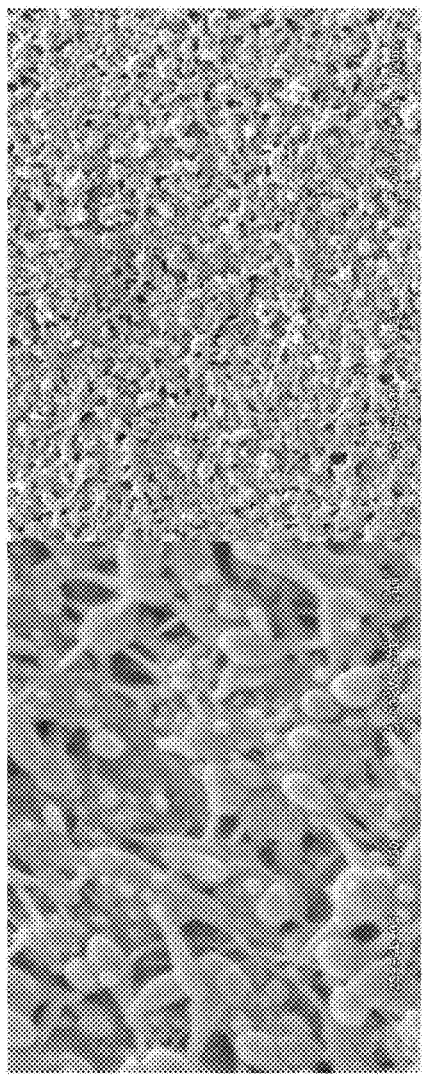
FIG. 33 shows a table of a solution and parameters used in the application of one or more coatings according to one or more examples provided herein.
FIG. 34 shows respective images (higher magnification and lesser magnification) of the resulting coating corresponding to the Sample # shown in the table of FIG. 33.

When stents coated with the PLCL polymer and dexamethasone were exposed to a 99% relative humidity (RH) environment at room temperature, changes in the surface morphology were seen for both the smooth coating and the open-matrix coating, shown in FIGS. 23*a-b*. With the open-matrix coating of FIG. 23*a*, the round particles present in the control stents were no longer distinct by 24 hours and appeared to have become contiguous by either swelling or melting. With the smooth coating of FIG. 23*b*, surface irregularities not present on the control stents appeared as early as 24 hours.

While the PLCL biodegradable polymer provides considerable flexibility in engineering both smooth and particulate surface features, it is very sensitive to environmental moisture. This surface could be a way of supplying a rapid burst of drug release due to the high surface area that is exposed to the points of contact in the vessel.

Other Applied Coating Examples Using Liquid Spray and Diluent Compositions

Using the same electrospray setup described above, various solutions were sprayed to form coatings on objects as shown below. Liquid spray compositions (e.g., solids and solvents) were provided as the inner flow (IF) to the inner opening of the dual concentric opening nozzle structure (i.e., inner capillary) and liquid diluent compositions were provided as the outer flow (OF) to the outer opening of the dual concentric opening nozzle structure as indicated in the tables associated with each example. In each example, images are matched to the table by the Sample #.

Example 1

The solution samples listed in the table of FIG. 24A were sprayed under the conditions provided therein. FIG. 24B shows images of the coatings resulting from the spraying of the samples in cone-jet mode. The images for each solution are provided in higher and lesser magnification. The solution (0.9% poly(styrene-b-isobutylene-b-styrene (abbreviated SIBS)+0.1% paclitaxel (PTx) in 85% tetrahydrofuran (THF) and 14% methanol (MEOH) could be sprayed as open matrix coating. In order to obtain a closed film (smoother) coating, toluene was added into the mixture.

Example 2

The solution samples listed in the table of FIG. 25A were sprayed under the conditions provided therein. FIG. 25B shows images of the coatings resulting from the spraying of the samples in cone-jet mode. The images for each solution are provided in higher and lesser magnification. The solution (0.9% SIBS+0.1% PTx in 99% THF) didn't spray in cone-jet mode initially because of the low conductivity. More volatile and conductive solvent such as methanol was used in outer nozzle so that the open-matrix coating was achieved. Then, the closed film coating was obtained by adding the outer flow and changing the ratio between the inner and outer flow.

Example 3

The solution sample listed in the table of FIG. 26A was sprayed under the conditions provided therein. FIG. 26B shows images of the coating resulting from the spraying of the samples in cone-jet mode. The images for each solution are provided in higher and lesser magnification. The solution (2.25% SIBS+0.25% PTx in 97.5% THF) has high viscosity, which prevented it from being sprayed at cone-jet mode. Solvent blend was introduced into outer nozzle so that the closed film coating was achieved.

Example 4

The solution samples listed in the table of FIG. 27A were sprayed under the conditions provided therein. FIG. 27B shows images of the coatings resulting from the spraying of the samples in cone-jet mode. The images for each solution are provided in higher and lesser magnification. The solution (4.5% SIBS+0.5% PTx in 95% THF) has high viscosity, which prevents it from being sprayed at cone-jet mode. Solvent blend was introduced into outer nozzle so that the open-matrix and the closed film coatings were achieved.

Example 5

The solution samples listed in the table of FIG. 28A were sprayed under the conditions provided therein. FIG. 28B shows images of the coatings resulting from the spraying of the samples in cone-jet mode. The images for each solution are provided in higher and lesser magnification. An open matrix coating could be easily achieved with this solution (4.5% PLCL+0.5% DEX in 95% Acetone) because of the low boiling point and higher conductivity of acetone. In order to have a closed film coating, the acetone and chloroform blend was used as outer solvent.

Example 6

The solution samples listed in the table of FIG. 29A were sprayed under the conditions provided therein. FIG. 29B shows images of the coatings resulting from the spraying of the samples in cone-jet mode. The images for each solution are provided in higher and lesser magnification. Open matrix coating could be easily achieved with this solution (5% PLCL in 95% Acetone) because of the low boiling point and higher conductivity of acetone. In order to have closed film coating, the acetone and chloroform blend was used as outer solvent.

Example 7

The solution sample listed in the table of FIG. 30A was sprayed under the conditions provided therein. FIG. 29B shows images of the coating resulting from the spraying of the sample in cone-jet mode. The image for the solution was provided in higher and lesser magnification. The solution (1.8% PLCL+0.2% DEX in 82% THF and 16% MEOH) didn't spray at cone-jet mode initially. A small amount of methanol was added into outer nozzle to provide some conductivity. A closed film coating was achieved by this way.

Example 8

The solution sample listed in the table of FIG. 31 was sprayed under the conditions provided therein. FIG. 32 shows images of the coating resulting from the spraying of the sample in cone-jet mode. The images for the solution are provided in higher and lesser magnification. MEK has a boiling point of 79-80.5 C, but the conductivity is lower than methanol, which was the reason why this solution (0.9% SIBS+0.1% PTx in 69.7% THF and 29.3% MEK) didn't spray at cone-jet mode initially. A solvent blend of methanol and THF was added into outer nozzle to provide more conductivity. An open matrix coating was achieved by this way.

Example 9

The solution sample (2% DEX in 40% ethanol (ETOH) and 60% ACETONE) listed in the table of FIG. 33 was sprayed under the conditions provided therein. FIG. 34 shows images of the coating resulting from the spraying of the sample in cone-jet mode. The images for the solution are provided in higher and lesser magnification. Unlike the other example 1-10, this solution sample was sprayed using a triple concentric opening nozzle, like that described with reference to FIG. 7B. The triple nozzle was used to encapsulate the drug with the PLCL. Acetone was used at the outermost nozzle.

The apparatus used to spray the coating was equivalent to that shown in and described with reference to FIG. 7A modified with the dual capillary tube distributor head 400 shown in and described with reference to FIG. 7B. The apparatus used was configured with a center capillary tube 413 having an outer diameter of about 558.8 μm (0.022 inches) and an inner diameter of about 304.8 μm (0.012 inches). The second capillary tube 414 concentric with the center capillary tube had an outer diameter of about 1041.4 μm (0.041 inches) and an inner diameter of about 685.8 μm (0.027 inches). The distance dl shown in FIG. 7B from the end of tapered section 335 to the end of the metal casing 322 is about 1143 μm (0.045 inches). The diameter d2 of the first end 336 of the nozzle portion or metal casing 322 is about 6426 μm (0.253 inches). The outer diameter d4 of the second end 338 of the nozzle portion 322 is about 1549 μm (0.061 inches) and an inner diameter d3 of about 889 μm (0.035 inches). The distance d5 from the tip of the second end 338 of the nozzle portion 322 to the tip of the end of the second capillary tube 414 is about 508 μm (0.020 inches). The gap d6 at the tip of the second capillary tube 414 is about 685.8 μm (0.027 inches).

The dispensing device was constructed of various materials. Primarily, the conductive elements were constructed of stainless steel, the apparatus was used in a chamber made of plexiglass, and insulative parts thereof were made of a plastic, black delrin, material. A voltage of 4300 volts was applied to conductive element 312. The distance from the dispensing tip 495 of the second capillary tube 414 to the target was about 8 mm.

The inner capillary flow rate was 0.75 μl/min and the stream contained 2% dexamethasone in a 2:3 blend of acetone and ethanol. The second capillary flow rate was 1.5 μl/min and the stream was 5% PLCL in acetone. The third and outer nozzle flow rate was 5 μl/min and contained acetone only.

Discussion Regarding Results

The electrospray coating system and process proved very flexible. The system was able to apply a range of polymers of differing performance qualities and solvent requirements. For each condition studied, a set of operating parameters was successfully identified that provided a cone-jet spray throughout the coating as well as the desired surface architecture. The system proved to be reliable and flexible enough to accommodate solvents over a range of polarities and conductivities.

A key element to the successful spray operation was the ability to merge solvent streams at the spray tip (e.g., a lower conductivity liquid spray composition including a polymer, drug and suitable solvent with a higher conductivity liquid diluent composition such as one that includes an addition of nitric acid). This feature of the spray nozzle design has permitted us to spray both polar solvents and non-polar solvents of extremely low conductivity.

Important objectives related to scale-up for manufacturing were identified. The system produced even coatings on all intricate surfaces of a stent without webbing or coating voids. Coating weights were uniform within a tight range during lot production. Reproducible coatings were produced with different surface characteristics, including the preservation of particle architecture. The strikingly different coating types achieved with PLCL polymer, just by altering the spray operating parameters, were noteworthy. The open-matrix coating has a much greater surface area and would be presumed to alter drug release characteristics. This open matrix coating with its preserved nanoparticulate architecture, which we have now been able to replicate with two polymers having very different solvent requirements, is desirable, including potential variations that combine more than one active ingredient applied jointly or individually to create unique pharmacokinetics.

In view of the experiments, various modifications for the spray apparatus may be made to so as to include monitoring and controlling the process in view thereof with respect to any of the following: surface dust and fibers that contaminated the spray surface; imprecise controls on gas flow and composition through the spray chamber; inadequate evaporation rates of solvents; temperature fluctuations in ambient air; humidity fluctuations in ambient air; the need to eliminate gas bubbles from the spray feed material; the need to adjust the voltage of the power supply manually; need of bright lighting for video imaging and impact of ultraviolet light on cure of certain polymers; overspray of polymer and potentially toxic drug material and inability to clean all surfaces of the spray chamber without dismantling it; and build-up of coating overspray on the fixture leading to changes in the voltage settings required to operate in cone-jet mode.

For example such modification may include additional mechanisms to provide management of air or gas stream quality flow through improved filtration, temperature and moisture control, as well as flow rate controls. Improved control features will also enable operators to modify or facilitate solvent evaporation by improved temperature and gas control.

Yet further, automation of voltage control may be used. For example, such automation may include video imaging assessment of the cone-jet(s) during operation and, where indicated, feedback adjustments and/or immediate termination of spray operations. For example, if the cone-jet becomes unstable and begins to "spit," this can result in discharge of excessive solvent and cause blemishes on the coated surface. The "spit" can be seen visually and the effects reduced by stopping the spray or masking the spray surface, but there is often insufficient time to react. It should be possible through image monitoring and analysis to limit or prevent the impact on the spray surface and make needed process control modifications. Yet further, improved light sources may be used, with the possibility of limiting certain wavelengths, and three-dimensional video camera positioning for better imaging of both the target and cone-jet may be used. Further, placing a moving stage and/or spray head parts outside of the actual spray chamber may be used to improve cleanability and the ability to contain more toxic spray elements during spray operations.

Still further, material containment and safe handling as well as treatment of the vented air or other gases passing through the spray chamber may be used to remove any stray particles.

References cited in the Examples above include:

Alexis F, Venkatraman S S, Rath S K, Boe F. In vitro study of release mechanisms of paclitaxel and rapamycin from drug-incorporated biodegradable stent matrices. J Controlled Release 98:67-74 (2004).

Chen D-R, Pui D Y H, Kaufman S L. Electrospraying of Conducting Liquids for Monodisperse Aerosol Generation in the 4 nm to 1.8 m Diameter Range, *J Aerosol Sci,* 26(6) 963-977 (1995).

Puskas J E, Chen Y, Dahman Y, Padavan D. Polyisobutylene-Based Biomaterials. Feature Article. J. Polym. Sci., Chem., 42(13):3091-3109 (2004).

Ranade S V, Miller K M, Richard R E, Chan A K, Allen M J, Helmus M N. Physical characterization of controlled release of paclitaxel from the TAXUS™ Express$^{2}$™ drug-eluting stent. J Biomed Mater Res 71A:625-634 (2004).

Szycher M, Armini A, Bajgar C, Lucas A. Drug-eluting stents to prevent coronary restenosis. (www.implantsciences.com/pdf/IMXpaperv2-rev2.pdf) (2002)

Verhoeven M L P M, Driessen, A A G, Paul A J, Brown A, Canry J-C, Hendriks M. DSIMS characterization of a drug-containing polymer-coated cardiovascular stent. J Controlled Release 96, 113-121 (2004).

Timed Drug Release Embodiments

A coating that includes one or more drugs may be applied to many different types of surfaces with an open or closed matrix as a function of spraying parameters. In one embodiment, the surface of a pre-formed, hydrated hydrogel polymer surface using ElectroNanospray may be coated with a drug containing layer with various drug sustained release profiles.

In one embodiment, a coating of drug and polymer may be applied to the surface of a pre-formed, hydrated hydrogel polymer surface using electronanospray, resulting in a coating which provided sustained release of the drug over 1 to 2 weeks.

In one embodiment, a drug, especially a hydrophobic drug, may be applied to the surface of the hydrogel in nanoparticle form such that it adheres to the surface. In a second embodiment, a drug and polymer combination may be applied to the surface of the hydrogel, also in nanoparticle form, such that the combination adhered to the surface and provided a sustained release of drug from the hydrogel for an extended period. In one embodiment, the sustained release of the drug from the hydrogel was for longer than 24 hours.

Typically, hydrogels have been used to deliver drugs by incorporating them directly into the hydrogel matrix. Hydrogels themselves, with or without drug loading, have also been used as coatings on different types of implants.

Example

Hydrogel discs, <1 cm in diameter and <1 mm in thickness, were provided by a third party. The hydrogel was removed from a buffer in a fully hydrated state, placed upon a grounded target, and its surface sprayed with drug and solvent alone or a mixture of a biodegradable polymer such as Poly(DL-lactide-co-ε-caprolactone, 80/20) (PLCL) and drug (dexamethasone) in a ratio of 10:1 using ElectroNanospray. Other hydrogel material may be used with likely similar results. Soft contact lenses of varying compositions are examples of such additional hydrogel materials.

As shown in FIG. 1 (and in further detail in FIGS. 7A and 7B with different reference numbers), one example embodiment of an electrospray coating system 10 employs a dispensing apparatus 19 to establish a spray of coating particles 28 (e.g., spray of microdroplets which evaporate to form a spray of coating particles). The dispensing apparatus 19 includes at least one nozzle structure 18 that includes at least two concentric openings 27, 29 (e.g., concentric about axis 39) that terminate at the dispensing end 23 thereof. A drug and polymer combination in solvent may be delivered in the inner concentric opening 27 of the dual capillary spray nozzle, and a solvent alone may delivered in an outer concentric opening 29 of the nozzle in one embodiment. Various spray conditions were evaluated using a design of experiments matrix approach, using either a 2%/0.2% mixture of PLCL and dexamethasone or a 5%/0.5% mixture.

After spraying, the discs were placed in a 10 ml volume of phosphate buffered saline and incubated on a shaker bath at 37 degrees C. Buffer was removed and replaced at various time intervals, starting as early as 1 hour after incubation up to 14 days. The removed buffer was assayed by high performance liquid chromatography (HPLC) for dexamethasone concentration and the amount of drug released into the incubation medium over the time span since the previous sample was calculated. These results were plotted as a function of time and dexamethasone mass in micrograms. The methods and results are detailed below in a summary.

In various embodiments, the hydrogel can be preformed in its final configuration (i.e. not prior to polymerization); the degree of drug loading can be controlled; the drug can be applied as a nanoparticulate matrix; the drug can be encapsulated in a biodegradable, bioerodable polymer that is also applied to the hydrogel's surface; this coating can result in gradual release of the drug from the hydrogel's surface. The drug need not be eluted quickly from the hydrogel's surface despite maintenance of the hydrogel in an aqueous buffer solution.

The method and device may be used to provide antimicrobial treatment or anti-inflammatory treatment to an implant or surface applied hydrogel (e.g. contact lens) that has a dwell time of one day or longer as a means of making the hydrogel use safer or less irritating to the body. It may also be used as a means of applying an implantable or topical therapy of another sort. For example, hydrogels are being discussed as possible replacements for metallic coronary stents. An anti-inflammatory compound such as a steroid (e.g., dexamethasone), a nonsteroidal antiinflammatory agent (e.g. ibuprofen or indomethacin), an antiproliferative agent (e.g. paclitaxel or rapamycin) may be applied to the hydrogel prior to implantation to prevent scarring at the site of implantation. Other antiproliferative or antiinfective drugs may also be used.

Nanoparticle Coatings on a Hydrogel Surface Resulting in Sustained-Release of Drug into an Aqueous Medium Hydrogel discs, similar in flexible contact lens material in appearance and flexibility, may be coated with a poorly water-soluble antifungal agent, griseofulvin, using ElectroNanospray. Control images were developed for the hydrogel to determine its underlying structural appearance using SEM cryostage imaging. Hydrogel appears to form a good target for the spray process. Particles were adherent to the surface with preserved nanoparticulate architecture. Several images are provided to illustrate to support these statements.

Figure 35A:
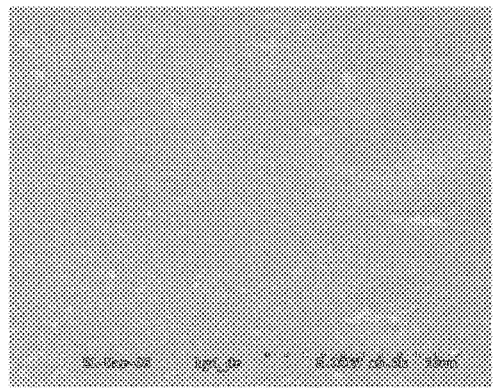
FIGS. 35A and 35B are SEM images of a dried hydrogel with no drug coating according to an example embodiment.
Figure 35B:
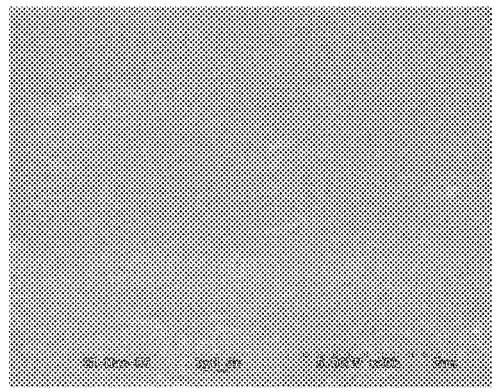

In one embodiment, hydrogel specimens were imaged using SEM. One was air dried, mounted onto an aluminum stud, and sputter-coated with gold for 90s. FIGS. 35A and 35B are different magnifications of an example sample image of dried hydrogel with no drug coating. This sample was relatively smooth with minor surface defects.

Figure 36A:
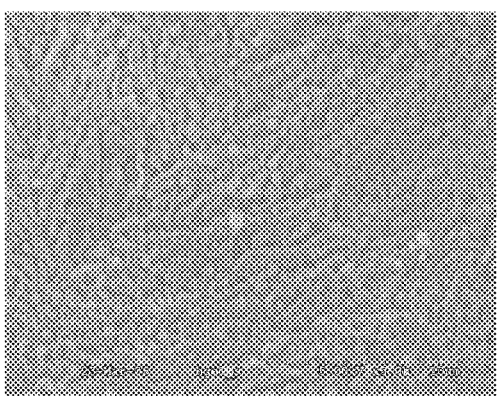
FIGS. 36A and 36B are SEM images of a moist hydrogel with no drug coating according to an example embodiment.
Figure 36B:
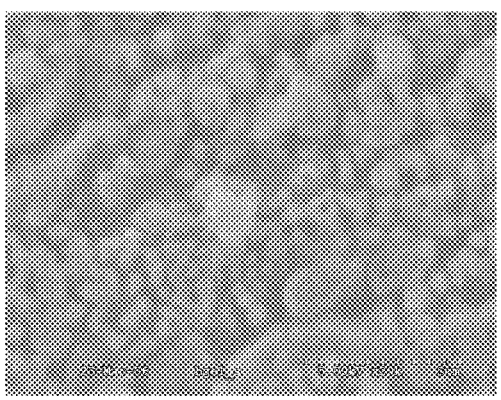

For imaging the hydrated gel sample, a cryostage technique was used. The hydrogel sample was first equilibrated in deionized water for 24 h at room temperature and then very quickly frozen using liquid nitrogen. Imaging of the frozen moist sample with no drug coating is shown with different amplifications in FIGS. 36A and 36B and was taken at 5.0 kV. This image showed a finely particulate surface that may represent ice crystals.

Figure 37A:
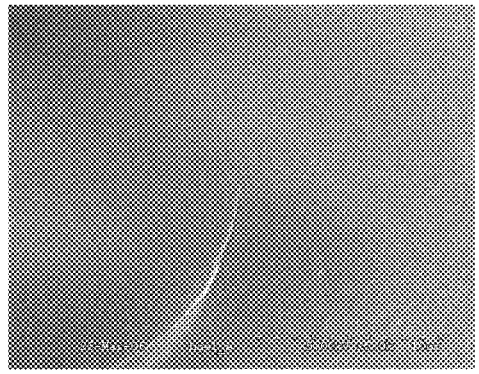
FIGS. 37A and 37B are SEM images of a freeze-fractured hydrogel with no drug coating according to an example embodiment.
Figure 37B:
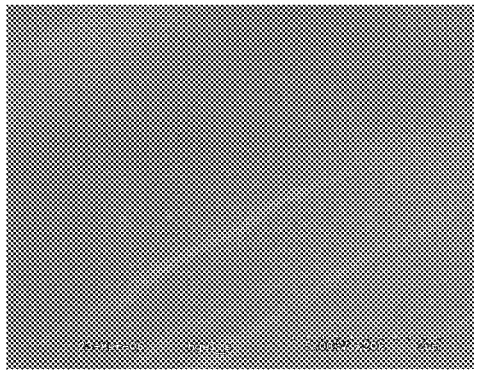
Figure 38A:
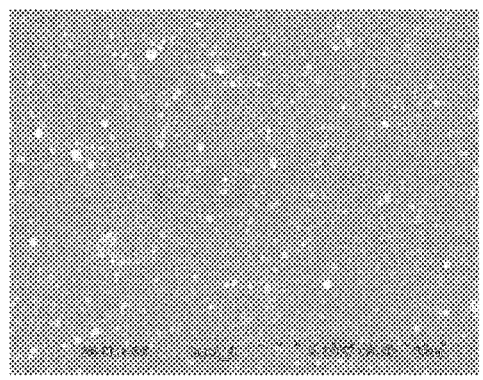
FIGS. 38A and 38B are SEM images of a freeze-dried hydrogel with no drug coating according to an example embodiment.
Figure 38B:
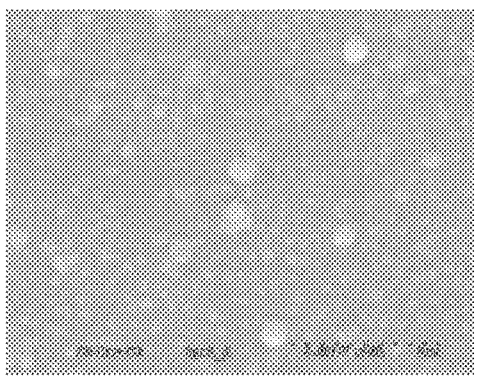

Cryofracturing of the frozen specimen was done to obtain a cross-sectional interior view. The frozen specimen was fractured with a sharp scalpel, then sputter-coated with gold for 480 s (FIGS. 37A and 37B). This image showed a homogeneous, smooth matrix. A second specimen was freeze dried until all of the resident water was sublimed, then sputter-coated with gold for 480 s (FIGS. 38A and 38B). This image showed fewer, more widely space particles on the surface. All imaging was performed at 5.0 kV.

Drug Coating Examples

For initial feasibility spray examples, griseofulvin (0.09023 g), a poorly water soluble antifungal agent, was dissolved in a mixture of ethanol (9 ml) and acetone (6 ml). A hydrogel sample, approximately 5 mm in largest diameter, removed from a borate buffer solution and placed on a metallic spray platform beneath the ElectroNanospray device's dual capillary spray head. The solution was sprayed in the cone jet mode at 4.17 kV at 5 µl/min and a distance of 15.6 mm from the hydrogel. Spray time was 20 minutes. The surface pattern seen in the SEM image shown in FIGS. 39A and 39B show a uniform, closely packed surface of approximately 200 nm particles at 20,000× magnification.

For comparison purposes, an image of a stainless steel plate coated with griseofulvin is shown in FIGS. 40A and 40B. The particles are more clumped together in grape-like clusters, but approximately the same size as those seen in FIGS. 37A and 37B.

Based on the successful demonstration that nanoparticles of the hydrophobic anti-fungal drug griseofulvin may be applied to the hydrogel material with ElectroNanospray, a coating that provides sustained release of a model drug from the hydrogel over a minimum of 1 day or longer may be obtained.

Figure 41:
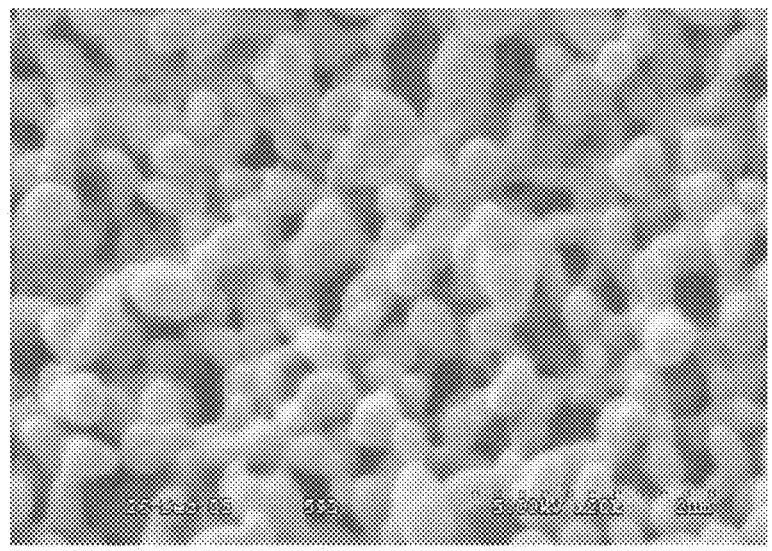
FIG. 41 is an SEM image of a surface coating morphology with PLCL/dexamethasone combination according to an example embodiment.

In one embodiment, a polymer stabilizing material may be used to help control drug release. Dexamethasone provides a reasonable model drug for example. Spray methods for the combination of the biodegradable polymer, poly(DL-lactide-co-ε-caprolactone, 80/20) or PLCL, and the steroid anti-inflammatory agent dexamethasone were performed, and HPLC analytical methods were used for measuring dexamethasone release over time. One example image of a surface coated based on this model system is shown in FIG. 41. This image was taken from a generic stainless steel coronary stent coated with dexamethasone and PLCL. Note the open matrix particulate nature of the surface morphology. This is even more open than the previously shown image of the gel coated with griseofulvin. This coating has been remarkably consistent on a wide range of substrates.

Figure 42:
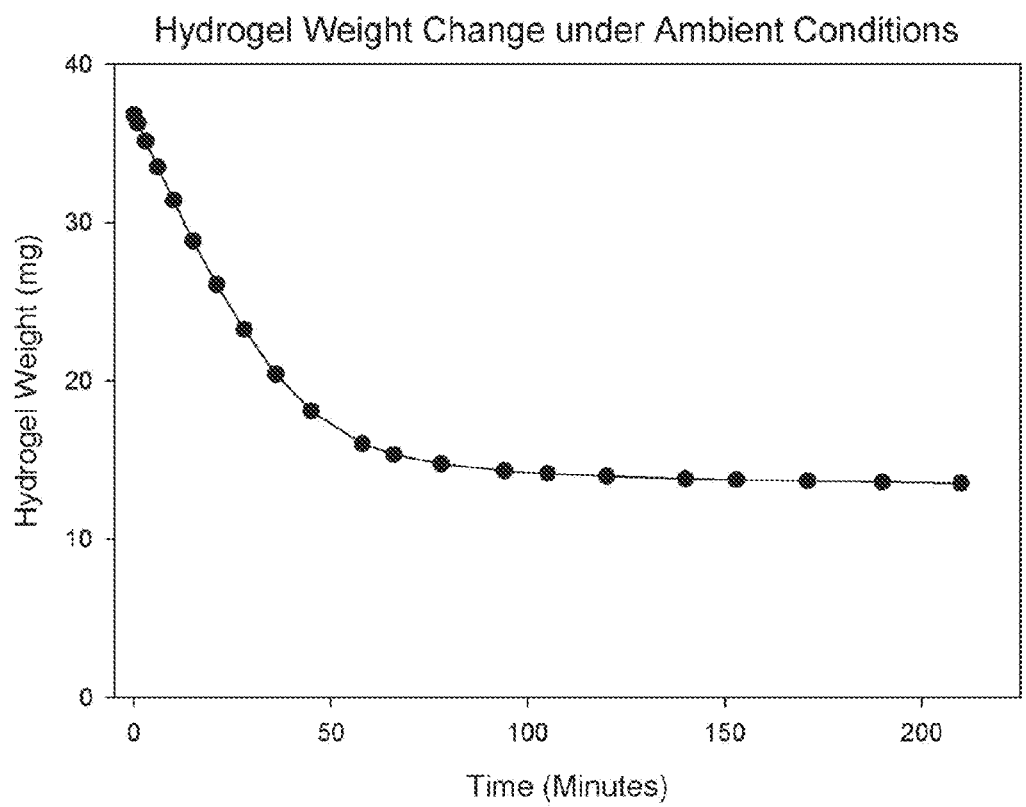
FIG. 42 is a graph illustrating hydrogel weight change under ambient conditions.
Figure 43:
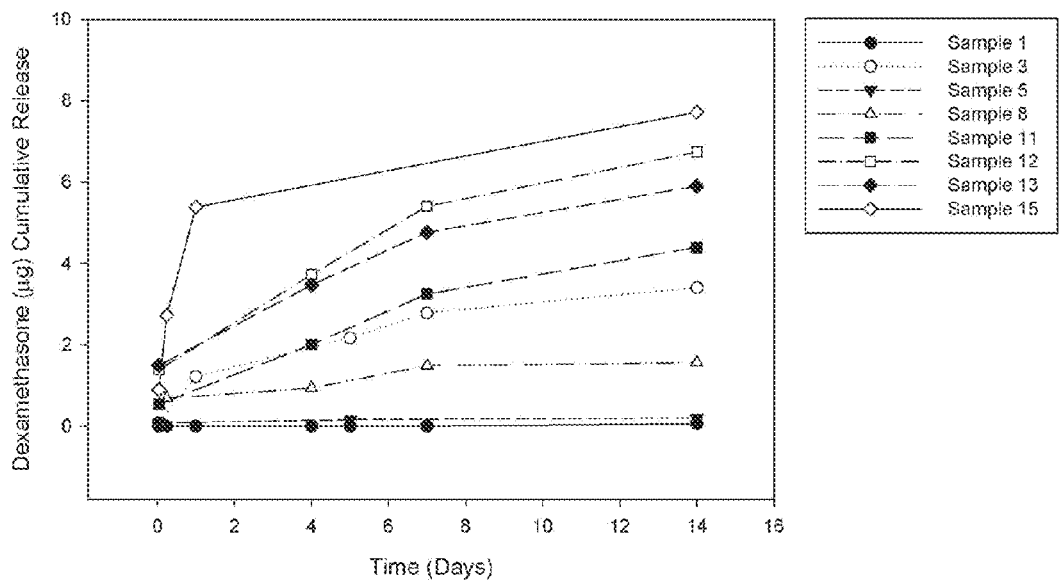
FIG. 43 is a graph illustrating release of dexamethasone in µg from coated hydrogel samples over a 14 day period in accordance with example embodiments.
Figure 44:
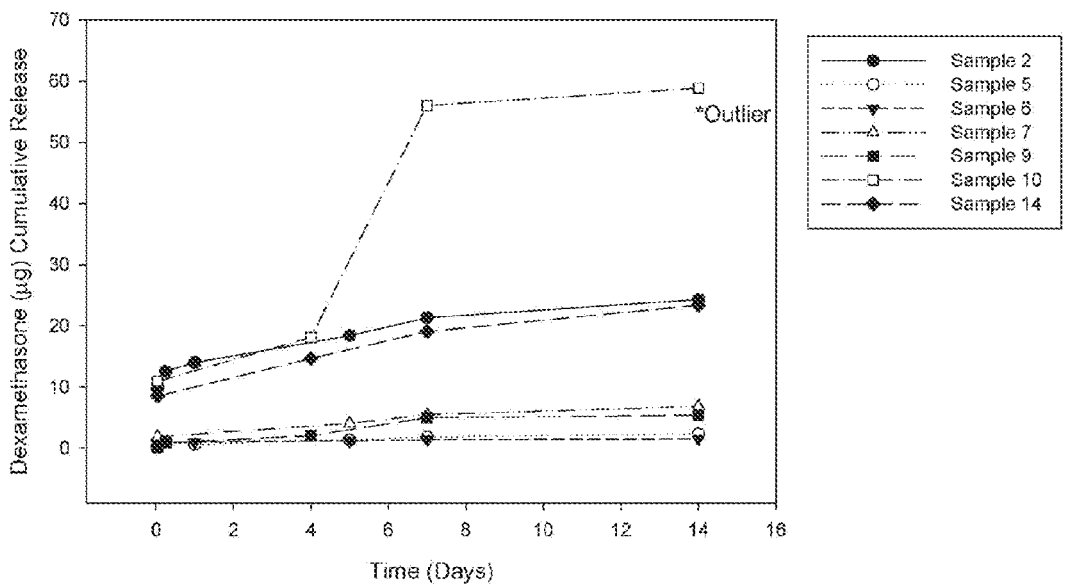
FIG. 44 is a graph illustrating release of dexamethasone in µg from a coated hydrogel samples over a 14 day period in accordance with example embodiments.

Preliminary studies showed that the hydrogel material dried quickly under ambient conditions. A control experiment was run to determine the approximate rate of weight change as shown in FIG. 42 (weight change of a hydrogel sample over 210 min at room temperature) of the hydrated gel under ambient conditions. All measurements were taken by weighing the hydrogel after first blotting away the surface moisture. Results show that the hydrated gel loses weight fairly quickly over the first 30 mins and thereafter at a slower rate. Inability to control for this weight change makes weight an unreliable indicator of drug loading achieved during spray coating. In further embodiment, a uniform procedure may be used for controlling parameters such as temperature, humidity, handling time, to control hydrogel sample weight change under identical conditions.

Experimental Protocol for Drug Release Studies

Spray experiments were then designed to determine if spray coating conditions could (a) apply dexamethasone and PLCL to the surface of the hydrogel and (b) how changes in those parameters affected the rate of release from the surface. In one embodiment, a prolonged release pattern may be desired rather than a "burst" of drug release in the first few hours.

Materials.

The polymer poly(DL-lactide-co-s-caprolactone, 80/20) (PLCL), inherent viscosity 0.77 dL/g in chloroform, was purchased from Absorbable Polymers International, Pelham, Ala., USA. Dexamethasone (99% purity) was purchased from Alexis Biochemicals, San Diego, Calif., USA. Hydrogel discs similar to soft contact lenses in appearance and flexibility were obtained in buffer solution. These were placed in phosphate buffered saline (PBS) and maintained at 4° C. until the day of the coating experiments, when they were brought to ambient temperature in the buffer. Two different concentrations of polymer/drug were used: 2% PLCL/0.2% dexamethasone and 5% PLCL/0.5% dexamethasone.

Spray Experimental Design.

A Design of Experiment (DOE) matrix (established with Design Expert 7.0, Stat-Ease) was established to determine (a) "best" set of operating conditions and (b) the effect of various changes in spray operating parameters on the coating weight of drug that was achieved. The matrix is outlined in Table 1, below, where Block equals day of spraying and Columns C1 through C3 refer to spray parameters (distance from spray head to target, flow through the inner capillary, and flow through the outer capillary, respectively). Two different conditions were evaluated for each parameter, as indicated by letters in each column. Column C4 refers to the percentage of polymer that was used (2% or 5%).

Quantifying Drug Loading on the Hydrogel Sample.

Because the underlying weight of the gel was not stable, as shown in the previous image, a method other than weight may be used for estimating the amount of drug that was deposited for each set of the parameters in the DOE matrix. In one embodiment, duplicate samples were coated, and for each sample coated for separate release studies, another sample was coated under the same conditions and then soaked in 1 ml acetonitrile solvent for 24 h to extract the drug. Aliquots of this extraction solvent were then quantified for dexamethasone using HPLC. These are the weights reported in the last column of Table 1, below, showing the DOE matrix. Note: sample 10 is an extreme outlier.

Table 1. DOE matrix outlining parameter variations used during the spray experiments and final gel sample drug coating weight, as measured by solvent extraction.

| Gel # | Block (Day) | C1 Distance from spray head to target (mm) | C2 Flow through the inner capillary (µl/min) | C3 Flow through the outer capillary (µl/min) | C4 Concentration of polymer and drug (percent) | Drug loading of dexamethasone (µg)* on individual samples |
|---|---|---|---|---|---|---|
| 1 | Tuesday | 16 | 1 | 2 | 2.0/0.2 | 1.9 |
| 2 | Tuesday | 8 | 1 | 2 | 5.0/0.5 | 4.2 |
| 3 | Tuesday | 8 | 5 | 2 | 2.0/0.2 | 3.8 |
| 4 | Tuesday | 8 | 5 | 5 | 5.0/0.5 | 6.5 |
| 5 | Tuesday | 8 | 1 | 5 | 2.0/0.2 | 1.9 |
| 6 | Tuesday | 16 | 5 | 2 | 5.0/0.5 | 1.0 |
| 7 | Tuesday | 16 | 1 | 5 | 5.0/0.5 | 7.1 |
| 8 | Tuesday | 16 | 5 | 5 | 2.0/0.2 | 3.2 |
| 9 | Wednesday | 8 | 1 | 5 | 5.0/0.5 | 1.8 |
| 10 | Wednesday | 8 | 5 | 2 | 5.0/0.5 | 142.9 |
| 11 | Wednesday | 8 | 1 | 2 | 2.0/0.2 | 10.7 |
| 12 | Wednesday | 16 | 5 | 2 | 2.0/0.2 | 16.9 |
| 13 | Wednesday | 8 | 5 | 5 | 2.0/0.2 | 15.1 |
| 14 | Wednesday | 16 | 5 | 5 | 5.0/0.5 | 34.1 |
| 15 | Wednesday | 16 | 1 | 5 | 2.0/0.2 | 11.6 |
| 16 | Wednesday | 16 | 1 | 2 | 5.0/0.5 | n/a |

Drug Release Studies.

Samples for release studies were placed in PBS and incubated on a shaker platform at 37° C. The buffer was removed and replaced at various time points over the first day and the following two week period. Removed buffer was analyzed for dexamethasone concentration using HPLC. For this, a Hewlett Packard Model 1090 HPLC was used, fitted with a narrowbore column (Zorbax SB C-18, 2.1 mm i.d.×150 mm, 3.5 µm) and UV detector. Data integration and processing were performed with Agilent ChemStation software (Rev. A.08.03). Peak areas were obtained by subtracting the baseline (from a "blank" injection of the sample matrix) from the experimental chromatogram. Dexamethasone was analyzed with the following method: 20/80 to 100/0 to 20/80 acetonitrile/water in 3 min and 3.01 min at 0.6 mL/min, end run at 6 min; 65° C.; 10 µL injection volume. Dexamethasone, which was detected at 243 nm, eluted at 2.27 min. The calibration curve for dexamethasone generated with seven standard concentrations ranging from 0.5 to 30 µg/ml in acetonitrile was adequately linear ($R^2$=0.9999) and the limit of quantification (LOQ) was 0.5 µg/ml.

Drug Release Results: The two graphs, FIGS. 41 and 42 illustrate dexamethasone release over a 14-day period, grouped by the concentration of dexamethasone used in the spray experiment matrix. FIG. 41 is a graph showing release of dexamethasone (µg) from the coated hydrogel samples over a 14 day period. Concentration of PLCL polymer was 2% and concentration of dexamethasone was 0.2% in the spray fluid of the inner capillary. Acetone was the solvent.

FIG. 42 is a graph showing release of dexamethasone (µg) from the coated hydrogel samples over a 14 day period. Concentration of PLCL polymer was 5% and concentration of dexamethasone was 0.5% in the spray fluid of the inner capillary. Acetone was the solvent.

Conclusions: The examples demonstrate that a moist hydrogel specimen can be coated with an electrospray process operating in the cone jet mode, in which drug and polymer nanoparticles are deposited onto the surface. The coating thus applied permits sustained release of the drug into an aqueous medium for at least up to two weeks, which was the limit of the duration of testing in these experiments. Presumably, because the slope does not approach zero for these samples, drug release may continue for a longer period of time.

The implications are that a hydrogel, either implanted or surface applied, such as a contact lens, may be coated with a material that bonds sufficiently to its surface and incorporates a therapeutic agent, e.g. antimicrobial, anti-inflammatory, anticancer, antithrombotic, etc., that can be released slowly from its surface and enable targeted delivery of the material. This means that rather than incorporating the material into the matrix of the hydrogel, the hydrogel could be pre-formed and coated later with the desired therapeutic agent.

In further embodiments, open (relatively rough) and closed (relatively smooth) matrix coatings may be formed to provide different drug release profiles. The coatings may be engineered to provide a desired specific drug release profile. Types of coatings may also be varied in terms of single type of coating or hybrid types of coating to provide rapid versus delayed release.

In still further embodiments, different polymers, or polymeric materials may also be used in the coating processes. Polyurethane, poly(lactide-co-caprolactone), isobutylene copolymers and other polymeric materials may also be used.

While the drug, dexamethasone was used in some of the examples, other drugs such as, for example, paclitaxel or other drugs may also be used. Combinations of two or more drugs may also be provided in a single coating. In yet further embodiments, different drugs may be applied in different types of coatings on the same substrate, such as single and hybrid coatings to obtain multiple release profiles.

Various metallic and non-metallic surfaces (substrates) may also be coated with open and closed matrix coatings. Such substrates in various embodiments include but are not limited to stainless steel, foamed tantalum, hydrogel (in both dry and hydrated state), plastic (polymeric) materials. The coatings which may be applied to such substrates include but are not limited to poly(lactide-co-caprolactone), arborescent polyisobutylenes (arbPIBS), and hydrophobic drugs (dexamethasone).

In some embodiments, various methods of charging the surface to enable coatings to both spray and bind to surfaces are utilized. An ionizer may be used to charge a surface with negative (positive) charge. Positive and negative particles may be sprayed from adjacent spray heads as described below. Successive passes with positive and negative spray streams may also be performed. Conductive elements (carbon black) may be embedded in the polymer to enable partial grounding of the sample, enabling an electric field to be established.

Alternately Charged Samples

Figure 45A:
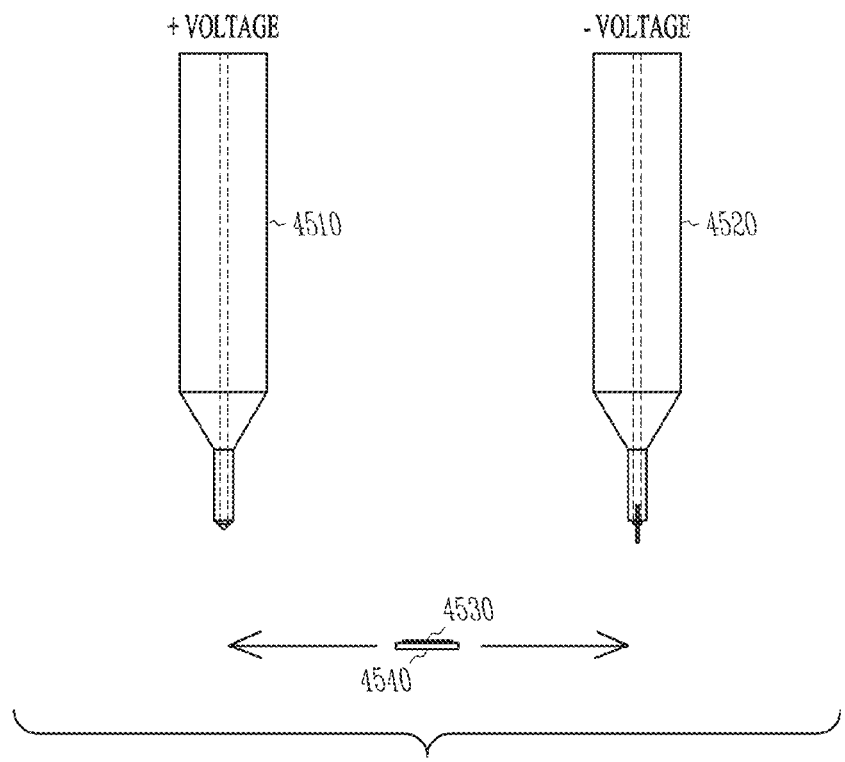
Figure 45B:
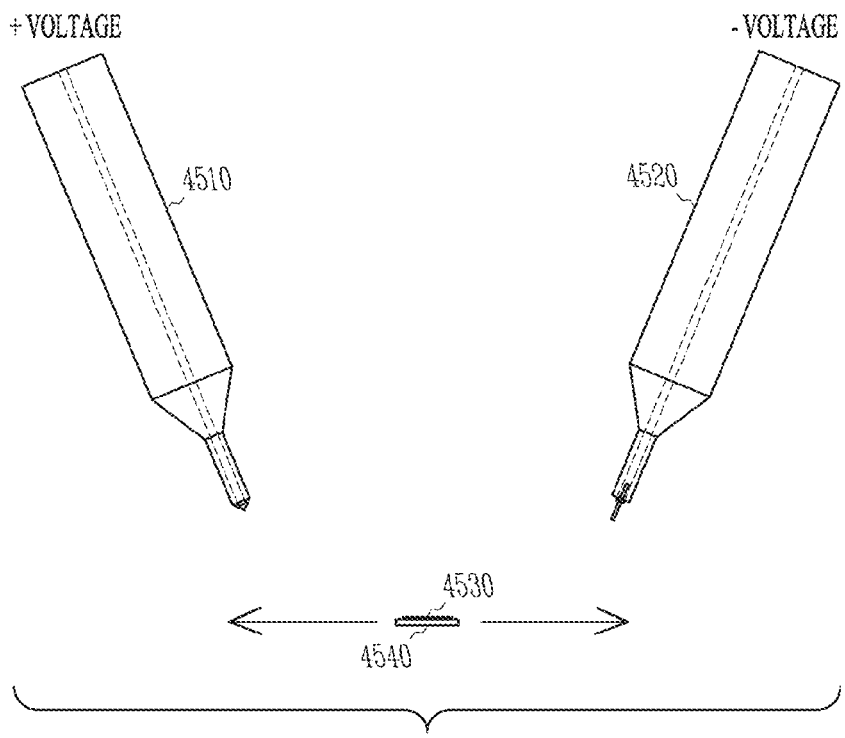

In one embodiment, non-conductive materials, such as a plastic may be coated using one or more spray heads to alternately charge a surface of a sample to be coated. Block schematic diagrams of various multiple spray head arrangements are illustrated in FIGS. 45A, 45B and 45C. A first sprayhead 4510 and a second sprayhead 4520 are illustrated as directed toward a sample 4530 to be sprayed. Motion of the sample is illustrated by arrows proximate the sample in the various figures. In various embodiments, the sprayheads include coaxial concentric openings for delivering different fluids to a spray. They may be the same or similar to those shown in FIG. 1 and FIGS. 7A and 7B.

In FIG. 45A, the sprayheads 4510 and 4520 are illustrated as substantially parallel to each other and are approximately the same distance from the sample 4530, which is located beneath their nozzles. In one embodiment, the motion of the sample is orthogonal to the sprayheads, but may also represent a relative motion between the sprayheads and the sample, one or both of which may be moved to provide such relative motion.

In one embodiment, the sprayheads are spaced apart a sufficient distance such that their sprays do not interact prior to reaching the sample. In further embodiments, the distance is minimized, or may be increased depending on space constraints in the context of use. In further embodiments, the sprays from each of the sprayheads may be alternated in time with some or no overlap, allowing a closer spacing of the sprayheads if desired.

In FIG. 45B, the sprayheads 4510 and 4520 are angled inward to point toward the sample. In one embodiment, the angle between them as approximately 45 degrees, but may be varied between parallel as in FIG. 45A to even greater than 45 degrees.

In FIG. 45C, the sprayheads 4510 and 4520 are positioned opposite each other from the sample 4530, which rotates while being sprayed.

Example One for Non-Conductive Surface Spraying

Two sprayheads were mounted in the machine side-by-side 12 mm to 20 mm apart. Sprayheads were either pointed straight down or at a 45 degree angle to each other. Sprayhead #1 had a positive high voltage charge and had polymer solution dispensed to it. Sprayhead #2 had a wire inserted in the inner capillary (electrode) and had a negative high voltage charge. Sprayhead #2 basically became a high voltage electrode. The plastic cover slip was mounted to a ½" wide grounded piece of stainless steel (reference number 4540) approximately 12 mm below sprayhead. The coverslip was moved back and forth (y-axis) from under sprayhead #1 to sprayhead #2. The result was a coating of polymer on the coverslip. The coating was more even if the plastic was moved in the x-axis under the sprayhead. This method also would if the polarity of the sprayheads was switched, as long as one was positive and one was negative.

The plastic became positively charged under sprayhead #1 and negatively charged under sprayhead #2 so when the plastic went under sprayhead #1 again the polymer particles were attracted to the plastic coverslip.

Example Two for Non-Conductive Surface Spraying

Two sprayhead were used, sprayhead #1 was pointing straight down over coverslip which was mounted on a 0.5" diameter rotating grounded cylinder (reference number 4550). The distance from the tip of the sprayhead to the top edge of the cylinder was approximately 10 mm Sprayhead #1 had a positive high voltage charge and had a polymer solution dispensed to it. Sprayhead #2 was pointing straight up under the cylinder mounted rotating coverslip. The distance from the tip of the sprayhead to the bottom edge of the cylinder was approximately 10 mm. Sprayhead #2 had a negative high voltage charge and had a non-polymer solution dispensed to it. The rotating cylinder was run through the sprayheads in the x-direction slowly back and forth.

The plastic became positively charged under sprayhead #1 and negatively charged under sprayhead #2, so when the plastic went under sprayhead #1 again, the polymer particles were attracted to the plastic coverslip.

Functional Performance of Coatings

Modifications in ElectroNanospray-applied coatings impact the physical and functional performance of coatings. Tools have been developed for quantifying coating performance.

Two electrospray systems were used in several experiments. One system, which had a fixed target, was used to explore optimum spray conditions. The second system, which had a movable spray target platform, was used as a primary medical device, such as a stent coating apparatus. This system is described earlier in reference to FIGS. 1 and 7A and 7B. The spray head in both of these systems was a dual capillary design, in which each capillary was fed by external syringe pumps (Harvard Apparatus, Holliston, Mass., USA). A high voltage power supply (Bertan Associates, Hicksville, N.Y., USA) was used to apply voltage to the spray tip, typically over a range of 3.5-5.5 kV at ~2.5 mA. The target was moved into position by a motor-driven, computer-controlled movable stage that permitted vertical and horizontal adjustments in positioning the target with respect to the spray tip as well as a variable advancement rate of the target through the spray field. The spray operation was imaged using a video inspection microscope (Panasonic) that produced real time images of the spray tip as well as the target. The spray operation was contained within a negative pressure chamber that drew gas supply (air, nitrogen or carbon dioxide) through a filtered supply line and was vented through a filter and fume hood. Temperature and relative humidity were monitored continuously.

The system may include several features in further embodiments, such as computer controlled parameters, improved spray chamber isolation, a configurable spray platform that permits two or more spray heads, a re-designed spray nozzle for improved ease of manufacture, improved feed pumps, video imaging of multiple spray heads and the target, and software control with the ability to program process steps.

Coating Reagents

Polymers.

For these coating performance experiments, polymers available on the market that represented a range of potential coating materials may be used, from biodegradable materials to drug eluting materials. Proprietary polymers from collaborators (e.g. Dr. Judit Puskas) that were developed for this purpose may also be used.

Poly(DL-lactide-co-ϵ-caprolactone, 80/20) (PLCL), inherent viscosity 0.77 dL/g in chloroform, is a biodegradable polymer that was purchased from Absorbable Polymers International, Pelham, Ala., USA. Chronoflex AR (CFR) is polyurethane 22% solid in dimethylacetamide. CFR, a drug-eluting material, was purchased from CardioTech International, Wilmington, Mass., USA. Aborescent block co-polymers of polyisobutylene and polystyrene, TPE1, TPE4, and TPE5, were obtained from Dr. Judit Puskas at the University of Akron.

Drug.

Dexamethasone (99% purity) was purchased from Alexis Biochemicals, San Diego, Calif., USA and paclitaxel was purchased from (LC Laboratories, Woburn, Mass., USA).

Biologics.

For model biologics, we sourced three peptides with a range of sizes. Luteinizing hormone releasing hormone (LHRH), angiotensin I, and insulin B chain were obtained from Sigma-Aldrich.

Solvents.

Solvents used for these various polymers and drugs included acetone (HPLC grade), tetrahydrofuran (THF), (HPLC grade), and methanol (HPLC grade), all purchased from Sigma-Aldrich, St. Louis, USA, and for the peptides included deionized water and phosphate buffer, pH 7.4.

Preparation of Spray Materials

Solutions of polymers were prepared at different concentrations as determined by the spraying conditions. A variety of polymer concentrations and solvent combinations were investigated; acceptable concentrations (weight/volume) and primary solvents included PLCL 5% in acetone; CFR 2% in THF, and TPE1-5, 1% in THF. Dexamethasone was added to polymer solutions, with final concentrations varying from 10 to 20% of the polymer weight, resulting in a 10:1 to 5:1 polymer:dexamethasone ratio by weight respectively. Conductivity of solvent solutions was adjusted to appropriate ranges, typically by adding µl quantities of concentrated nitric acid, measured using a Orion Benchtop Conductivity Meter (Thermo Electron Corp., Waltham, Mass., USA).

Targets Used for Coating Experiments

Generic stents that could be expanded by balloon 3 fold in diameter were obtained (Pulse Systems, Concord, Calif., USA). These were fabricated from 316 stainless steel that was annealed and electropolished. Dimensions were 12 mm in length, 0.062 inches in outer diameter and 0.051 inches in inner diameter, a size which is equivalent to stents in current use.

Because some of the coating characterization tools could not be used to assess a rounded surface, flat stainless steel plates were used for some aspects of coating development. Square pieces, 1 cm square, were pressed from 12 inch square mirror-finished 316 stainless steel sheets that were 0.0312 inches thick (McMaster Can, Chicago, Ill., USA). For coating experiments, the coating was sprayed on the mirror finished side of the small cut pieces.

Determining Initial and Optimized Spray Operating Parameters

The optimal spray solvent for each polymer was determined by comparing the various solvents specified as compatible with each polymer by the manufacturer and assessing spray performance in terms of ability to form a stable cone jet (i.e. stable dark tip appearance, no fluttering between cone jet and non-cone jet mode and no corona discharge). Likewise, optimal feed rates were determined by evaluating the voltage required to generate a stable cone jet spray mode while at the same time, visually inspecting the target for obvious flaws, such as spit marks on the surface that were seen when the cone jet was disrupted. This process produced a set of voltages and feed rates for each polymer and solvent combination that were compatible with electrospray operation in the cone jet mode.

A Design of Experiment (DOE) approach was taken to setting up the experimental conditions and evaluating the impact of the various process parameters (e.g. see *DOE Simplified: Practical Tools for Effective Experimentation*. Anderson M J and Whitcomb P J. *Productivity, Inc., New York, N.Y.* 2000). Using this approach a matrix of different operating conditions was established and used to spray the flat stainless steel squares described above. Parameters evaluated included polymer concentration, drug concentration, conductivity of the solutions, spray feed rates, and spray distance to target. Outcome variables recorded included voltage, stability of the cone jet spray mode, coating weight, and the surface qualities of the coating under SEM imaging. Results of these experiments were used to guide the selection of initial operating parameters for the stent coating experiments.

Optimized conditions used to coat the samples used for the drug release studies were as follows, listed per coating surface polymer and type of finish: PLCL Open Matrix: Inner capillary feed was PLCL 5% and DXM 0.5% in acetone at a flow rate of 1.5 μl/min. The outer capillary feed was acetone with added nitric acid to achieve a conductivity of 6.8 μS/cm and at a flow rate of 5 μl/min.

PLCL Closed Film:

Inner capillary feed was PLCL 5% and DXM 0.5% in acetone at a flow rate of 0.75 μl/min. The outer capillary feed was chloroform 60% and acetone 40% at a flow rate of 10 μl/min.

TPE1 Open Matrix:

Inner capillary feed was TPE1 1% and DXM 0.1% in THF 86% and methanol 14% at a flow rate of 2 μl/min. The outer capillary feed was TPE1 0.5% and DXM 0.05% in THF 86% and methanol 14% at a flow rate of 3 μl/min.

TPE1 Closed Film:

Inner capillary feed was TPE1 1% and DXM 0.1% in THF 7 parts to 1 part ethanol at a flow rate of 2 μl/min. The outer capillary feed was THF 5 parts to 2 parts ethanol at a flow rate of 3 μl/min.

TPE4 Open Matrix:

Inner capillary feed was TPE4 1% and DXM 0.1% in THF 90% and methanol 10% at a flow rate of 2.0 μl/min. The outer capillary feed was THF 90% and methanol 10% with added nitric acid to achieve a conductivity of 0.4 μS/cm and at a flow rate of 3 μl/min.

TPE4 Closed Film:

Inner capillary feed was TPE4 90% and DXM 0.1% in THF 85% and methanol 14%, 90% of the total feed, and toluene 10% of the total feed, at a rate of 3.5 μl/min. The outer capillary feed was THF 90% and methanol 10% at a flow rate of 6.5 μl/min.

TPE5 Open:

Inner capillary feed was TPE5 1% and DXM 0.1% in THF 86% and methanol 14% at a flow rate of 0.5 μl/min. The outer capillary feed was TPE5 0.5% and DXM 0.05% in THF 86% and methanol 14% at a flow rate of 3 μl/min.

TPE5 Closed:

Inner capillary feed was TPE5 1% and DXM 0.1% in THF 7 parts to one part ethanol at a flow rate of 2.0 μl/min. The outer capillary feed was THF 5 parts to 2 parts ethanol at a flow rate of 3.0 μl/min.

Coating Weight

Coating weight at the μg scale was determined by weighing the spray target before and after spraying using a Cahn electrobalance, Model 31.

Imaging

Stents were imaged using scanning electron microscopy (SEM) to verify coating qualities, surface uniformity, and lack of void areas or webbing at strut junction points. Images were taken on multiple points over the outer and inner surfaces of the struts, at low (45×) and high (5000× and 20,000×) magnifications.

Surface coating thickness uniformity was also assessed by SEM imaging of cross sections of tangential cuts made by glass blade microtome at two or more points on each individual stent. Because the nanocomposite coating distorted under conditions of room-temperature sectioning, tangential cryomicrotomy was used to cut the coating on the selected strut at low temperature.

A series of experiments were done to find the optimal temperature. At −120° C., the coating started coming off as pieces, leaving the cutting edge clean. Because of the low stiffness of the coating, a glass knife was used to cut at 1 mm/s cutting rate and 0.5 um per step feeding rate. SEM images were then taken and the thickness for each type of coating was estimated.

Light images of stents were taken using a Nikon Model SMZ1500 stereomicroscope. Higher-magnification surface images were taken using a Hitachi Model S-3500N VP scanning electron microscope (SEM). For this, samples were mounted and then coated with gold under 250 μm Hg of argon, using 15 to of current for 1.5 minutes, and then placed on the microscope stage. For atomic force microscopy, a Molecular Imaging PicoScan/PicoSPM with Witec Pulsed Force Mode Electronics was used. The pulsed force mode enables high-resolution mapping of adhesion, stiffness and energy dissipation during break of tip-sample contact.

Drug Release Testing

Sample Incubation in Shaker Bath.

Two different methods were compared for determining the rate at which drug was released from the coated samples. In one, samples were placed into vials with 10 ml of phosphate buffered saline (PBS). These were then placed on a shaker platform with a heated chamber and gently oscillated. Incubation medium was removed for analysis at various time points (0.25, 1, 3, 7, 14, 21 and 28 days). Fresh incubation medium was replaced immediately and the incubation was continued. After the 28 day sample was taken, the sample was placed into a vial with 2 ml of acetonitrile to elute all remaining material and this was analyzed to determine the amount of drug remaining on the sample.

Measuring Drug Concentration in the Incubation Medium.

General HPLC methods to quantify dexamethasone (DXM) and three peptides (luteinizing hormone releasing hormone (human; LHRH), angiotensin I, and insulin chain B) were developed using an HP 1090 system equipped with a narrowbore column (Zorbax SB C-18, 2.1 mm i.d.×150 mm, 3.5 μm) and UV detector. Data integration and processing were performed with Agilent ChemStation software (Rev. A.08.03). Peak areas were obtained by subtracting the baseline (from a "blank" injection of the sample matrix) from the experimental chromatogram. DXM was analyzed with the following method: 20/80 to 100/0 to 20/80 acetonitrile/water in 3 min and 3.01 min at 0.6 mL/min, end run at 6 min; 65° C.; 10 μL injection volume. DXM, which was detected at 243 nm, eluted at 2.27 min. The calibration curve for DXM (obtained from Alexis Biochemicals) generated with seven standard concentrations ranging from 0.5 to 30 μg/ml in acetonitrile was adequately linear ($R^2$=0.9999) and the limit of quantification (LOQ) was 0.5 mg/ml. The peptides (all obtained from Sigma-Aldrich) were analyzed with the following method: 20/80 to 50/50 to 20/80 acetonitrile/water buffered with 0.1% (v/v) perchloric acid in 5 min and 5.01 min at 0.4 mL/min, end run at 9 min; 65° C.; 10 μL injection volume; 210 nm detection wavelength. The retention of the peptides was measured before and after the ElectroNanospray process described earlier. LHRH eluted at 2.61 min, angiotensin I eluted at 3.54 min, and insulin B chain eluted at 4.71 min. Calibration curves for the peptides were obtained using five standard concentrations ranging from 1.25 to 50 μg/ml in a solution of 10 mM perchloric acid in water. The LOD for LHRH, angiotension I and insulin chain B were 0.19, 0.25 and 0.34 μg/ml, respectively. System suitability and injection reproducibility tests were satisfactory.

Results

A variety of polymers were screened for the preliminary coating experiments. Polymers that produced detectable levels of drug in the incubation medium during the first several days of incubation were chosen for additional coating experiments. These included the following: PLCL, TPE1, TPE4, TPE 5, and CFR. Dexamethasone was used for most of the initial experiments with these polymers to permit ease of comparison. Detailed results are reported for PLCL, the biodegradable polymer, and TPE1, 4 and 5, the thermoplastic drug-eluting elastomer. CFR released very little drug during extended incubation.

Experiments with Individual Polymers and Dexamethasone.

Figure 46:
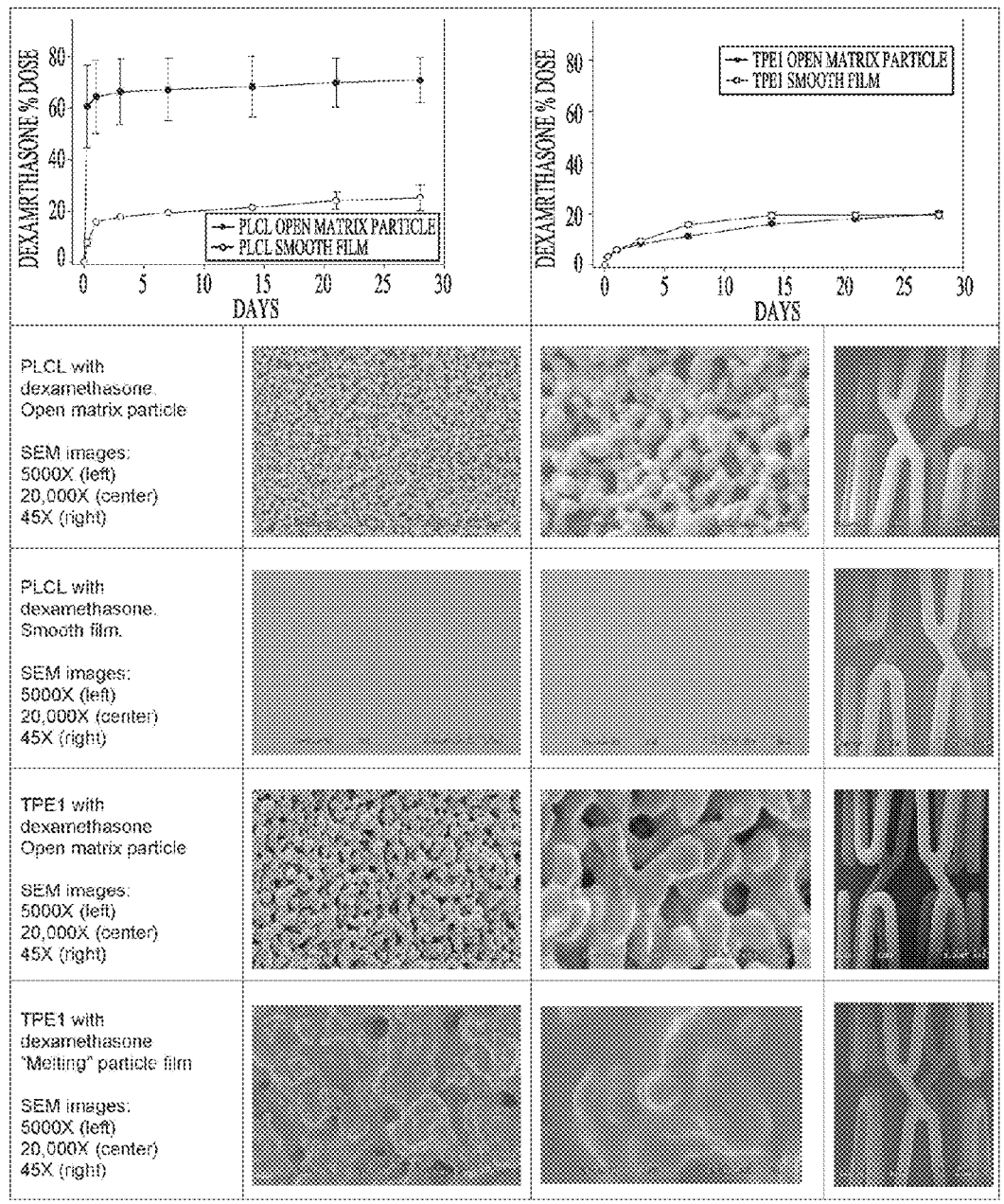
FIG. 46 illustrates cumulative dexamethasone release from PLCL and TPE1, with SEM images of the respective coating types according to an example embodiment.
Figure 47:
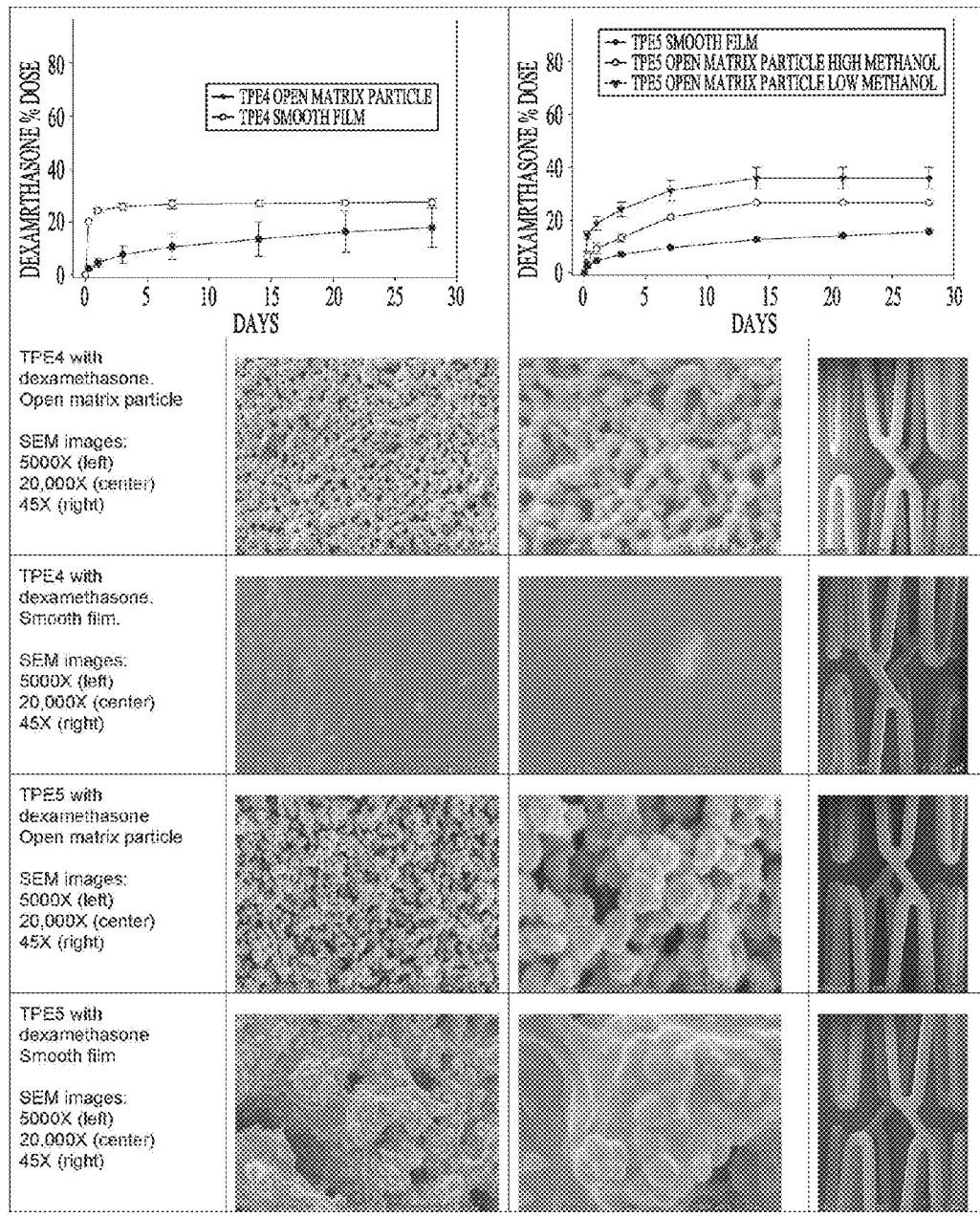
FIG. 47 illustrates cumulative dexamethasone release from TPE4 and TPE5, with SEM images of the respective coating types according to an example embodiment.

For these experiments, results are reported for coatings on stents as well as stainless steel plates. The latter provided flat surfaces that were required for subsequent AFM imaging. In FIGS. 46 and 47, cumulative dexamethasone release results, in terms of percent coating dose, are reported for two different coating morphologies that were obtained for each polymer. The distinct coating morphologies were achieved by varying flow rate, distance to target, solvent or co-solvent blend, and to a lesser degree, rate of passage of the target beneath the spray tip.

Because the coating process for TPE4 was developed first, we used similar coating parameters for applying the smooth film coatings of TPE1 and TPE5. As can be seen in the SEM images, these coatings may perhaps better be described as "melting particles," because partial particles are still visible. For each of the coatings shown below, stent surface coating was remarkably uniform on both internal and external surfaces with no visible webbing. Some surfaces show minor external particles which may be due to environmental dust which is electrostaticallly attracted to the target as the process was not conducted in a clean room environment.

Because the number of replicates for each experiment were small in these feasibility experiments, formal statistical analysis of the contrasting experiments are not reported. Nevertheless, the resulting time course release curves provide clear qualitative information about the pattern and amount of drug release for each polymer and morphology.

As we predicted based upon its much larger surface area, the open matrix particle coating of PLCL released dexamethasone very quickly during the first day of incubation as compared to the smooth film. Thereafter, the rate of release appears similar for both coatings though the total dose released is more than two-fold higher for the open matrix particle coating. In contrast, there was little difference between the open matrix particle coating and the "melting particle" coating seen for TPE1. In both cases, drug release was slow and less than 20% of the coating dose was released during the 28 days of incubation.

FIG. 46 illustrates cumulative dexamethasone release from PLCL and TPE1, with SEM images of the respective coating types. Release data obtained from PLCL on stents; TPE1 on stainless steel squares.

FIG. 47 illustrates cumulative dexamethasone release from TPE4 and TPE5, with SEM images of the respective coating types. Release data obtained from TPE4 on stents; TPE5 on stainless steel squares. Drug release results for TPE5 are particularly interesting. Three different curves are shown, one for the smooth film and the other two for open matrix particulate coatings, where two different amounts of methanol were used in the co-solvent blend. The co-solvent with the higher methanol percentage showed a release profile intermediate between the smooth film and the lower methanol blend. This is the first time we have observed shown that the solvent composition used during the application can affect the rate of drug release from the coating.

Experiments with Hybrid Coatings of One or More Morphological Surfaces and/or Polymers.

We wanted to determine if we could vary the coating morphology across the cross-sectional surface of the stent. To do this, we first applied a single, uniform layer of one polymer in a smooth film surface and then a second layer with a different morphology. In another variation, we applied two different polymers in successive layers. In all cases, we were able to achieve these hybrid coatings, though a significant limitation was the amount of material that could be deposited in the outer layer, particularly for PLCL. The simplest permutation is, of course, when both layers are comprised of the same material.

Figure 48:
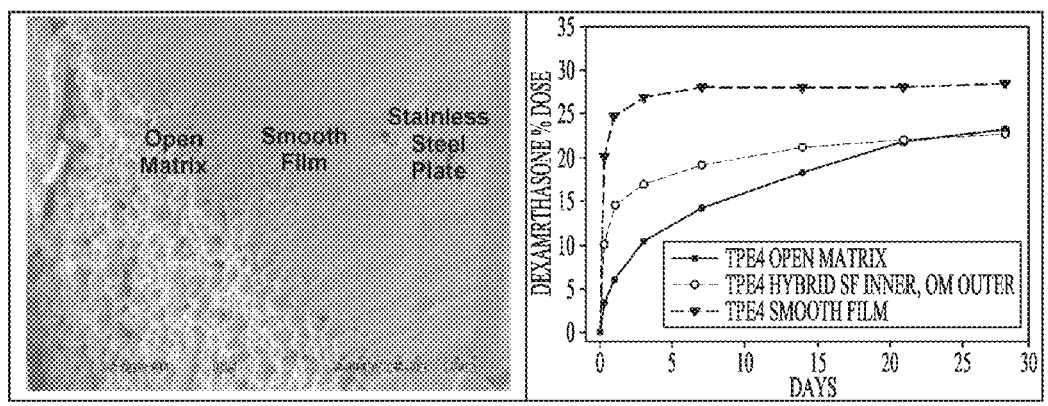
FIG. 48 illustrates results for a hybrid layer of TPE4 coated on a stainless steel plate according to an example embodiment.

In FIG. 48, results are shown for a hybrid layer of TPE4 coated on a stainless steel plate. Release results for this hybrid coating were intermediate between the smooth film and open matrix particle coating. An SEM image at 5,000× shows cross section created by cryomicrotome, where open matrix particle coating is on surface overlying the smooth film. The graph shows dexamethasone cumulative release from TPE4 open matrix particle coating and smooth film compared to a hybrid coating similar to one in the image, where the smooth film represented 300 μg and the open matrix particle coating 100 μg of total coating weight.

Preliminary Spray Experiments with Peptides

We identified and sourced three readily available peptides of varying chain length, LHRH, angiotensin I, and insulin B chain. These were sprayed in aqueous solution onto both stents and stainless steel plates. As our initial assessment of the effect of spraying on structural integrity, we used HPLC retention time of eluted peptide material following the spray experiment. This was compared to solutions of the peptides prior to spraying, as shown in FIG. 54, which shows HPLC chromatograms for angiotension I before and after spraying. Retention times were unchanged.

In further embodiments, the peptides may be sprayed in solution with at least 50 percent acetone or alcohol and co-spraying with and without PLCL. Material eluted from these 5 coating experiments was also analyzed by HPLC; preliminary results show that retention times also do not change. It should be emphasized that this provides only a limited indication of structural integrity of the peptide.

Coating morphologies may directly impact the rate and quantity of drug release from a given polymer/drug system. The dexamethasone release pattern obtained with smooth films and open matrix, nanoparticulate coatings of PLCL, a biodegradable polymer, was opposite that seen for coatings obtained with TPE4, a thermoplastic elastomer biostable polymer. The observation that a release pattern could be changed by modifying the surface morphology of the coating, and that this difference was associated with changes in the way drug was distributed within the matrix of the polymer, as shown by AFM techniques, suggests that the ElectroNanospray process has the potential to fundamentally change the drug/polymer matrix in these coatings. For the TPE group of polymers, for example, this may mean that the polyisobutylene outer layer is modified, which could impact both drug release as well as biocompatibility. The degree of control offered by ElectroNanospray is a potentially important advance.

All patents, patent documents, and references cited herein are incorporated in their entirety as if each were incorporated separately. This invention has been described with reference to illustrative embodiments and is not meant to be construed in a limiting sense. As described previously, one skilled in the art will recognize that other various illustrative applications may use the techniques as described herein to take advantage of the beneficial characteristics of the particles generated hereby. Various modifications of the illustrative embodiments, as well as additional embodiments to the invention will be apparent to persons skilled in the art upon reference to this description.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention claimed is:

1. A method of electrospraying nanoparticles on to a surface, the method comprising:
   providing a first liquid diluent to a first outer opening of a first spray head and a first liquid spray composition to a first inner opening of the first spray head, the first inner opening concentric with the first outer opening, wherein the first liquid spray composition includes an active ingredient and a polymer, and wherein the first liquid diluent includes a solvent with a dielectric constant greater than ten to at least partially dissolve the polymer;
   providing a second liquid diluent to a second outer opening of a second spray head and a second liquid spray composition to second inner opening of the second spray head, the second inner opening concentric with the second outer opening;
   charging the surface with an ionizer;
   applying a potential difference in a range of between about 2.5 kilovolts to about 6 kilovolts between the surface and the first spray head;
   spraying the first liquid diluent and the first liquid spray composition simultaneously from the first spray head onto the surface in a first pass relative to the surface to provide positively charged particles to the surface, wherein a flow rate of the first liquid diluent is less than five times the flow rate of the first liquid spray composition; and
   spraying the second liquid diluent and the second liquid spray composition from the second spray head onto the surface in a second pass relative to the surface to increase a depth of bound coating and provide negatively charged particles on the positively charged particles, the second pass occurring at a time after the first pass has completed, wherein a flow rate of the second liquid diluent is less than five times the flow rate of the second liquid spray composition.

2. The method of claim 1, further comprising including conductive elements embedded in the polymer of the first liquid spray composition, wherein the conductive elements comprise carbon black.

3. A method of electrospraying nanoparticles on to a non-conductive surface, the method comprising:
   providing a first liquid diluent to a first outer opening of a first spray head and a first liquid spray composition to a first inner opening of the first spray head, the first inner opening concentric with the first outer opening, wherein the first liquid spray composition includes an active ingredient and a polymer, and wherein the first liquid diluent includes a solvent with a dielectric constant less than ten;
   providing a second liquid diluent to a second outer opening of a second spray head and a second liquid spray composition to second inner opening of the second spray head, the second inner opening concentric with the second outer opening;
   charging the surface with an ionizer;
   spraying the first liquid diluent and the first liquid spray composition simultaneously from the first spray head onto the surface in a first pass relative to the surface to provide positively charged particles to the surface, wherein a flow rate of the first liquid diluent is greater than five times the flow rate of the first liquid spray composition; and
   spraying the second liquid diluent and the second liquid spray composition from the second spray head onto the surface in a second pass relative to the surface to increase a depth of bound coating and provide negatively charged particles on the positively charged particles, the second pass occurring at a time after the first pass has completed, wherein a flow rate of the second liquid diluent is greater than five times the flow rate of the second liquid spray composition.

4. The method of claim 3, wherein the positive and negative electrospray streams are provided by separate dual nozzle electrospray devices.

5. The method of claim 4, wherein the electrospray devices are spaced apart and the surface is moved between the sprays.

6. The method of claim 5, wherein the electrospray devices are on opposite sides of the surface, which is rotated between the corresponding positive and negative sprays.

7. The method of claim 6, wherein the electrospray devices are positioned at approximately a 45 degree angle from each other pointing toward the non-conductive surface to be coated.

8. The method of claim 3, further comprising including carbon black embedded in the polymer of the first liquid spray composition.

9. The method of claim 1, wherein spraying the first liquid diluent and the first liquid spray composition from the first spray head onto the surface in a first pass relative to the surface includes spraying the first liquid diluent and the first liquid spray composition through a charged loop electrode to pass the first liquid diluent and first liquid spray composition through a nonuniform electric field.

10. The method of claim 1, further comprising imaging the spray from the first spray head and analyzing the image to determine one or more characteristics of the spray including an angle of incidence between the spray and the surface being sprayed.

11. The method of claim 10, further comprising increasing the potential difference in response to determining the angle of incidence is greater than a specified threshold.

12. The method of claim 1, wherein providing a first liquid diluent to a first outer opening of a first spray head and a first liquid spray composition to a first inner opening of the first spray head includes providing a polymer at least partially dissolved in solvent to an intermediate opening between the outer opening and the inner opening, and wherein spraying the first liquid diluent and the first liquid spray composition simultaneously from the first spray head onto the surface in a first pass relative to the surface to provide positively charged particles to the surface includes spraying the polymer at least partially dissolved in solvent.

13. The method of claim 1, wherein the second liquid diluent and the second liquid spray composition are non-polymer.

14. The method of claim 1, wherein the dielectric constant of the solvent is in a range of between about 10 and 80.

15. The method of claim 1, further comprising spraying a third liquid diluent and third spray composition on the surface to form a closed matrix coating on the surface.

16. The method of claim 1, further comprising spraying a third liquid diluent and third spray composition on the surface to form an intermediate matrix coating on the surface.

17. The method of claim 1, further comprising providing a gas spray alongside the first spray head to help in evaporating the solvent after the solvent has left the first spray head.

18. The method of claim 3, wherein spraying the first liquid diluent and the first liquid spray composition from the first spray head onto the surface in a first pass relative to the surface includes spraying the first liquid diluent and the first liquid spray composition through a charged loop electrode to pass the first liquid diluent and first liquid spray composition through a nonuniform electric field.

19. The method of claim 3, further comprising spraying a third liquid diluent and third spray composition on the surface to form an open matrix coating on the surface.

20. The method of claim 3, further comprising spraying a third liquid diluent and third spray composition on the surface to form an intermediate matrix coating on the surface.

* * * * *